US012616742B2

(12) United States Patent
Ofori-Acquah et al.

(10) Patent No.: US 12,616,742 B2
(45) Date of Patent: May 5, 2026

(54) RECOMBINANT HEME OXYGENASE-1 (HO-1) FOR THE TREATMENT OF SICKLE CELL DISEASE

(71) Applicants: Takeda Pharmaceutical Company Limited, Osaka (JP); University of Pittsburgh-Of The Commonwealth System of Higher Education, Pittsburgh, PA (US)

(72) Inventors: Solomon Fiifi Ofori-Acquah, Pittsburgh, PA (US); Samit Ghosh, Pittsburgh, PA (US); Joseph Sypek, Lexington, MA (US); Bohong Zhang, Lexington, MA (US); Xiuxia Sun, Lexington, MA (US); Clark Q. Pan, Lexington, MA (US); Daniel Mainard Lajoie, Lexington, MA (US); Chuan Shen, Lexington, MA (US)

(73) Assignees: Takeda Pharmaceutical Company Limited, Osaka (JP); University of Pittsburgh-Of The Commonwealth System of Higher Education, Pittsburgh, PA (US)

( * ) Notice: Subject to any disclaimer, the term of this patent is extended or adjusted under 35 U.S.C. 154(b) by 646 days.

(21) Appl. No.: 17/623,503

(22) PCT Filed: Jul. 24, 2020

(86) PCT No.: PCT/US2020/043452
§ 371 (c)(1),
(2) Date: Dec. 28, 2021

(87) PCT Pub. No.: WO2021/021615
PCT Pub. Date: Feb. 4, 2021

(65) Prior Publication Data
US 2023/0018417 A1 Jan. 19, 2023

Related U.S. Application Data

(60) Provisional application No. 63/049,285, filed on Jul. 8, 2020, provisional application No. 62/879,131, filed on Jul. 26, 2019.

(51) Int. Cl.
*A61K 38/44* (2006.01)
*A61P 7/06* (2006.01)
*C12N 9/02* (2006.01)
*C12N 15/62* (2006.01)

(52) U.S. Cl.
CPC .............. *A61K 38/44* (2013.01); *A61P 7/06* (2018.01); *C12N 9/0071* (2013.01); *C12N 15/62* (2013.01); *C12Y 114/14* (2013.01)

(58) Field of Classification Search
CPC ......... A61K 38/44; A61P 7/06; C12N 9/0071; C12N 15/62; C12Y 114/14
See application file for complete search history.

(56) References Cited

U.S. PATENT DOCUMENTS

2005/0209305 A1* 9/2005 Pendrak ................... A61P 9/00
435/118
2012/0195892 A1* 8/2012 Ober ...................... A61P 35/04
424/133.1

OTHER PUBLICATIONS

Sugishima, Masakazu, et al. "Structural basis for the electron transfer from an open form of NADPH-cytochrome P450 oxidoreductase to heme oxygenase." Proceedings of the National Academy of Sciences 111.7 (2014): 2524-2529. (Year: 2014).*
Belcher, John D., et al. "Heme oxygenase-1 gene delivery by Sleeping Beauty inhibits vascular stasis in a murine model of sickle cell disease." Journal of molecular medicine 88 (2010): 665-675. (Year: 2010).*
Fusion Protein (retrieved from https://en.wikipedia.org/wiki/Fusion_protein on Oct. 8, 2024). (Year: 2024).*
Non-proteinogenic amino acids (retrieved from https://en.wikipedia.org/wiki/Non-proteinogenic_amino_acids on Oct. 9, 2023). (Year: 2024).*
Lindsay, Joseph, Jack C. Meshel, and Robert H. Patterson. "The cardiovascular manifestations of sickle cell disease." Archives of Internal medicine 133.4 (1974): 643-651. (Year: 1974).*
Wilks, Angela, et al. "Expression and characterization of truncated human heme oxygenase (hHO-1) and a fusion protein of hHO-1 with human cytochrome P450 reductase." Biochemistry 34.13 (1995): 4421-4427. (Year: 1995).*
Belcher. "Heme oxygenase-1 is a modulator of inflammation and vaso-occlusion in transgenic sickle mice", Journal of Clinical Investigation, vol. 116, No. 3, pp. 808-816, Mar. 2006.
Belcher et al. "Heme oxygenase-1 gene delivery by Sleeping Beauty inhibits vascular stasis in a murine model of sickle cell disease", Journal of Molecular Medicine, Springer, Berlin, DE, vol. 88, No. 7, pp. 665-675, Mar. 2010.
De Franceschi, "Pathophisiology of sickle cell disease and new drugs for the treatment", Mediterranean Journal of Hematology and Infectious Diseases, IT, vol. 1, No. 1, 10 pages, Jan. 2009.
International Search Report for International Patent Application No. PCT/US2020/043452, 4 pages, dated Nov. 9, 2020.

* cited by examiner

*Primary Examiner* — Robert J Yamasaki
*Assistant Examiner* — Trevor Kane
(74) *Attorney, Agent, or Firm* — Proskauer Rose LLP

(57) ABSTRACT

The present invention provides, among other things, methods and compositions for making and using recombinant heme oxygenase for treating sickle cell disease. In some embodiments, recombinant heme oxygenase proteins are truncation variants, or Fc fusion proteins with increased half-life and/or reduced aggregation.

5 Claims, 20 Drawing Sheets
Specification includes a Sequence Listing.

1-261-Fc v2

1-261-Fc v4

1-261-Fc v1

1-261-Fc v3

1-261-His

C-terminal fusion
Knob-Hole

HO-1-Fc v8

N-terminal fusion
EW-RVT S-S

HO-1-Fc v7

N-terminal fusion
DD-KK

HO-1-Fc v6

N-terminal fusion
Knob-Hole S-S

HO-1-Fc v5

1-261
no linker

C-terminal fusion
EW-RVT
HO-1-Fc v9

1-226
no linker

C-terminal fusion

HO-1-Fc v10

1-226
no linker

N-terminal fusion
Homodimer
HO-1-Fc v11

1-226
no linker

C-terminal fusion
Homodimer
HO-1-Fc v12

C-terminal fusion
Single chain (G4S)13
Reverse charge K-D

HO-1-Fc v16

C-terminal fusion
Single chain (G4S)8

HO-1-Fc v15

C-terminal fusion
Single chain (G4S)13
Reverse charge K-D

HO-1-Fc v14

C-terminal fusion
Homodimer

HO-1-Fc v13

SEQUENCE LISTING

<160> NUMBER OF SEQ ID NOS: 65

<210> SEQ ID NO 1
<211> LENGTH: 288
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Met Glu Arg Pro Gln Pro Asp Ser Met Pro Gln Asp Leu Ser Glu Ala
1               5                   10                  15

Leu Lys Glu Ala Thr Lys Glu Val His Thr Gln Ala Glu Asn Ala Glu
            20                  25                  30

Phe Met Arg Asn Phe Gln Lys Gly Gln Val Thr Arg Asp Gly Phe Lys
        35                  40                  45

Leu Val Met Ala Ser Leu Tyr His Ile Tyr Val Ala Leu Glu Glu Glu
    50                  55                  60

Ile Glu Arg Asn Lys Glu Ser Pro Val Phe Ala Pro Val Tyr Phe Pro
65                  70                  75                  80

Glu Glu Leu His Arg Lys Ala Ala Leu Glu Gln Asp Leu Ala Phe Trp
                85                  90                  95

Tyr Gly Pro Arg Trp Gln Glu Val Ile Pro Tyr Thr Pro Ala Met Gln
            100                 105                 110

Arg Tyr Val Lys Arg Leu His Glu Val Gly Arg Thr Glu Pro Glu Leu
        115                 120                 125

Leu Val Ala His Ala Tyr Thr Arg Tyr Leu Gly Asp Leu Ser Gly Gly
    130                 135                 140

Gln Val Leu Lys Lys Ile Ala Gln Lys Ala Leu Asp Leu Pro Ser Ser
145                 150                 155                 160

Gly Glu Gly Leu Ala Phe Phe Thr Phe Pro Asn Ile Ala Ser Ala Thr
                165                 170                 175

Lys Phe Lys Gln Leu Tyr Arg Ser Arg Met Asn Ser Leu Glu Met Thr
            180                 185                 190

Pro Ala Val Arg Gln Arg Val Ile Glu Glu Ala Lys Thr Ala Phe Leu
        195                 200                 205

Leu Asn Ile Gln Leu Phe Glu Glu Leu Gln Glu Leu Leu Thr His Asp
    210                 215                 220

Thr Lys Asp Gln Ser Pro Ser Arg Ala Pro Gly Leu Arg Gln Arg Ala
225                 230                 235                 240

Ser Asn Lys Val Gln Asp Ser Ala Pro Val Glu Thr Pro Arg Gly Lys
                245                 250                 255

Pro Pro Leu Asn Thr Arg Ser Gln Ala Pro Leu Leu Arg Trp Val Leu
            260                 265                 270

-continued

```
Thr Leu Ser Phe Leu Val Ala Thr Val Ala Val Gly Leu Tyr Ala Met
        275                 280                 285
```

```
<210> SEQ ID NO 2
<211> LENGTH: 267
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2
```

```
Met Glu Arg Pro Gln Pro Asp Ser Met Pro Gln Asp Leu Ser Glu Ala
1               5                   10                  15
```

```
Leu Lys Glu Ala Thr Lys Glu Val His Thr Gln Ala Glu Asn Ala Glu
            20                  25                  30
```

```
Phe Met Arg Asn Phe Gln Lys Gly Gln Val Thr Arg Asp Gly Phe Lys
        35                  40                  45
```

```
Leu Val Met Ala Ser Leu Tyr His Ile Tyr Val Ala Leu Glu Glu Glu
    50                  55                  60
```

```
Ile Glu Arg Asn Lys Glu Ser Pro Val Phe Ala Pro Val Tyr Phe Pro
65                  70                  75                  80
```

```
Glu Glu Leu His Arg Lys Ala Ala Leu Glu Gln Asp Leu Ala Phe Trp
            85                  90                  95
```

```
Tyr Gly Pro Arg Trp Gln Glu Val Ile Pro Tyr Thr Pro Ala Met Gln
            100                 105                 110
```

```
Arg Tyr Val Lys Arg Leu His Glu Val Gly Arg Thr Glu Pro Glu Leu
            115                 120                 125
```

```
Leu Val Ala His Ala Tyr Thr Arg Tyr Leu Gly Asp Leu Ser Gly Gly
    130                 135                 140
```

```
Gln Val Leu Lys Lys Ile Ala Gln Lys Ala Leu Asp Leu Pro Ser Ser
145                 150                 155                 160
```

```
Gly Glu Gly Leu Ala Phe Phe Thr Phe Pro Asn Ile Ala Ser Ala Thr
            165                 170                 175
```

```
Lys Phe Lys Gln Leu Tyr Arg Ser Arg Met Asn Ser Leu Glu Met Thr
            180                 185                 190
```

```
Pro Ala Val Arg Gln Arg Val Ile Glu Glu Ala Lys Thr Ala Phe Leu
            195                 200                 205
```

```
Leu Asn Ile Gln Leu Phe Glu Glu Leu Gln Glu Leu Leu Thr His Asp
    210                 215                 220
```

```
Thr Lys Asp Gln Ser Pro Ser Arg Ala Pro Gly Leu Arg Gln Arg Ala
225                 230                 235                 240
```

```
Ser Asn Lys Val Gln Asp Ser Ala Pro Val Glu Thr Pro Arg Gly Lys
            245                 250                 255
```

```
Pro Pro Leu Asn Thr His His His His His
            260                 265
```

```
<210> SEQ ID NO 3
<211> LENGTH: 261
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3
```

-continued

```
Met Glu Arg Pro Gln Pro Asp Ser Met Pro Gln Asp Leu Ser Glu Ala
1               5                   10                  15

Leu Lys Glu Ala Thr Lys Glu Val His Thr Gln Ala Glu Asn Ala Glu
            20                  25                  30

Phe Met Arg Asn Phe Gln Lys Gly Gln Val Thr Arg Asp Gly Phe Lys
        35                  40                  45

Leu Val Met Ala Ser Leu Tyr His Ile Tyr Val Ala Leu Glu Glu Glu
    50                  55                  60

Ile Glu Arg Asn Lys Glu Ser Pro Val Phe Ala Pro Val Tyr Phe Pro
65                  70                  75                  80

Glu Glu Leu His Arg Lys Ala Ala Leu Glu Gln Asp Leu Ala Phe Trp
                85                  90                  95

Tyr Gly Pro Arg Trp Gln Glu Val Ile Pro Tyr Thr Pro Ala Met Gln
            100                 105                 110

Arg Tyr Val Lys Arg Leu His Glu Val Gly Arg Thr Glu Pro Glu Leu
        115                 120                 125

Leu Val Ala His Ala Tyr Thr Arg Tyr Leu Gly Asp Leu Ser Gly Gly
    130                 135                 140

Gln Val Leu Lys Lys Ile Ala Gln Lys Ala Leu Asp Leu Pro Ser Ser
145                 150                 155                 160

Gly Glu Gly Leu Ala Phe Phe Thr Phe Pro Asn Ile Ala Ser Ala Thr
                165                 170                 175

Lys Phe Lys Gln Leu Tyr Arg Ser Arg Met Asn Ser Leu Glu Met Thr
            180                 185                 190

Pro Ala Val Arg Gln Arg Val Ile Glu Glu Ala Lys Thr Ala Phe Leu
        195                 200                 205

Leu Asn Ile Gln Leu Phe Glu Glu Leu Gln Glu Leu Leu Thr His Asp
    210                 215                 220

Thr Lys Asp Gln Ser Pro Ser Arg Ala Pro Gly Leu Arg Gln Arg Ala
225                 230                 235                 240

Ser Asn Lys Val Gln Asp Ser Ala Pro Val Glu Thr Pro Arg Gly Lys
                245                 250                 255

Pro Pro Leu Asn Thr
            260
```

<210> SEQ ID NO 4
<211> LENGTH: 488
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

```
Met Glu Arg Pro Gln Pro Asp Ser Met Pro Gln Asp Leu Ser Glu Ala
1               5                   10                  15

Leu Lys Glu Ala Thr Lys Glu Val His Thr Gln Ala Glu Asn Ala Glu
            20                  25                  30

Phe Met Arg Asn Phe Gln Lys Gly Gln Val Thr Arg Asp Gly Phe Lys
        35                  40                  45

Leu Val Met Ala Ser Leu Tyr His Ile Tyr Val Ala Leu Glu Glu Glu
    50                  55                  60

Ile Glu Arg Asn Lys Glu Ser Pro Val Phe Ala Pro Val Tyr Phe Pro
65                  70                  75                  80

Glu Glu Leu His Arg Lys Ala Ala Leu Glu Gln Asp Leu Ala Phe Trp
```

```
                    85                 90                 95
Tyr Gly Pro Arg Trp Gln Glu Val Ile Pro Tyr Thr Pro Ala Met Gln
            100                 105                 110

Arg Tyr Val Lys Arg Leu His Glu Val Gly Arg Thr Glu Pro Glu Leu
            115                 120                 125

Leu Val Ala His Ala Tyr Thr Arg Tyr Leu Gly Asp Leu Ser Gly Gly
        130                 135                 140

Gln Val Leu Lys Lys Ile Ala Gln Lys Ala Leu Asp Leu Pro Ser Ser
145                 150                 155                 160

Gly Glu Gly Leu Ala Phe Phe Thr Phe Pro Asn Ile Ala Ser Ala Thr
                165                 170                 175

Lys Phe Lys Gln Leu Tyr Arg Ser Arg Met Asn Ser Leu Glu Met Thr
                180                 185                 190

Pro Ala Val Arg Gln Arg Val Ile Glu Glu Ala Lys Thr Ala Phe Leu
            195                 200                 205

Leu Asn Ile Gln Leu Phe Glu Glu Leu Gln Glu Leu Leu Thr His Asp
        210                 215                 220

Thr Lys Asp Gln Ser Pro Ser Arg Ala Pro Gly Leu Arg Gln Arg Ala
225                 230                 235                 240

Ser Asn Lys Val Gln Asp Ser Ala Pro Val Glu Thr Pro Arg Gly Lys
                245                 250                 255

Pro Pro Leu Asn Thr Asp Lys Thr His Thr Cys Pro Pro Cys Pro Ala
                260                 265                 270

Pro Glu Ala Ala Gly Gly Pro Ser Val Phe Leu Phe Pro Pro Lys Pro
            275                 280                 285

Lys Asp Thr Leu Met Ile Ser Arg Thr Pro Glu Val Thr Cys Val Val
        290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
            355                 360                 365

Leu Pro Ala Pro Ile Glu Lys Thr Ile Ser Lys Ala Lys Gly Gln Pro
        370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
            435                 440                 445

Ser Lys Leu Thr Val Asp Lys Ser Arg Trp Gln Gln Gly Asn Val Phe
        450                 455                 460

Ser Cys Ser Val Met His Glu Ala Leu His Asn His Tyr Thr Gln Lys
465                 470                 475                 480

Ser Leu Ser Leu Ser Pro Gly Lys
                485
```

<210> SEQ ID NO 5

-continued

```
<211> LENGTH: 508
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Met Glu Arg Pro Gln Pro Asp Ser Met Pro Gln Asp Leu Ser Glu Ala
1               5                   10                  15

Leu Lys Glu Ala Thr Lys Glu Val His Thr Gln Ala Glu Asn Ala Glu
                20                  25                  30

Phe Met Arg Asn Phe Gln Lys Gly Gln Val Thr Arg Asp Gly Phe Lys
            35                  40                  45

Leu Val Met Ala Ser Leu Tyr His Ile Tyr Val Ala Leu Glu Glu Glu
        50                  55                  60

Ile Glu Arg Asn Lys Glu Ser Pro Val Phe Ala Pro Val Tyr Phe Pro
65                  70                  75                  80

Glu Glu Leu His Arg Lys Ala Ala Leu Glu Gln Asp Leu Ala Phe Trp
                85                  90                  95

Tyr Gly Pro Arg Trp Gln Glu Val Ile Pro Tyr Thr Pro Ala Met Gln
            100                 105                 110

Arg Tyr Val Lys Arg Leu His Glu Val Gly Arg Thr Glu Pro Glu Leu
            115                 120                 125

Leu Val Ala His Ala Tyr Thr Arg Tyr Leu Gly Asp Leu Ser Gly Gly
        130                 135                 140

Gln Val Leu Lys Lys Ile Ala Gln Lys Ala Leu Asp Leu Pro Ser Ser
145                 150                 155                 160

Gly Glu Gly Leu Ala Phe Phe Thr Phe Pro Asn Ile Ala Ser Ala Thr
                165                 170                 175

Lys Phe Lys Gln Leu Tyr Arg Ser Arg Met Asn Ser Leu Glu Met Thr
            180                 185                 190

Pro Ala Val Arg Gln Arg Val Ile Glu Glu Ala Lys Thr Ala Phe Leu
            195                 200                 205

Leu Asn Ile Gln Leu Phe Glu Glu Leu Gln Glu Leu Leu Thr His Asp
        210                 215                 220

Thr Lys Asp Gln Ser Pro Ser Arg Ala Pro Gly Leu Arg Gln Arg Ala
225                 230                 235                 240

Ser Asn Lys Val Gln Asp Ser Ala Pro Val Glu Thr Pro Arg Gly Lys
                245                 250                 255

Pro Pro Leu Asn Thr Gly Gly Gly Gly Ser Gly Gly Gly Gly Ser Gly
            260                 265                 270

Gly Gly Gly Ser Gly Gly Gly Gly Ser Asp Lys Thr His Thr Cys Pro
            275                 280                 285

Pro Cys Pro Ala Pro Glu Ala Ala Gly Gly Pro Ser Val Phe Leu Phe
        290                 295                 300

Pro Pro Lys Pro Lys Asp Thr Leu Met Ile Ser Arg Thr Pro Glu Val
305                 310                 315                 320

Thr Cys Val Val Val Asp Val Ser His Glu Asp Pro Glu Val Lys Phe
                325                 330                 335

Asn Trp Tyr Val Asp Gly Val Glu Val His Asn Ala Lys Thr Lys Pro
            340                 345                 350

Arg Glu Glu Gln Tyr Asn Ser Thr Tyr Arg Val Val Ser Val Leu Thr
            355                 360                 365
```

```
Val Leu His Gln Asp Trp Leu Asn Gly Lys Glu Tyr Lys Cys Lys Val
370             375             380

Ser Asn Lys Ala Leu Pro Ala Pro Ile Glu Lys Thr Ile Ser Lys Ala
385             390             395             400

Lys Gly Gln Pro Arg Glu Pro Gln Val Tyr Thr Leu Pro Pro Ser Arg
                405             410             415

Asp Glu Leu Thr Lys Asn Gln Val Ser Leu Thr Cys Leu Val Lys Gly
            420             425             430

Phe Tyr Pro Ser Asp Ile Ala Val Glu Trp Glu Ser Asn Gly Gln Pro
            435             440             445

Glu Asn Asn Tyr Lys Thr Thr Pro Pro Val Leu Asp Ser Asp Gly Ser
        450             455             460

Phe Phe Leu Tyr Ser Lys Leu Thr Val Asp Lys Ser Arg Trp Gln Gln
465             470             475             480

Gly Asn Val Phe Ser Cys Ser Val Met His Glu Ala Leu His Asn His
            485             490             495

Tyr Thr Gln Lys Ser Leu Ser Leu Ser Pro Gly Lys
            500             505
```

```
<210> SEQ ID NO 6
<211> LENGTH: 508
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6
```

```
Met Asp Lys Thr His Thr Cys Pro Pro Cys Pro Ala Pro Glu Ala Ala
1               5               10              15

Gly Gly Pro Ser Val Phe Leu Phe Pro Pro Lys Pro Lys Asp Thr Leu
            20              25              30

Met Ile Ser Arg Thr Pro Glu Val Thr Cys Val Val Val Asp Val Ser
            35              40              45

His Glu Asp Pro Glu Val Lys Phe Asn Trp Tyr Val Asp Gly Val Glu
    50              55              60

Val His Asn Ala Lys Thr Lys Pro Arg Glu Glu Gln Tyr Asn Ser Thr
65              70              75              80

Tyr Arg Val Val Ser Val Leu Thr Val Leu His Gln Asp Trp Leu Asn
            85              90              95

Gly Lys Glu Tyr Lys Cys Lys Val Ser Asn Lys Ala Leu Pro Ala Pro
            100             105             110

Ile Glu Lys Thr Ile Ser Lys Ala Lys Gly Gln Pro Arg Glu Pro Gln
            115             120             125

Val Tyr Thr Leu Pro Pro Ser Arg Asp Glu Leu Thr Lys Asn Gln Val
    130             135             140

Ser Leu Thr Cys Leu Val Lys Gly Phe Tyr Pro Ser Asp Ile Ala Val
145             150             155             160

Glu Trp Glu Ser Asn Gly Gln Pro Glu Asn Asn Tyr Lys Thr Thr Pro
            165             170             175

Pro Val Leu Asp Ser Asp Gly Ser Phe Phe Leu Tyr Ser Lys Leu Thr
            180             185             190

Val Asp Lys Ser Arg Trp Gln Gln Gly Asn Val Phe Ser Cys Ser Val
    195             200             205

Met His Glu Ala Leu His Asn His Tyr Thr Gln Lys Ser Leu Ser Leu
```

```
                210               215               220

Ser Pro Gly Lys Gly Gly Gly Ser Gly Gly Gly Gly Ser Gly Gly
225             230               235               240

Gly Gly Ser Gly Gly Gly Gly Ser Glu Arg Pro Gln Pro Asp Ser Met
            245               250               255

Pro Gln Asp Leu Ser Glu Ala Leu Lys Glu Ala Thr Lys Glu Val His
            260               265               270

Thr Gln Ala Glu Asn Ala Glu Phe Met Arg Asn Phe Gln Lys Gly Gln
        275               280               285

Val Thr Arg Asp Gly Phe Lys Leu Val Met Ala Ser Leu Tyr His Ile
    290               295               300

Tyr Val Ala Leu Glu Glu Glu Ile Glu Arg Asn Lys Glu Ser Pro Val
305             310               315               320

Phe Ala Pro Val Tyr Phe Pro Glu Glu Leu His Arg Lys Ala Ala Leu
                325               330               335

Glu Gln Asp Leu Ala Phe Trp Tyr Gly Pro Arg Trp Gln Glu Val Ile
            340               345               350

Pro Tyr Thr Pro Ala Met Gln Arg Tyr Val Lys Arg Leu His Glu Val
            355               360               365

Gly Arg Thr Glu Pro Glu Leu Leu Val Ala His Ala Tyr Thr Arg Tyr
    370               375               380

Leu Gly Asp Leu Ser Gly Gly Gln Val Leu Lys Lys Ile Ala Gln Lys
385             390               395               400

Ala Leu Asp Leu Pro Ser Ser Gly Glu Gly Leu Ala Phe Phe Thr Phe
                405               410               415

Pro Asn Ile Ala Ser Ala Thr Lys Phe Lys Gln Leu Tyr Arg Ser Arg
                420               425               430

Met Asn Ser Leu Glu Met Thr Pro Ala Val Arg Gln Arg Val Ile Glu
            435               440               445

Glu Ala Lys Thr Ala Phe Leu Leu Asn Ile Gln Leu Phe Glu Glu Leu
    450               455               460

Gln Glu Leu Leu Thr His Asp Thr Lys Asp Gln Ser Pro Ser Arg Ala
465               470               475               480

Pro Gly Leu Arg Gln Arg Ala Ser Asn Lys Val Gln Asp Ser Ala Pro
            485               490               495

Val Glu Thr Pro Arg Gly Lys Pro Pro Leu Asn Thr
            500               505
```

```
<210> SEQ ID NO 7
<211> LENGTH: 488
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Met Glu Arg Pro Gln Pro Asp Ser Met Pro Gln Asp Leu Ser Glu Ala
1               5               10               15

Leu Lys Glu Ala Thr Lys Glu Val His Thr Gln Ala Glu Asn Ala Glu
            20               25               30

Phe Met Arg Asn Phe Gln Lys Gly Gln Val Thr Arg Asp Gly Phe Lys
        35               40               45

Leu Val Met Ala Ser Leu Tyr His Ile Tyr Val Ala Leu Glu Glu Glu
    50               55               60
```

Ile Glu Arg Asn Lys Glu Ser Pro Val Phe Ala Pro Val Tyr Phe Pro
65                  70                  75                  80

Glu Glu Leu His Arg Lys Ala Ala Leu Glu Gln Asp Leu Ala Phe Trp
                    85                  90                  95

Tyr Gly Pro Arg Trp Gln Glu Val Ile Pro Tyr Thr Pro Ala Met Gln
                100                 105                 110

Arg Tyr Val Lys Arg Leu His Glu Val Gly Arg Thr Glu Pro Glu Leu
                115                 120                 125

Leu Val Ala His Ala Tyr Thr Arg Tyr Leu Gly Asp Leu Ser Gly Gly
        130                 135                 140

Gln Val Leu Lys Lys Ile Ala Gln Lys Ala Leu Asp Leu Pro Ser Ser
145                 150                 155                 160

Gly Glu Gly Leu Ala Phe Phe Thr Phe Pro Asn Ile Ala Ser Ala Thr
                165                 170                 175

Lys Phe Lys Gln Leu Tyr Arg Ser Arg Met Asn Ser Leu Glu Met Thr
                180                 185                 190

Pro Ala Val Arg Gln Arg Val Ile Glu Glu Ala Lys Thr Ala Phe Leu
                195                 200                 205

Leu Asn Ile Gln Leu Phe Glu Glu Leu Gln Glu Leu Leu Thr His Asp
        210                 215                 220

Thr Lys Asp Gln Ser Pro Ser Arg Ala Pro Gly Leu Arg Gln Arg Ala
225                 230                 235                 240

Ser Asn Lys Val Gln Asp Ser Ala Pro Val Glu Thr Pro Arg Gly Lys
                245                 250                 255

Pro Pro Leu Asn Thr Asp Lys Thr His Thr Cys Pro Pro Cys Pro Ala
                260                 265                 270

Pro Glu Ala Ala Gly Gly Pro Ser Val Phe Leu Phe Pro Pro Lys Pro
                275                 280                 285

Lys Asp Thr Leu Met Ile Ser Arg Thr Pro Glu Val Thr Cys Val Val
        290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
                340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
        370                 375                 380

Arg Glu Pro Gln Val Tyr Val Tyr Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
                420                 425                 430

Lys Thr Thr Pro Pro Val Leu Asp Ser Asp Gly Ser Phe Ala Leu Val
                435                 440                 445

Ser Lys Leu Thr Val Asp Lys Ser Arg Trp Gln Gln Gly Asn Val Phe
        450                 455                 460

Ser Cys Ser Val Met His Glu Ala Leu His Asn His Tyr Thr Gln Lys
465                 470                 475                 480

Ser Leu Ser Leu Ser Pro Gly Lys
            485

<210> SEQ ID NO 8
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Val Leu Pro Pro Ser Arg Asp Glu Leu Thr Lys Asn Gln Val Ser
    130                 135                 140

Leu Leu Cys Leu Val Lys Gly Phe Tyr Pro Ser Asp Ile Ala Val Glu
145                 150                 155                 160

Trp Glu Ser Asn Gly Gln Pro Glu Asn Asn Tyr Leu Thr Trp Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 9
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Met Asp Met Arg Val Pro Ala Gln Leu Leu Gly Leu Leu Leu Leu Trp
1               5                   10                  15

Phe Pro Gly Ser Arg Cys
            20

-continued

```
<210> SEQ ID NO 10
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gly Gly Gly Gly Ser
1               5

<210> SEQ ID NO 11
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Gly Gly Gly
1

<210> SEQ ID NO 12
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Ala Pro Gly Gly Gly Gly Gly Ala Ala Ala Ala Ala Gly Gly Gly
1               5                   10                  15

Gly Gly Gly Ala Pro
            20

<210> SEQ ID NO 13
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Gly Ala Pro Gly Gly Gly Gly Ala Ala Ala Ala Ala Gly Gly Gly
1               5                   10                  15

Gly Gly Gly Ala Pro Gly Gly Gly Gly Gly Ala Ala Ala Ala Ala Gly
            20                  25                  30

Gly Gly Gly Gly Gly Ala Pro
        35

<210> SEQ ID NO 14
<211> LENGTH: 57
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14
```

```
Gly Ala Pro Gly Gly Gly Gly Ala Ala Ala Ala Gly Gly Gly
1               5               10              15

Gly Gly Gly Ala Pro Gly Gly Gly Gly Ala Ala Ala Ala Ala Gly
            20              25              30

Gly Gly Gly Gly Gly Ala Pro Gly Gly Gly Gly Gly Ala Ala Ala Ala
        35              40              45

Ala Gly Gly Gly Gly Gly Gly Ala Pro
    50              55
```

<210> SEQ ID NO 15
<211> LENGTH: 227
<212> TYPE: PRT
<213> ORGANISM: Homo sapiens

<400> SEQUENCE: 15

```
Asp Lys Thr His Thr Cys Pro Pro Cys Pro Ala Pro Glu Leu Leu Gly
1               5               10              15

Gly Pro Ser Val Phe Leu Phe Pro Pro Lys Pro Lys Asp Thr Leu Met
            20              25              30

Ile Ser Arg Thr Pro Glu Val Thr Cys Val Val Val Asp Val Ser His
        35              40              45

Glu Asp Pro Glu Val Lys Phe Asn Trp Tyr Val Asp Gly Val Glu Val
    50              55              60

His Asn Ala Lys Thr Lys Pro Arg Glu Glu Gln Tyr Asn Ser Thr Tyr
65              70              75              80

Arg Val Val Ser Val Leu Thr Val Leu His Gln Asp Trp Leu Asn Gly
            85              90              95

Lys Glu Tyr Lys Cys Lys Val Ser Asn Lys Ala Leu Pro Ala Pro Ile
            100             105             110

Glu Lys Thr Ile Ser Lys Ala Lys Gly Gln Pro Arg Glu Pro Gln Val
            115             120             125

Tyr Thr Leu Pro Pro Ser Arg Asp Glu Leu Thr Lys Asn Gln Val Ser
    130             135             140

Leu Thr Cys Leu Val Lys Gly Phe Tyr Pro Ser Asp Ile Ala Val Glu
145             150             155             160

Trp Glu Ser Asn Gly Gln Pro Glu Asn Asn Tyr Lys Thr Thr Pro Pro
            165             170             175

Val Leu Asp Ser Asp Gly Ser Phe Phe Leu Tyr Ser Lys Leu Thr Val
            180             185             190

Asp Lys Ser Arg Trp Gln Gln Gly Asn Val Phe Ser Cys Ser Val Met
            195             200             205

His Glu Ala Leu His Asn His Tyr Thr Gln Lys Ser Leu Ser Leu Ser
    210             215             220

Pro Gly Lys
225
```

<210> SEQ ID NO 16
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

```
Asp Lys Thr His Thr Cys Pro Pro Cys Pro Ala Pro Glu Ala Ala Gly
```

```
1                5                    10                   15

Gly Pro Ser Val Phe Leu Phe Pro Pro Lys Pro Lys Asp Thr Leu Met
                20                   25                   30

Ile Ser Arg Thr Pro Glu Val Thr Cys Val Val Val Asp Val Ser His
                35                   40                   45

Glu Asp Pro Glu Val Lys Phe Asn Trp Tyr Val Asp Gly Val Glu Val
        50                   55                   60

His Asn Ala Lys Thr Lys Pro Arg Glu Glu Gln Tyr Asn Ser Thr Tyr
65                   70                   75                   80

Arg Val Val Ser Val Leu Thr Val Leu His Gln Asp Trp Leu Asn Gly
                85                   90                   95

Lys Glu Tyr Lys Cys Lys Val Ser Asn Lys Ala Leu Pro Ala Pro Ile
                100                  105                  110

Glu Lys Thr Ile Ser Lys Ala Lys Gly Gln Pro Arg Glu Pro Gln Val
                115                  120                  125

Tyr Thr Leu Pro Pro Ser Arg Asp Glu Leu Thr Lys Asn Gln Val Ser
        130                  135                  140

Leu Thr Cys Leu Val Lys Gly Phe Tyr Pro Ser Asp Ile Ala Val Glu
145                  150                  155                  160

Trp Glu Ser Asn Gly Gln Pro Glu Asn Asn Tyr Lys Thr Thr Pro Pro
                165                  170                  175

Val Leu Asp Ser Asp Gly Ser Phe Phe Leu Tyr Ser Lys Leu Thr Val
                180                  185                  190

Asp Lys Ser Arg Trp Gln Gln Gly Asn Val Phe Ser Cys Ser Val Met
        195                  200                  205

His Glu Ala Leu His Asn His Tyr Thr Gln Lys Ser Leu Ser Leu Ser
        210                  215                  220

Pro Gly Lys
225

<210> SEQ ID NO 17
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Asp Lys Thr His Thr Cys Pro Pro Cys Pro Ala Pro Glu Leu Leu Gly
1                5                    10                   15

Gly Pro Ser Val Phe Leu Phe Pro Pro Lys Pro Lys Asp Thr Leu Met
                20                   25                   30

Ile Ser Arg Thr Pro Glu Val Thr Cys Val Val Val Asp Val Ser His
                35                   40                   45

Glu Asp Pro Glu Val Lys Phe Asn Trp Tyr Val Asp Gly Val Glu Val
        50                   55                   60

His Asn Ala Lys Thr Lys Pro Arg Glu Glu Gln Tyr Asn Ser Thr Tyr
65                   70                   75                   80

Arg Val Val Ser Val Leu Thr Val Leu His Gln Asp Trp Leu Asn Gly
                85                   90                   95

Lys Glu Tyr Lys Cys Lys Val Ser Asn Lys Ala Leu Pro Ala Pro Ile
                100                  105                  110

Glu Lys Thr Ile Ser Lys Ala Lys Gly Gln Pro Arg Glu Pro Gln Val
                115                  120                  125
```

-continued

```
Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu Lys Phe His Tyr Thr Gln Lys Ser Leu Ser Leu Ser
    210                 215                 220

Pro Gly Lys
225

<210> SEQ ID NO 18
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
    115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu Lys Phe His Tyr Thr Gln Lys Ser Leu Ser Leu Ser
    210                 215                 220

Pro Gly Lys
225
```

```
<210> SEQ ID NO 19
<211> LENGTH: 232
<212> TYPE: PRT
<213> ORGANISM: Unknown
<220> FEATURE:
<221> NAME/KEY: source
<223> OTHER INFORMATION: /note="Description of Unknown:
      Fc domain sequence"

<400> SEQUENCE: 19

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro Gly Lys
225                 230

<210> SEQ ID NO 20
<211> LENGTH: 226
<212> TYPE: PRT
<213> ORGANISM: Unknown
<220> FEATURE:
<221> NAME/KEY: source
<223> OTHER INFORMATION: /note="Description of Unknown:
      Fc domain sequence"

<400> SEQUENCE: 20

Lys Thr His Thr Cys Pro Pro Cys Pro Ala Pro Glu Leu Leu Gly Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser His Glu
        35                  40                  45

Asp Pro Glu Val Lys Phe Asn Trp Tyr Val Asp Gly Val Glu Val His
```

-continued

```
          50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
                100                 105                 110

Lys Thr Ile Ser Lys Ala Lys Gly Gln Pro Arg Glu Pro Gln Val Tyr
            115                 120                 125

Thr Leu Pro Pro Ser Arg Asp Glu Leu Thr Lys Asn Gln Val Ser Leu
        130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
                180                 185                 190

Lys Ser Arg Trp Gln Gln Gly Asn Val Phe Ser Cys Ser Val Met His
            195                 200                 205

Glu Ala Leu His Asn His Tyr Thr Gln Lys Ser Leu Ser Leu Ser Pro
        210                 215                 220

Gly Lys
225

<210> SEQ ID NO 21
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Gly Gly Gly Gly Ser Gly Gly Gly Ser Gly Gly Gly Ser Gly
1               5                   10                  15

Gly Gly Gly Ser
            20

<210> SEQ ID NO 22
<211> LENGTH: 487
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80
```

```
Arg Val Val Ser Val Leu Thr Val Leu His Gln Asp Trp Leu Asn Gly
             85              90              95

Lys Glu Tyr Lys Cys Lys Val Ser Asn Lys Ala Leu Pro Ala Pro Ile
             100             105             110

Glu Lys Thr Ile Ser Lys Ala Lys Gly Gln Pro Arg Glu Pro Gln Val
             115             120             125

Tyr Thr Leu Pro Pro Cys Arg Asp Glu Leu Thr Lys Asn Gln Val Ser
     130             135             140

Leu Trp Cys Leu Val Lys Gly Phe Tyr Pro Ser Asp Ile Ala Val Glu
145             150             155             160

Trp Glu Ser Asn Gly Gln Pro Glu Asn Asn Tyr Lys Thr Thr Pro Pro
                 165             170             175

Val Leu Asp Ser Asp Gly Ser Phe Phe Leu Tyr Ser Lys Leu Thr Val
             180             185             190

Asp Lys Ser Arg Trp Gln Gln Gly Asn Val Phe Ser Cys Ser Val Met
             195             200             205

His Glu Ala Leu His Asn His Tyr Thr Gln Lys Ser Leu Ser Leu Ser
     210             215             220

Pro Gly Met Glu Arg Pro Gln Pro Asp Ser Met Pro Gln Asp Leu Ser
225             230             235             240

Glu Ala Leu Lys Glu Ala Thr Lys Glu Val His Thr Gln Ala Glu Asn
             245             250             255

Ala Glu Phe Met Arg Asn Phe Gln Lys Gly Gln Val Thr Arg Asp Gly
             260             265             270

Phe Lys Leu Val Met Ala Ser Leu Tyr His Ile Tyr Val Ala Leu Glu
             275             280             285

Glu Glu Ile Glu Arg Asn Lys Glu Ser Pro Val Phe Ala Pro Val Tyr
     290             295             300

Phe Pro Glu Glu Leu His Arg Lys Ala Ala Leu Glu Gln Asp Leu Ala
305             310             315             320

Phe Trp Tyr Gly Pro Arg Trp Gln Glu Val Ile Pro Tyr Thr Pro Ala
                 325             330             335

Met Gln Arg Tyr Val Lys Arg Leu His Glu Val Gly Arg Thr Glu Pro
             340             345             350

Glu Leu Leu Val Ala His Ala Tyr Thr Arg Tyr Leu Gly Asp Leu Ser
             355             360             365

Gly Gly Gln Val Leu Lys Lys Ile Ala Gln Lys Ala Leu Asp Leu Pro
     370             375             380

Ser Ser Gly Glu Gly Leu Ala Phe Phe Thr Phe Pro Asn Ile Ala Ser
385             390             395             400

Ala Thr Lys Phe Lys Gln Leu Tyr Arg Ser Arg Met Asn Ser Leu Glu
             405             410             415

Met Thr Pro Ala Val Arg Gln Arg Val Ile Glu Glu Ala Lys Thr Ala
             420             425             430

Phe Leu Leu Asn Ile Gln Leu Phe Glu Glu Leu Gln Glu Leu Leu Thr
             435             440             445

His Asp Thr Lys Asp Gln Ser Pro Ser Arg Ala Pro Gly Leu Arg Gln
     450             455             460

Arg Ala Ser Asn Lys Val Gln Asp Ser Ala Pro Val Glu Thr Pro Arg
465             470             475             480

Gly Lys Pro Pro Leu Asn Thr
                 485
```

```
<210> SEQ ID NO 23
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly
225

<210> SEQ ID NO 24
<211> LENGTH: 488
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Ser Asp Lys Thr His Thr Cys Pro Pro Cys Pro Ala Pro Glu Ala Ala
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
```

```
        50              55              60

Val His Asn Ala Lys Thr Lys Pro Arg Glu Glu Gln Tyr Asn Ser Thr
65              70              75              80

Tyr Arg Val Val Ser Val Leu Thr Val Leu His Gln Asp Trp Leu Asn
            85              90              95

Gly Lys Glu Tyr Lys Cys Lys Val Ser Asn Lys Ala Leu Pro Ala Pro
            100             105             110

Ile Glu Lys Thr Ile Ser Lys Ala Lys Gly Gln Pro Arg Glu Pro Gln
            115             120             125

Val Tyr Thr Leu Pro Pro Ser Arg Asp Glu Leu Thr Lys Asn Gln Val
            130             135             140

Ser Leu Thr Cys Leu Val Lys Gly Phe Tyr Pro Ser Asp Ile Ala Val
145             150             155             160

Glu Trp Glu Ser Asn Gly Gln Pro Glu Asn Asn Tyr Asp Thr Thr Pro
            165             170             175

Pro Val Leu Asp Ser Asp Gly Ser Phe Phe Leu Tyr Ser Asp Leu Thr
            180             185             190

Val Asp Lys Ser Arg Trp Gln Gln Gly Asn Val Phe Ser Cys Ser Val
            195             200             205

Met His Glu Ala Leu His Asn His Tyr Thr Gln Lys Ser Leu Ser Leu
    210             215             220

Ser Pro Gly Met Glu Arg Pro Gln Pro Asp Ser Met Pro Gln Asp Leu
225             230             235             240

Ser Glu Ala Leu Lys Glu Ala Thr Lys Glu Val His Thr Gln Ala Glu
            245             250             255

Asn Ala Glu Phe Met Arg Asn Phe Gln Lys Gly Gln Val Thr Arg Asp
            260             265             270

Gly Phe Lys Leu Val Met Ala Ser Leu Tyr His Ile Tyr Val Ala Leu
            275             280             285

Glu Glu Glu Ile Glu Arg Asn Lys Glu Ser Pro Val Phe Ala Pro Val
    290             295             300

Tyr Phe Pro Glu Glu Leu His Arg Lys Ala Ala Leu Glu Gln Asp Leu
305             310             315             320

Ala Phe Trp Tyr Gly Pro Arg Trp Gln Glu Val Ile Pro Tyr Thr Pro
            325             330             335

Ala Met Gln Arg Tyr Val Lys Arg Leu His Glu Val Gly Arg Thr Glu
            340             345             350

Pro Glu Leu Leu Val Ala His Ala Tyr Thr Arg Tyr Leu Gly Asp Leu
            355             360             365

Ser Gly Gly Gln Val Leu Lys Lys Ile Ala Gln Lys Ala Leu Asp Leu
    370             375             380

Pro Ser Ser Gly Glu Gly Leu Ala Phe Phe Thr Phe Pro Asn Ile Ala
385             390             395             400

Ser Ala Thr Lys Phe Lys Gln Leu Tyr Arg Ser Arg Met Asn Ser Leu
            405             410             415

Glu Met Thr Pro Ala Val Arg Gln Arg Val Ile Glu Glu Ala Lys Thr
            420             425             430

Ala Phe Leu Leu Asn Ile Gln Leu Phe Glu Glu Leu Gln Glu Leu Leu
            435             440             445

Thr His Asp Thr Lys Asp Gln Ser Pro Ser Arg Ala Pro Gly Leu Arg
    450             455             460

Gln Arg Ala Ser Asn Lys Val Gln Asp Ser Ala Pro Val Glu Thr Pro
465             470             475             480
```

-continued

```
Arg Gly Lys Pro Pro Leu Asn Thr
            485

<210> SEQ ID NO 25
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Lys Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Lys Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly
225

<210> SEQ ID NO 26
<211> LENGTH: 487
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30
```

-continued

```
Ile Ser Arg Thr Pro Glu Val Thr Cys Val Val Val Asp Val Ser His
    35              40              45

Glu Asp Pro Glu Val Lys Phe Asn Trp Tyr Val Asp Gly Val Glu Val
50              55              60

His Asn Ala Lys Thr Lys Pro Arg Glu Glu Gln Tyr Asn Ser Thr Tyr
65              70              75              80

Arg Val Val Ser Val Leu Thr Val Leu His Gln Asp Trp Leu Asn Gly
            85              90              95

Lys Glu Tyr Lys Cys Lys Val Ser Asn Lys Ala Leu Pro Ala Pro Ile
        100             105             110

Glu Lys Thr Ile Ser Lys Ala Lys Gly Gln Pro Arg Glu Pro Gln Val
        115             120             125

Cys Thr Leu Pro Pro Ser Arg Asp Glu Leu Thr Glu Asn Gln Val Ser
    130             135             140

Leu Thr Cys Leu Val Lys Gly Phe Tyr Pro Ser Asp Ile Ala Val Glu
145             150             155             160

Trp Glu Ser Asn Gly Gln Pro Glu Asn Asn Tyr Lys Thr Thr Pro Pro
            165             170             175

Val Leu Asp Ser Asp Gly Ser Phe Phe Leu Tyr Ser Trp Leu Thr Val
        180             185             190

Asp Lys Ser Arg Trp Gln Gln Gly Asn Val Phe Ser Cys Ser Val Met
        195             200             205

His Glu Ala Leu His Asn His Tyr Thr Gln Lys Ser Leu Ser Leu Ser
    210             215             220

Pro Gly Met Glu Arg Pro Gln Pro Asp Ser Met Pro Gln Asp Leu Ser
225             230             235             240

Glu Ala Leu Lys Glu Ala Thr Lys Glu Val His Thr Gln Ala Glu Asn
            245             250             255

Ala Glu Phe Met Arg Asn Phe Gln Lys Gly Gln Val Thr Arg Asp Gly
            260             265             270

Phe Lys Leu Val Met Ala Ser Leu Tyr His Ile Tyr Val Ala Leu Glu
        275             280             285

Glu Glu Ile Glu Arg Asn Lys Glu Ser Pro Val Phe Ala Pro Val Tyr
    290             295             300

Phe Pro Glu Glu Leu His Arg Lys Ala Ala Leu Glu Gln Asp Leu Ala
305             310             315             320

Phe Trp Tyr Gly Pro Arg Trp Gln Glu Val Ile Pro Tyr Thr Pro Ala
            325             330             335

Met Gln Arg Tyr Val Lys Arg Leu His Glu Val Gly Arg Thr Glu Pro
        340             345             350

Glu Leu Leu Val Ala His Ala Tyr Thr Arg Tyr Leu Gly Asp Leu Ser
        355             360             365

Gly Gly Gln Val Leu Lys Lys Ile Ala Gln Lys Ala Leu Asp Leu Pro
    370             375             380

Ser Ser Gly Glu Gly Leu Ala Phe Phe Thr Phe Pro Asn Ile Ala Ser
385             390             395             400

Ala Thr Lys Phe Lys Gln Leu Tyr Arg Ser Arg Met Asn Ser Leu Glu
            405             410             415

Met Thr Pro Ala Val Arg Gln Arg Val Ile Glu Glu Ala Lys Thr Ala
        420             425             430

Phe Leu Leu Asn Ile Gln Leu Phe Glu Glu Leu Gln Glu Leu Leu Thr
        435             440             445

His Asp Thr Lys Asp Gln Ser Pro Ser Arg Ala Pro Gly Leu Arg Gln
```

-continued

```
        450             455             460

Arg Ala Ser Asn Lys Val Gln Asp Ser Ala Pro Val Glu Thr Pro Arg
465             470             475             480

Gly Lys Pro Pro Leu Asn Thr
            485
```

<210> SEQ ID NO 27
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

```
Asp Lys Thr His Thr Cys Pro Pro Cys Pro Ala Pro Glu Ala Ala Gly
1               5               10              15

Gly Pro Ser Val Phe Leu Phe Pro Pro Lys Pro Lys Asp Thr Leu Met
            20              25              30

Ile Ser Arg Thr Pro Glu Val Thr Cys Val Val Val Asp Val Ser His
        35              40              45

Glu Asp Pro Glu Val Lys Phe Asn Trp Tyr Val Asp Gly Val Glu Val
    50              55              60

His Asn Ala Lys Thr Lys Pro Arg Glu Glu Gln Tyr Asn Ser Thr Tyr
65              70              75              80

Arg Val Val Ser Val Leu Thr Val Leu His Gln Asp Trp Leu Asn Gly
                85              90              95

Lys Glu Tyr Lys Cys Lys Val Ser Asn Lys Ala Leu Pro Ala Pro Ile
            100             105             110

Glu Lys Thr Ile Ser Lys Ala Lys Gly Gln Pro Arg Glu Pro Arg Val
            115             120             125

Tyr Thr Leu Pro Pro Cys Arg Asp Glu Leu Thr Lys Asn Gln Val Ser
    130             135             140

Leu Thr Cys Leu Val Lys Gly Phe Tyr Pro Ser Asp Ile Ala Val Glu
145             150             155             160

Trp Glu Ser Asn Gly Gln Pro Glu Asn Asn Tyr Lys Thr Thr Pro Pro
            165             170             175

Val Leu Val Ser Asp Gly Ser Phe Thr Leu Tyr Ser Lys Leu Thr Val
            180             185             190

Asp Lys Ser Arg Trp Gln Gln Gly Asn Val Phe Ser Cys Ser Val Met
            195             200             205

His Glu Ala Leu His Asn His Tyr Thr Gln Lys Ser Leu Ser Leu Ser
    210             215             220

Pro Gly
225
```

<210> SEQ ID NO 28
<211> LENGTH: 487
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

```
Met Glu Arg Pro Gln Pro Asp Ser Met Pro Gln Asp Leu Ser Glu Ala
1               5               10              15
```

```
Leu Lys Glu Ala Thr Lys Glu Val His Thr Gln Ala Glu Asn Ala Glu
         20              25              30

Phe Met Arg Asn Phe Gln Lys Gly Gln Val Thr Arg Asp Gly Phe Lys
         35              40              45

Leu Val Met Ala Ser Leu Tyr His Ile Tyr Val Ala Leu Glu Glu Glu
         50              55              60

Ile Glu Arg Asn Lys Glu Ser Pro Val Phe Ala Pro Val Tyr Phe Pro
65              70              75              80

Glu Glu Leu His Arg Lys Ala Ala Leu Glu Gln Asp Leu Ala Phe Trp
                 85              90              95

Tyr Gly Pro Arg Trp Gln Glu Val Ile Pro Tyr Thr Pro Ala Met Gln
             100             105             110

Arg Tyr Val Lys Arg Leu His Glu Val Gly Arg Thr Glu Pro Glu Leu
             115             120             125

Leu Val Ala His Ala Tyr Thr Arg Tyr Leu Gly Asp Leu Ser Gly Gly
         130             135             140

Gln Val Leu Lys Lys Ile Ala Gln Lys Ala Leu Asp Leu Pro Ser Ser
145             150             155             160

Gly Glu Gly Leu Ala Phe Phe Thr Phe Pro Asn Ile Ala Ser Ala Thr
                 165             170             175

Lys Phe Lys Gln Leu Tyr Arg Ser Arg Met Asn Ser Leu Glu Met Thr
             180             185             190

Pro Ala Val Arg Gln Arg Val Ile Glu Glu Ala Lys Thr Ala Phe Leu
             195             200             205

Leu Asn Ile Gln Leu Phe Glu Glu Leu Gln Glu Leu Leu Thr His Asp
         210             215             220

Thr Lys Asp Gln Ser Pro Ser Arg Ala Pro Gly Leu Arg Gln Arg Ala
225             230             235             240

Ser Asn Lys Val Gln Asp Ser Ala Pro Val Glu Thr Pro Arg Gly Lys
             245             250             255

Pro Pro Leu Asn Thr Asp Lys Thr His Thr Cys Pro Pro Cys Pro Ala
             260             265             270

Pro Glu Ala Ala Gly Gly Pro Ser Val Phe Leu Phe Pro Pro Lys Pro
             275             280             285

Lys Asp Thr Leu Met Ile Ser Arg Thr Pro Glu Val Thr Cys Val Val
             290             295             300

Val Asp Val Ser His Glu Asp Pro Glu Val Lys Phe Asn Trp Tyr Val
305             310             315             320

Asp Gly Val Glu Val His Asn Ala Lys Thr Lys Pro Arg Glu Glu Gln
             325             330             335

Tyr Asn Ser Thr Tyr Arg Val Val Ser Val Leu Thr Val Leu His Gln
             340             345             350

Asp Trp Leu Asn Gly Lys Glu Tyr Lys Cys Lys Val Ser Asn Lys Ala
             355             360             365

Leu Pro Ala Pro Ile Glu Lys Thr Ile Ser Lys Ala Lys Gly Gln Pro
         370             375             380

Arg Glu Pro Gln Val Tyr Thr Leu Pro Pro Ser Arg Asp Glu Leu Thr
385             390             395             400

Lys Asn Gln Val Ser Leu Trp Cys Leu Val Lys Gly Phe Tyr Pro Ser
                 405             410             415

Asp Ile Ala Val Glu Trp Glu Ser Asn Gly Gln Pro Glu Asn Asn Tyr
             420             425             430
```

```
Lys Thr Thr Pro Pro Val Leu Asp Ser Asp Gly Ser Phe Phe Leu Tyr
        435             440             445

Ser Lys Leu Thr Val Asp Lys Ser Arg Trp Gln Gln Gly Asn Val Phe
    450             455             460

Ser Cys Ser Val Met His Glu Ala Leu His Asn His Tyr Thr Gln Lys
465             470             475             480

Ser Leu Ser Leu Ser Pro Gly
                485

<210> SEQ ID NO 29
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Asp Lys Thr His Thr Cys Pro Pro Cys Pro Ala Pro Glu Ala Ala Gly
1               5               10              15

Gly Pro Ser Val Phe Leu Phe Pro Pro Lys Pro Lys Asp Thr Leu Met
            20              25              30

Ile Ser Arg Thr Pro Glu Val Thr Cys Val Val Val Asp Val Ser His
        35              40              45

Glu Asp Pro Glu Val Lys Phe Asn Trp Tyr Val Asp Gly Val Glu Val
    50              55              60

His Asn Ala Lys Thr Lys Pro Arg Glu Glu Gln Tyr Asn Ser Thr Tyr
65              70              75              80

Arg Val Val Ser Val Leu Thr Val Leu His Gln Asp Trp Leu Asn Gly
            85              90              95

Lys Glu Tyr Lys Cys Lys Val Ser Asn Lys Ala Leu Pro Ala Pro Ile
            100             105             110

Glu Lys Thr Ile Ser Lys Ala Lys Gly Gln Pro Arg Glu Pro Gln Val
            115             120             125

Tyr Thr Leu Pro Pro Ser Arg Asp Glu Leu Thr Lys Asn Gln Val Ser
    130             135             140

Leu Ser Cys Ala Val Lys Gly Phe Tyr Pro Ser Asp Ile Ala Val Glu
145             150             155             160

Trp Glu Ser Asn Gly Gln Pro Glu Asn Asn Tyr Lys Thr Thr Pro Pro
            165             170             175

Val Leu Asp Ser Asp Gly Ser Phe Phe Leu Val Ser Lys Leu Thr Val
            180             185             190

Asp Lys Ser Arg Trp Gln Gln Gly Asn Val Phe Ser Cys Ser Val Met
    195             200             205

His Glu Ala Leu His Asn His Tyr Thr Gln Lys Ser Leu Ser Leu Ser
    210             215             220

Pro Gly
225

<210> SEQ ID NO 30
<211> LENGTH: 487
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<400> SEQUENCE: 30

Met Glu Arg Pro Gln Pro Asp Ser Met Pro Gln Asp Leu Ser Glu Ala
1               5                   10                  15

Leu Lys Glu Ala Thr Lys Glu Val His Thr Gln Ala Glu Asn Ala Glu
            20                  25                  30

Phe Met Arg Asn Phe Gln Lys Gly Gln Val Thr Arg Asp Gly Phe Lys
        35                  40                  45

Leu Val Met Ala Ser Leu Tyr His Ile Tyr Val Ala Leu Glu Glu Glu
    50                  55                  60

Ile Glu Arg Asn Lys Glu Ser Pro Val Phe Ala Pro Val Tyr Phe Pro
65                  70                  75                  80

Glu Glu Leu His Arg Lys Ala Ala Leu Glu Gln Asp Leu Ala Phe Trp
                85                  90                  95

Tyr Gly Pro Arg Trp Gln Glu Val Ile Pro Tyr Thr Pro Ala Met Gln
            100                 105                 110

Arg Tyr Val Lys Arg Leu His Glu Val Gly Arg Thr Glu Pro Glu Leu
            115                 120                 125

Leu Val Ala His Ala Tyr Thr Arg Tyr Leu Gly Asp Leu Ser Gly Gly
        130                 135                 140

Gln Val Leu Lys Lys Ile Ala Gln Lys Ala Leu Asp Leu Pro Ser Ser
145                 150                 155                 160

Gly Glu Gly Leu Ala Phe Phe Thr Phe Pro Asn Ile Ala Ser Ala Thr
                165                 170                 175

Lys Phe Lys Gln Leu Tyr Arg Ser Arg Met Asn Ser Leu Glu Met Thr
            180                 185                 190

Pro Ala Val Arg Gln Arg Val Ile Glu Glu Ala Lys Thr Ala Phe Leu
            195                 200                 205

Leu Asn Ile Gln Leu Phe Glu Glu Leu Gln Glu Leu Leu Thr His Asp
        210                 215                 220

Thr Lys Asp Gln Ser Pro Ser Arg Ala Pro Gly Leu Arg Gln Arg Ala
225                 230                 235                 240

Ser Asn Lys Val Gln Asp Ser Ala Pro Val Glu Thr Pro Arg Gly Lys
                245                 250                 255

Pro Pro Leu Asn Thr Asp Lys Thr His Thr Cys Pro Pro Cys Pro Ala
            260                 265                 270

Pro Glu Ala Ala Gly Gly Pro Ser Val Phe Leu Phe Pro Pro Lys Pro
            275                 280                 285

Lys Asp Thr Leu Met Ile Ser Arg Thr Pro Glu Val Thr Cys Val Val
        290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
            355                 360                 365

Leu Pro Ala Pro Ile Glu Lys Thr Ile Ser Lys Ala Lys Gly Gln Pro
        370                 375                 380

Arg Glu Pro Gln Val Tyr Thr Leu Pro Pro Ser Arg Asp Glu Leu Thr
385                 390                 395                 400

Glu Asn Gln Val Ser Leu Thr Cys Leu Val Lys Gly Phe Tyr Pro Ser
                405                 410                 415
```

```
Asp Ile Ala Val Glu Trp Glu Ser Asn Gly Gln Pro Glu Asn Asn Tyr
        420             425             430

Lys Thr Thr Pro Pro Val Leu Asp Ser Asp Gly Ser Phe Phe Leu Tyr
        435             440             445

Ser Trp Leu Thr Val Asp Lys Ser Arg Trp Gln Gln Gly Asn Val Phe
    450             455             460

Ser Cys Ser Val Met His Glu Ala Leu His Asn His Tyr Thr Gln Lys
465             470             475             480

Ser Leu Ser Leu Ser Pro Gly
                485
```

```
<210> SEQ ID NO 31
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31
```

```
Asp Lys Thr His Thr Cys Pro Pro Cys Pro Ala Pro Glu Ala Ala Gly
1               5               10              15

Gly Pro Ser Val Phe Leu Phe Pro Pro Lys Pro Lys Asp Thr Leu Met
            20              25              30

Ile Ser Arg Thr Pro Glu Val Thr Cys Val Val Val Asp Val Ser His
        35              40              45

Glu Asp Pro Glu Val Lys Phe Asn Trp Tyr Val Asp Gly Val Glu Val
    50              55              60

His Asn Ala Lys Thr Lys Pro Arg Glu Glu Gln Tyr Asn Ser Thr Tyr
65              70              75              80

Arg Val Val Ser Val Leu Thr Val Leu His Gln Asp Trp Leu Asn Gly
            85              90              95

Lys Glu Tyr Lys Cys Lys Val Ser Asn Lys Ala Leu Pro Ala Pro Ile
            100             105             110

Glu Lys Thr Ile Ser Lys Ala Lys Gly Gln Pro Arg Glu Pro Arg Val
            115             120             125

Tyr Thr Leu Pro Pro Ser Arg Asp Glu Leu Thr Lys Asn Gln Val Ser
    130             135             140

Leu Thr Cys Leu Val Lys Gly Phe Tyr Pro Ser Asp Ile Ala Val Glu
145             150             155             160

Trp Glu Ser Asn Gly Gln Pro Glu Asn Asn Tyr Lys Thr Thr Pro Pro
                165             170             175

Val Leu Val Ser Asp Gly Ser Phe Thr Leu Tyr Ser Lys Leu Thr Val
            180             185             190

Asp Lys Ser Arg Trp Gln Gln Gly Asn Val Phe Ser Cys Ser Val Met
            195             200             205

His Glu Ala Leu His Asn His Tyr Thr Gln Lys Ser Leu Ser Leu Ser
        210             215             220

Pro Gly
225
```

```
<210> SEQ ID NO 32
<211> LENGTH: 452
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"

<400> SEQUENCE: 32

Met Glu Arg Pro Gln Pro Asp Ser Met Pro Gln Asp Leu Ser Glu Ala
1               5                   10                  15

Leu Lys Glu Ala Thr Lys Glu Val His Thr Gln Ala Glu Asn Ala Glu
                20                  25                  30

Phe Met Arg Asn Phe Gln Lys Gly Gln Val Thr Arg Asp Gly Phe Lys
            35                  40                  45

Leu Val Met Ala Ser Leu Tyr His Ile Tyr Val Ala Leu Glu Glu Glu
        50                  55                  60

Ile Glu Arg Asn Lys Glu Ser Pro Val Phe Ala Pro Val Tyr Phe Pro
65                  70                  75                  80

Glu Glu Leu His Arg Lys Ala Ala Leu Glu Gln Asp Leu Ala Phe Trp
                85                  90                  95

Tyr Gly Pro Arg Trp Gln Glu Val Ile Pro Tyr Thr Pro Ala Met Gln
            100                 105                 110

Arg Tyr Val Lys Arg Leu His Glu Val Gly Arg Thr Glu Pro Glu Leu
            115                 120                 125

Leu Val Ala His Ala Tyr Thr Arg Tyr Leu Gly Asp Leu Ser Gly Gly
        130                 135                 140

Gln Val Leu Lys Lys Ile Ala Gln Lys Ala Leu Asp Leu Pro Ser Ser
145                 150                 155                 160

Gly Glu Gly Leu Ala Phe Phe Thr Phe Pro Asn Ile Ala Ser Ala Thr
                165                 170                 175

Lys Phe Lys Gln Leu Tyr Arg Ser Arg Met Asn Ser Leu Glu Met Thr
            180                 185                 190

Pro Ala Val Arg Gln Arg Val Ile Glu Glu Ala Lys Thr Ala Phe Leu
            195                 200                 205

Leu Asn Ile Gln Leu Phe Glu Glu Leu Gln Glu Leu Leu Thr His Asp
        210                 215                 220

Thr Lys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Val Tyr Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
```

```
385                 390                 395                 400

Pro Pro Val Leu Asp Ser Asp Gly Ser Phe Ala Leu Val Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly
        450
```

<210> SEQ ID NO 33
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Val Leu Pro Pro Ser Arg Asp Glu Leu Thr Lys Asn Gln Val Ser
        130                 135                 140

Leu Leu Cys Leu Val Lys Gly Phe Tyr Pro Ser Asp Ile Ala Val Glu
145                 150                 155                 160

Trp Glu Ser Asn Gly Gln Pro Glu Asn Asn Tyr Leu Thr Trp Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly
225
```

<210> SEQ ID NO 34
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic polypeptide"

<400> SEQUENCE: 34

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Met Glu Arg Pro Gln Pro Asp Ser Met Pro Gln Asp Leu Ser
225                 230                 235                 240

Glu Ala Leu Lys Glu Ala Thr Lys Glu Val His Thr Gln Ala Glu Asn
                245                 250                 255

Ala Glu Phe Met Arg Asn Phe Gln Lys Gly Gln Val Thr Arg Asp Gly
                260                 265                 270

Phe Lys Leu Val Met Ala Ser Leu Tyr His Ile Tyr Val Ala Leu Glu
            275                 280                 285

Glu Glu Ile Glu Arg Asn Lys Glu Ser Pro Val Phe Ala Pro Val Tyr
        290                 295                 300

Phe Pro Glu Glu Leu His Arg Lys Ala Ala Leu Glu Gln Asp Leu Ala
305                 310                 315                 320

Phe Trp Tyr Gly Pro Arg Trp Gln Glu Val Ile Pro Tyr Thr Pro Ala
                325                 330                 335

Met Gln Arg Tyr Val Lys Arg Leu His Glu Val Gly Arg Thr Glu Pro
                340                 345                 350

Glu Leu Leu Val Ala His Ala Tyr Thr Arg Tyr Leu Gly Asp Leu Ser
            355                 360                 365

Gly Gly Gln Val Leu Lys Lys Ile Ala Gln Lys Ala Leu Asp Leu Pro
        370                 375                 380

Ser Ser Gly Glu Gly Leu Ala Phe Phe Thr Phe Pro Asn Ile Ala Ser
385                 390                 395                 400
```

-continued

```
Ala Thr Lys Phe Lys Gln Leu Tyr Arg Ser Arg Met Asn Ser Leu Glu
            405                     410                     415

Met Thr Pro Ala Val Arg Gln Arg Val Ile Glu Glu Ala Lys Thr Ala
            420                     425                     430

Phe Leu Leu Asn Ile Gln Leu Phe Glu Glu Leu Gln Glu Leu Leu Thr
            435                     440                     445

His Asp Thr Lys
            450
```

<210> SEQ ID NO 35
<211> LENGTH: 471
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

```
Met Gly Trp Ser Cys Ile Ile Leu Phe Leu Val Ala Thr Ala Thr Gly
1               5                   10                      15

Val His Ser Met Glu Arg Pro Gln Pro Asp Ser Met Pro Gln Asp Leu
            20                      25                      30

Ser Glu Ala Leu Lys Glu Ala Thr Lys Glu Val His Thr Gln Ala Glu
            35                      40                      45

Asn Ala Glu Phe Met Arg Asn Phe Gln Lys Gly Gln Val Thr Arg Asp
    50                      55                      60

Gly Phe Lys Leu Val Met Ala Ser Leu Tyr His Ile Tyr Val Ala Leu
65                      70                      75                      80

Glu Glu Glu Ile Glu Arg Asn Lys Glu Ser Pro Val Phe Ala Pro Val
                85                      90                      95

Tyr Phe Pro Glu Glu Leu His Arg Lys Ala Ala Leu Glu Gln Asp Leu
            100                     105                     110

Ala Phe Trp Tyr Gly Pro Arg Trp Gln Glu Val Ile Pro Tyr Thr Pro
            115                     120                     125

Ala Met Gln Arg Tyr Val Lys Arg Leu His Glu Val Gly Arg Thr Glu
            130                     135                     140

Pro Glu Leu Leu Val Ala His Ala Tyr Thr Arg Tyr Leu Gly Asp Leu
145                     150                     155                     160

Ser Gly Gly Gln Val Leu Lys Lys Ile Ala Gln Lys Ala Leu Asp Leu
            165                     170                     175

Pro Ser Ser Gly Glu Gly Leu Ala Phe Phe Thr Phe Pro Asn Ile Ala
            180                     185                     190

Ser Ala Thr Lys Phe Lys Gln Leu Tyr Arg Ser Arg Met Asn Ser Leu
            195                     200                     205

Glu Met Thr Pro Ala Val Arg Gln Arg Val Ile Glu Glu Ala Lys Thr
            210                     215                     220

Ala Phe Leu Leu Asn Ile Gln Leu Phe Glu Glu Leu Gln Glu Leu Leu
225                     230                     235                     240

Thr His Asp Thr Lys Asp Lys Thr His Thr Cys Pro Pro Cys Pro Ala
            245                     250                     255

Pro Glu Ala Ala Gly Gly Pro Ser Val Phe Leu Phe Pro Pro Lys Pro
            260                     265                     270

Lys Asp Thr Leu Met Ile Ser Arg Thr Pro Glu Val Thr Cys Val Val
            275                     280                     285

Val Asp Val Ser His Glu Asp Pro Glu Val Lys Phe Asn Trp Tyr Val
```

```
       290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
        450                 455                 460

Ser Leu Ser Leu Ser Pro Gly
465                 470

<210> SEQ ID NO 36
<211> LENGTH: 759
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Met Glu Arg Pro Gln Pro Asp Ser Met Pro Gln Asp Leu Ser Glu Ala
1               5                   10                  15

Leu Lys Glu Ala Thr Lys Glu Val His Thr Gln Ala Glu Asn Ala Glu
            20                  25                  30

Phe Met Arg Asn Phe Gln Lys Gly Gln Val Thr Arg Asp Gly Phe Lys
        35                  40                  45

Leu Val Met Ala Ser Leu Tyr His Ile Tyr Val Ala Leu Glu Glu Glu
    50                  55                  60

Ile Glu Arg Asn Lys Glu Ser Pro Val Phe Ala Pro Val Tyr Phe Pro
65                  70                  75                  80

Glu Glu Leu His Arg Lys Ala Ala Leu Glu Gln Asp Leu Ala Phe Trp
                85                  90                  95

Tyr Gly Pro Arg Trp Gln Glu Val Ile Pro Tyr Thr Pro Ala Met Gln
            100                 105                 110

Arg Tyr Val Lys Arg Leu His Glu Val Gly Arg Thr Glu Pro Glu Leu
        115                 120                 125

Leu Val Ala His Ala Tyr Thr Arg Tyr Leu Gly Asp Leu Ser Gly Gly
    130                 135                 140

Gln Val Leu Lys Lys Ile Ala Gln Lys Ala Leu Asp Leu Pro Ser Ser
145                 150                 155                 160

Gly Glu Gly Leu Ala Phe Phe Thr Phe Pro Asn Ile Ala Ser Ala Thr
                165                 170                 175
```

```
Lys Phe Lys Gln Leu Tyr Arg Ser Arg Met Asn Ser Leu Glu Met Thr
        180                 185                 190

Pro Ala Val Arg Gln Arg Val Ile Glu Glu Ala Lys Thr Ala Phe Leu
        195                 200                 205

Leu Asn Ile Gln Leu Phe Glu Glu Leu Gln Glu Leu Leu Thr His Asp
        210                 215                 220

Thr Lys Asp Gln Ser Pro Ser Arg Ala Pro Gly Leu Arg Gln Arg Ala
225                 230                 235                 240

Ser Asn Lys Val Gln Asp Ser Ala Pro Val Glu Thr Pro Arg Gly Lys
                245                 250                 255

Pro Pro Leu Asn Thr Asp Lys Thr His Thr Cys Pro Pro Cys Pro Ala
                260                 265                 270

Pro Glu Ala Ala Gly Gly Pro Ser Val Phe Leu Phe Pro Pro Lys Pro
                275                 280                 285

Lys Asp Thr Leu Met Ile Ser Arg Thr Pro Glu Val Thr Cys Val Val
        290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
                340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
        370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
                420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
        450                 455                 460

Ser Cys Ser Val Met His Glu Ala Leu His Asn His Tyr Thr Gln Lys
465                 470                 475                 480

Ser Leu Ser Leu Ser Pro Gly Gly Gly Gly Ser Gly Gly Gly Gly
                485                 490                 495

Ser Gly Gly Gly Gly Ser Gly Gly Gly Gly Ser Gly Gly Gly Gly Ser
                500                 505                 510

Gly Gly Gly Gly Ser Gly Gly Gly Gly Ser Gly Gly Gly Gly Ser Gly
        515                 520                 525

Glu Pro Lys Ser Ser Asp Lys Thr His Thr Cys Pro Pro Cys Pro Ala
        530                 535                 540

Pro Glu Ala Ala Gly Gly Pro Ser Val Phe Leu Phe Pro Pro Lys Pro
545                 550                 555                 560

Lys Asp Thr Leu Met Ile Ser Arg Thr Pro Glu Val Thr Cys Val Val
                565                 570                 575

Val Asp Val Ser His Glu Asp Pro Glu Val Lys Phe Asn Trp Tyr Val
                580                 585                 590
```

-continued

```
Asp Gly Val Glu Val His Asn Ala Lys Thr Lys Pro Arg Glu Glu Gln
        595                 600                 605

Tyr Asn Ser Thr Tyr Arg Val Val Ser Val Leu Thr Val Leu His Gln
        610                 615                 620

Asp Trp Leu Asn Gly Lys Glu Tyr Lys Cys Lys Val Ser Asn Lys Ala
625                 630                 635                 640

Leu Pro Ala Pro Ile Glu Lys Thr Ile Ser Lys Ala Lys Gly Gln Pro
                645                 650                 655

Arg Glu Pro Gln Val Tyr Thr Leu Pro Pro Ser Arg Asp Glu Leu Thr
                660                 665                 670

Lys Asn Gln Val Ser Leu Thr Cys Leu Val Lys Gly Phe Tyr Pro Ser
        675                 680                 685

Asp Ile Ala Val Glu Trp Glu Ser Asn Gly Gln Pro Glu Asn Asn Tyr
        690                 695                 700

Lys Thr Thr Pro Pro Val Leu Asp Ser Asp Gly Ser Phe Phe Leu Tyr
705                 710                 715                 720

Ser Lys Leu Thr Val Asp Lys Ser Arg Trp Gln Gln Gly Asn Val Phe
                725                 730                 735

Ser Cys Ser Val Met His Glu Ala Leu His Asn His Tyr Thr Gln Lys
                740                 745                 750

Ser Leu Ser Leu Ser Pro Gly
        755
```

```
<210> SEQ ID NO 37
<211> LENGTH: 760
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37
```

```
Met Glu Arg Pro Gln Pro Asp Ser Met Pro Gln Asp Leu Ser Glu Ala
1                   5                   10                  15

Leu Lys Glu Ala Thr Lys Glu Val His Thr Gln Ala Glu Asn Ala Glu
                20                  25                  30

Phe Met Arg Asn Phe Gln Lys Gly Gln Val Thr Arg Asp Gly Phe Lys
        35                  40                  45

Leu Val Met Ala Ser Leu Tyr His Ile Tyr Val Ala Leu Glu Glu Glu
        50                  55                  60

Ile Glu Arg Asn Lys Glu Ser Pro Val Phe Ala Pro Val Tyr Phe Pro
65                  70                  75                  80

Glu Glu Leu His Arg Lys Ala Ala Leu Glu Gln Asp Leu Ala Phe Trp
                85                  90                  95

Tyr Gly Pro Arg Trp Gln Glu Val Ile Pro Tyr Thr Pro Ala Met Gln
                100                 105                 110

Arg Tyr Val Lys Arg Leu His Glu Val Gly Arg Thr Glu Pro Glu Leu
        115                 120                 125

Leu Val Ala His Ala Tyr Thr Arg Tyr Leu Gly Asp Leu Ser Gly Gly
        130                 135                 140

Gln Val Leu Lys Lys Ile Ala Gln Lys Ala Leu Asp Leu Pro Ser Ser
145                 150                 155                 160

Gly Glu Gly Leu Ala Phe Phe Thr Phe Pro Asn Ile Ala Ser Ala Thr
                165                 170                 175

Lys Phe Lys Gln Leu Tyr Arg Ser Arg Met Asn Ser Leu Glu Met Thr
```

-continued

```
               180              185              190
Pro Ala Val Arg Gln Arg Val Ile Glu Glu Ala Lys Thr Ala Phe Leu
        195              200              205

Leu Asn Ile Gln Leu Phe Glu Glu Leu Gln Glu Leu Leu Thr His Asp
        210              215              220

Thr Lys Asp Gln Ser Pro Ser Arg Ala Pro Gly Leu Arg Gln Arg Ala
225              230              235              240

Ser Asn Lys Val Gln Asp Ser Ala Pro Val Glu Thr Pro Arg Gly Lys
            245              250              255

Pro Pro Leu Asn Thr Pro Ala Pro Glu Ala Ala Gly Gly Pro Ser Val
            260              265              270

Phe Leu Phe Pro Pro Lys Pro Lys Asp Thr Leu Met Ile Ser Arg Thr
            275              280              285

Pro Glu Val Thr Cys Val Val Val Asp Val Ser His Glu Asp Pro Glu
            290              295              300

Val Lys Phe Asn Trp Tyr Val Asp Gly Val Glu Val His Asn Ala Lys
305              310              315              320

Thr Lys Pro Arg Glu Glu Gln Tyr Asn Ser Thr Tyr Arg Val Val Ser
            325              330              335

Val Leu Thr Val Leu His Gln Asp Trp Leu Asn Gly Lys Glu Tyr Lys
            340              345              350

Cys Lys Val Ser Asn Lys Ala Leu Pro Ala Pro Ile Glu Lys Thr Ile
            355              360              365

Ser Lys Ala Lys Gly Gln Pro Arg Glu Pro Gln Val Tyr Thr Leu Pro
            370              375              380

Pro Ser Arg Asp Lys Leu Thr Lys Asn Gln Val Ser Leu Thr Cys Leu
385              390              395              400

Val Lys Gly Phe Tyr Pro Ser Asp Ile Ala Val Glu Trp Glu Ser Asn
            405              410              415

Gly Gln Pro Glu Asn Asn Tyr Lys Thr Thr Pro Pro Val Leu Asp Ser
            420              425              430

Asp Gly Ser Phe Phe Leu Tyr Ser Lys Leu Thr Val Asp Lys Ser Arg
            435              440              445

Trp Gln Gln Gly Asn Val Phe Ser Cys Ser Val Met His Glu Ala Leu
            450              455              460

His Asn His Tyr Thr Gln Lys Ser Leu Ser Leu Ser Pro Gly Gly Gly
465              470              475              480

Gly Gly Ser Gly Gly Gly Gly Ser Gly Gly Gly Gly Ser Gly Gly Gly
            485              490              495

Gly Ser Gly Gly Gly Gly Ser Gly Gly Gly Gly Ser Gly Gly Gly Gly
            500              505              510

Ser Gly Gly Gly Gly Ser Gly Gly Gly Gly Ser Gly Gly Gly Gly Ser
            515              520              525

Gly Gly Gly Gly Ser Gly Gly Gly Gly Ser Gly Gly Gly Gly Ser Pro
            530              535              540

Ala Pro Glu Ala Ala Gly Gly Pro Ser Val Phe Leu Phe Pro Pro Lys
545              550              555              560

Pro Lys Asp Thr Leu Met Ile Ser Arg Thr Pro Glu Val Thr Cys Val
            565              570              575

Val Val Asp Val Ser His Glu Asp Pro Glu Val Lys Phe Asn Trp Tyr
            580              585              590

Val Asp Gly Val Glu Val His Asn Ala Lys Thr Lys Pro Arg Glu Glu
            595              600              605
```

```
Gln Tyr Asn Ser Thr Tyr Arg Val Val Ser Val Leu Thr Val Leu His
    610             615             620
```

```
Gln Asp Trp Leu Asn Gly Lys Glu Tyr Lys Cys Lys Val Ser Asn Lys
625             630             635             640
```

```
Ala Leu Pro Ala Pro Ile Glu Lys Thr Ile Ser Lys Ala Lys Gly Gln
            645             650             655
```

```
Pro Arg Glu Pro Gln Val Tyr Thr Leu Pro Pro Ser Arg Asp Glu Leu
            660             665             670
```

```
Thr Lys Asn Gln Val Ser Leu Thr Cys Leu Val Asp Gly Phe Tyr Pro
            675             680             685
```

```
Ser Asp Ile Ala Val Glu Trp Glu Ser Asn Gly Gln Pro Glu Asn Asn
    690             695             700
```

```
Tyr Lys Thr Thr Pro Pro Val Leu Asp Ser Asp Gly Ser Phe Phe Leu
705             710             715             720
```

```
Tyr Ser Lys Leu Thr Val Asp Lys Ser Arg Trp Gln Gln Gly Asn Val
            725             730             735
```

```
Phe Ser Cys Ser Val Met His Glu Ala Leu His Asn His Tyr Thr Gln
            740             745             750
```

```
Lys Ser Leu Ser Leu Ser Pro Gly
        755             760
```

```
<210> SEQ ID NO 38
<211> LENGTH: 724
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<400> SEQUENCE: 38
```

```
Met Glu Arg Pro Gln Pro Asp Ser Met Pro Gln Asp Leu Ser Glu Ala
1               5               10              15
```

```
Leu Lys Glu Ala Thr Lys Glu Val His Thr Gln Ala Glu Asn Ala Glu
            20              25              30
```

```
Phe Met Arg Asn Phe Gln Lys Gly Gln Val Thr Arg Asp Gly Phe Lys
        35              40              45
```

```
Leu Val Met Ala Ser Leu Tyr His Ile Tyr Val Ala Leu Glu Glu Glu
    50              55              60
```

```
Ile Glu Arg Asn Lys Glu Ser Pro Val Phe Ala Pro Val Tyr Phe Pro
65              70              75              80
```

```
Glu Glu Leu His Arg Lys Ala Ala Leu Glu Gln Asp Leu Ala Phe Trp
            85              90              95
```

```
Tyr Gly Pro Arg Trp Gln Glu Val Ile Pro Tyr Thr Pro Ala Met Gln
            100             105             110
```

```
Arg Tyr Val Lys Arg Leu His Glu Val Gly Arg Thr Glu Pro Glu Leu
            115             120             125
```

```
Leu Val Ala His Ala Tyr Thr Arg Tyr Leu Gly Asp Leu Ser Gly Gly
    130             135             140
```

```
Gln Val Leu Lys Lys Ile Ala Gln Lys Ala Leu Asp Leu Pro Ser Ser
145             150             155             160
```

```
Gly Glu Gly Leu Ala Phe Phe Thr Phe Pro Asn Ile Ala Ser Ala Thr
            165             170             175
```

```
Lys Phe Lys Gln Leu Tyr Arg Ser Arg Met Asn Ser Leu Glu Met Thr
            180             185             190
```

Pro Ala Val Arg Gln Arg Val Ile Glu Glu Ala Lys Thr Ala Phe Leu
        195                     200                 205

Leu Asn Ile Gln Leu Phe Glu Glu Leu Gln Glu Leu Leu Thr His Asp
        210                     215                 220

Thr Lys Asp Lys Thr His Thr Cys Pro Pro Cys Pro Ala Pro Glu Ala
225                     230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
        275                     280                 285

Glu Val His Asn Ala Lys Thr Lys Pro Arg Glu Glu Gln Tyr Asn Ser
        290                     295                 300

Thr Tyr Arg Val Val Ser Val Leu Thr Val Leu His Gln Asp Trp Leu
305                     310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
                355                 360                 365

Val Ser Leu Thr Cys Leu Val Lys Gly Phe Tyr Pro Ser Asp Ile Ala
        370                     375                 380

Val Glu Trp Glu Ser Asn Gly Gln Pro Glu Asn Asn Tyr Lys Thr Thr
385                     390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
        435                     440                 445

Leu Ser Pro Gly Gly Gly Gly Ser Gly Gly Gly Gly Ser Gly Gly
        450                     455                 460

Gly Gly Ser Gly Gly Gly Gly Ser Gly Gly Gly Gly Ser Gly Gly Gly
465                     470                 475                 480

Gly Ser Gly Gly Gly Gly Ser Gly Gly Gly Gly Ser Gly Glu Pro Lys
                485                 490                 495

Ser Ser Asp Lys Thr His Thr Cys Pro Pro Cys Pro Ala Pro Glu Ala
                500                 505                 510

Ala Gly Gly Pro Ser Val Phe Leu Phe Pro Pro Lys Pro Lys Asp Thr
                515                 520                 525

Leu Met Ile Ser Arg Thr Pro Glu Val Thr Cys Val Val Val Asp Val
        530                     535                 540

Ser His Glu Asp Pro Glu Val Lys Phe Asn Trp Tyr Val Asp Gly Val
545                     550                 555                 560

Glu Val His Asn Ala Lys Thr Lys Pro Arg Glu Glu Gln Tyr Asn Ser
                565                 570                 575

Thr Tyr Arg Val Val Ser Val Leu Thr Val Leu His Gln Asp Trp Leu
                580                 585                 590

Asn Gly Lys Glu Tyr Lys Cys Lys Val Ser Asn Lys Ala Leu Pro Ala
                595                 600                 605

Pro Ile Glu Lys Thr Ile Ser Lys Ala Lys Gly Gln Pro Arg Glu Pro

```
                    610                 615                 620

Gln Val Tyr Thr Leu Pro Pro Ser Arg Asp Glu Leu Thr Lys Asn Gln
625                 630                 635                 640

Val Ser Leu Thr Cys Leu Val Lys Gly Phe Tyr Pro Ser Asp Ile Ala
                645                 650                 655

Val Glu Trp Glu Ser Asn Gly Gln Pro Glu Asn Asn Tyr Lys Thr Thr
                660                 665                 670

Pro Pro Val Leu Asp Ser Asp Gly Ser Phe Phe Leu Tyr Ser Lys Leu
                675                 680                 685

Thr Val Asp Lys Ser Arg Trp Gln Gln Gly Asn Val Phe Ser Cys Ser
                690                 695                 700

Val Met His Glu Ala Leu His Asn His Tyr Thr Gln Lys Ser Leu Ser
705                 710                 715                 720

Leu Ser Pro Gly

<210> SEQ ID NO 39
<211> LENGTH: 725
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Met Glu Arg Pro Gln Pro Asp Ser Met Pro Gln Asp Leu Ser Glu Ala
1               5                   10                  15

Leu Lys Glu Ala Thr Lys Glu Val His Thr Gln Ala Glu Asn Ala Glu
                20                  25                  30

Phe Met Arg Asn Phe Gln Lys Gly Gln Val Thr Arg Asp Gly Phe Lys
            35                  40                  45

Leu Val Met Ala Ser Leu Tyr His Ile Tyr Val Ala Leu Glu Glu Glu
        50                  55                  60

Ile Glu Arg Asn Lys Glu Ser Pro Val Phe Ala Pro Val Tyr Phe Pro
65                  70                  75                  80

Glu Glu Leu His Arg Lys Ala Ala Leu Glu Gln Asp Leu Ala Phe Trp
                85                  90                  95

Tyr Gly Pro Arg Trp Gln Glu Val Ile Pro Tyr Thr Pro Ala Met Gln
            100                 105                 110

Arg Tyr Val Lys Arg Leu His Glu Val Gly Arg Thr Glu Pro Glu Leu
        115                 120                 125

Leu Val Ala His Ala Tyr Thr Arg Tyr Leu Gly Asp Leu Ser Gly Gly
        130                 135                 140

Gln Val Leu Lys Lys Ile Ala Gln Lys Ala Leu Asp Leu Pro Ser Ser
145                 150                 155                 160

Gly Glu Gly Leu Ala Phe Phe Thr Phe Pro Asn Ile Ala Ser Ala Thr
                165                 170                 175

Lys Phe Lys Gln Leu Tyr Arg Ser Arg Met Asn Ser Leu Glu Met Thr
                180                 185                 190

Pro Ala Val Arg Gln Arg Val Ile Glu Glu Ala Lys Thr Ala Phe Leu
            195                 200                 205

Leu Asn Ile Gln Leu Phe Glu Glu Leu Gln Glu Leu Leu Thr His Asp
        210                 215                 220

Thr Lys Pro Ala Pro Glu Ala Ala Gly Gly Pro Ser Val Phe Leu Phe
225                 230                 235                 240
```

-continued

```
Pro Pro Lys Pro Lys Asp Thr Leu Met Ile Ser Arg Thr Pro Glu Val
            245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Lys Leu Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Gly Gly Gly Gly Ser
            435                 440                 445

Gly Gly Gly Gly Ser Gly Gly Gly Gly Ser Gly Gly Gly Gly Ser Gly
    450                 455                 460

Gly Gly Gly Ser Gly Gly Gly Gly Ser Gly Gly Gly Gly Ser Gly Gly
465                 470                 475                 480

Gly Gly Ser Gly Gly Gly Gly Ser Gly Gly Gly Gly Ser Gly Gly Gly
                485                 490                 495

Gly Ser Gly Gly Gly Gly Ser Gly Gly Gly Gly Ser Pro Ala Pro Glu
            500                 505                 510

Ala Ala Gly Gly Pro Ser Val Phe Leu Phe Pro Pro Lys Pro Lys Asp
            515                 520                 525

Thr Leu Met Ile Ser Arg Thr Pro Glu Val Thr Cys Val Val Val Asp
            530                 535                 540

Val Ser His Glu Asp Pro Glu Val Lys Phe Asn Trp Tyr Val Asp Gly
545                 550                 555                 560

Val Glu Val His Asn Ala Lys Thr Lys Pro Arg Glu Glu Gln Tyr Asn
                565                 570                 575

Ser Thr Tyr Arg Val Val Ser Val Leu Thr Val Leu His Gln Asp Trp
            580                 585                 590

Leu Asn Gly Lys Glu Tyr Lys Cys Lys Val Ser Asn Lys Ala Leu Pro
            595                 600                 605

Ala Pro Ile Glu Lys Thr Ile Ser Lys Ala Lys Gly Gln Pro Arg Glu
    610                 615                 620

Pro Gln Val Tyr Thr Leu Pro Pro Ser Arg Asp Glu Leu Thr Lys Asn
625                 630                 635                 640

Gln Val Ser Leu Thr Cys Leu Val Asp Gly Phe Tyr Pro Ser Asp Ile
                645                 650                 655

Ala Val Glu Trp Glu Ser Asn Gly Gln Pro Glu Asn Asn Tyr Lys Thr
```

-continued

```
                 660                 665                 670

Thr Pro Pro Val Leu Asp Ser Asp Gly Ser Phe Phe Leu Tyr Ser Lys
             675                 680                 685

Leu Thr Val Asp Lys Ser Arg Trp Gln Gln Gly Asn Val Phe Ser Cys
         690                 695                 700

Ser Val Met His Glu Ala Leu His Asn His Tyr Thr Gln Lys Ser Leu
705                 710                 715                 720

Ser Leu Ser Pro Gly
                725

<210> SEQ ID NO 40
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Pro Leu Leu Arg Trp Val Leu Thr Leu Ser Phe Leu Val Ala Thr Val
1               5                   10                  15

Ala Val Gly Leu Tyr Ala Met
            20

<210> SEQ ID NO 41
<211> LENGTH: 508
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Met Glu Thr Pro Ala Gln Leu Leu Phe Leu Leu Leu Leu Trp Leu Pro
1               5                   10                  15

Asp Thr Thr Gly Met Glu Arg Pro Gln Pro Asp Ser Met Pro Gln Asp
                20                  25                  30

Leu Ser Glu Ala Leu Lys Glu Ala Thr Lys Glu Val His Thr Gln Ala
         35                  40                  45

Glu Asn Ala Glu Phe Met Arg Asn Phe Gln Lys Gly Gln Val Thr Arg
     50                  55                  60

Asp Gly Phe Lys Leu Val Met Ala Ser Leu Tyr His Ile Tyr Val Ala
65                  70                  75                  80

Leu Glu Glu Glu Ile Glu Arg Asn Lys Glu Ser Pro Val Phe Ala Pro
                85                  90                  95

Val Tyr Phe Pro Glu Glu Leu His Arg Lys Ala Ala Leu Glu Gln Asp
            100                 105                 110

Leu Ala Phe Trp Tyr Gly Pro Arg Trp Gln Glu Val Ile Pro Tyr Thr
         115                 120                 125

Pro Ala Met Gln Arg Tyr Val Lys Arg Leu His Glu Val Gly Arg Thr
     130                 135                 140

Glu Pro Glu Leu Leu Val Ala His Ala Tyr Thr Arg Tyr Leu Gly Asp
145                 150                 155                 160

Leu Ser Gly Gly Gln Val Leu Lys Lys Ile Ala Gln Lys Ala Leu Asp
                165                 170                 175

Leu Pro Ser Ser Gly Glu Gly Leu Ala Phe Phe Thr Phe Pro Asn Ile
            180                 185                 190
```

```
Ala Ser Ala Thr Lys Phe Lys Gln Leu Tyr Arg Ser Arg Met Asn Ser
        195                 200                 205

Leu Glu Met Thr Pro Ala Val Arg Gln Arg Val Ile Glu Glu Ala Lys
    210                 215                 220

Thr Ala Phe Leu Leu Asn Ile Gln Leu Phe Glu Glu Leu Gln Glu Leu
225                 230                 235                 240

Leu Thr His Asp Thr Lys Asp Gln Ser Pro Ser Arg Ala Pro Gly Leu
                245                 250                 255

Arg Gln Arg Ala Ser Asn Lys Val Gln Asp Ser Ala Pro Val Glu Thr
                260                 265                 270

Pro Arg Gly Lys Pro Pro Leu Asn Thr Asp Lys Thr His Thr Cys Pro
                275                 280                 285

Pro Cys Pro Ala Pro Glu Ala Ala Gly Gly Pro Ser Val Phe Leu Phe
    290                 295                 300

Pro Pro Lys Pro Lys Asp Thr Leu Met Ile Ser Arg Thr Pro Glu Val
305                 310                 315                 320

Thr Cys Val Val Val Asp Val Ser His Glu Asp Pro Glu Val Lys Phe
                325                 330                 335

Asn Trp Tyr Val Asp Gly Val Glu Val His Asn Ala Lys Thr Lys Pro
                340                 345                 350

Arg Glu Glu Gln Tyr Asn Ser Thr Tyr Arg Val Val Ser Val Leu Thr
                355                 360                 365

Val Leu His Gln Asp Trp Leu Asn Gly Lys Glu Tyr Lys Cys Lys Val
    370                 375                 380

Ser Asn Lys Ala Leu Pro Ala Pro Ile Glu Lys Thr Ile Ser Lys Ala
385                 390                 395                 400

Lys Gly Gln Pro Arg Glu Pro Gln Val Tyr Val Tyr Pro Pro Ser Arg
                405                 410                 415

Asp Glu Leu Thr Lys Asn Gln Val Ser Leu Thr Cys Leu Val Lys Gly
                420                 425                 430

Phe Tyr Pro Ser Asp Ile Ala Val Glu Trp Glu Ser Asn Gly Gln Pro
                435                 440                 445

Glu Asn Asn Tyr Lys Thr Thr Pro Pro Val Leu Asp Ser Asp Gly Ser
    450                 455                 460

Phe Ala Leu Val Ser Lys Leu Thr Val Asp Lys Ser Arg Trp Gln Gln
465                 470                 475                 480

Gly Asn Val Phe Ser Cys Ser Val Met His Glu Ala Leu His Asn His
                485                 490                 495

Tyr Thr Gln Lys Ser Leu Ser Leu Ser Pro Gly Lys
                500                 505
```

```
<210> SEQ ID NO 42
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Met Glu Thr Pro Ala Gln Leu Leu Phe Leu Leu Leu Trp Leu Pro
1               5                   10                  15

Asp Thr Thr Gly Asp Lys Thr His Thr Cys Pro Pro Cys Pro Ala Pro
            20                  25                  30
```

```
Glu Ala Ala Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
                100                 105                 110

Trp Leu Asn Gly Lys Glu Tyr Lys Cys Lys Val Ser Asn Lys Ala Leu
            115                 120                 125

Pro Ala Pro Ile Glu Lys Thr Ile Ser Lys Ala Lys Gly Gln Pro Arg
        130                 135                 140

Glu Pro Gln Val Tyr Val Leu Pro Pro Ser Arg Asp Glu Leu Thr Lys
145                 150                 155                 160

Asn Gln Val Ser Leu Leu Cys Leu Val Lys Gly Phe Tyr Pro Ser Asp
                165                 170                 175

Ile Ala Val Glu Trp Glu Ser Asn Gly Gln Pro Glu Asn Asn Tyr Leu
                180                 185                 190

Thr Trp Pro Pro Val Leu Asp Ser Asp Gly Ser Phe Phe Leu Tyr Ser
            195                 200                 205

Lys Leu Thr Val Asp Lys Ser Arg Trp Gln Gln Gly Asn Val Phe Ser
        210                 215                 220

Cys Ser Val Met His Glu Ala Leu His Asn His Tyr Thr Gln Lys Ser
225                 230                 235                 240

Leu Ser Leu Ser Pro Gly Lys
                245
```

```
<210> SEQ ID NO 43
<211> LENGTH: 506
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43
```

```
Met Gly Trp Ser Cys Ile Ile Leu Phe Leu Val Ala Thr Ala Thr Gly
1               5                   10                  15

Val His Ser Asp Lys Thr His Thr Cys Pro Pro Cys Pro Ala Pro Glu
            20                  25                  30

Ala Ala Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
                100                 105                 110

Leu Asn Gly Lys Glu Tyr Lys Cys Lys Val Ser Asn Lys Ala Leu Pro
            115                 120                 125

Ala Pro Ile Glu Lys Thr Ile Ser Lys Ala Lys Gly Gln Pro Arg Glu
```

-continued

```
          130                 135                 140
Pro Gln Val Tyr Thr Leu Pro Pro Cys Arg Asp Glu Leu Thr Lys Asn
145                 150                 155                 160

Gln Val Ser Leu Trp Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
                180                 185                 190

Thr Pro Pro Val Leu Asp Ser Asp Gly Ser Phe Phe Leu Tyr Ser Lys
                195                 200                 205

Leu Thr Val Asp Lys Ser Arg Trp Gln Gln Gly Asn Val Phe Ser Cys
            210                 215                 220

Ser Val Met His Glu Ala Leu His Asn His Tyr Thr Gln Lys Ser Leu
225                 230                 235                 240

Ser Leu Ser Pro Gly Met Glu Arg Pro Gln Pro Asp Ser Met Pro Gln
                245                 250                 255

Asp Leu Ser Glu Ala Leu Lys Glu Ala Thr Lys Glu Val His Thr Gln
                260                 265                 270

Ala Glu Asn Ala Glu Phe Met Arg Asn Phe Gln Lys Gly Gln Val Thr
                275                 280                 285

Arg Asp Gly Phe Lys Leu Val Met Ala Ser Leu Tyr His Ile Tyr Val
    290                 295                 300

Ala Leu Glu Glu Glu Ile Glu Arg Asn Lys Glu Ser Pro Val Phe Ala
305                 310                 315                 320

Pro Val Tyr Phe Pro Glu Glu Leu His Arg Lys Ala Ala Leu Glu Gln
                325                 330                 335

Asp Leu Ala Phe Trp Tyr Gly Pro Arg Trp Gln Glu Val Ile Pro Tyr
                340                 345                 350

Thr Pro Ala Met Gln Arg Tyr Val Lys Arg Leu His Glu Val Gly Arg
                355                 360                 365

Thr Glu Pro Glu Leu Leu Val Ala His Ala Tyr Thr Arg Tyr Leu Gly
    370                 375                 380

Asp Leu Ser Gly Gly Gln Val Leu Lys Lys Ile Ala Gln Lys Ala Leu
385                 390                 395                 400

Asp Leu Pro Ser Ser Gly Glu Gly Leu Ala Phe Phe Thr Phe Pro Asn
                405                 410                 415

Ile Ala Ser Ala Thr Lys Phe Lys Gln Leu Tyr Arg Ser Arg Met Asn
                420                 425                 430

Ser Leu Glu Met Thr Pro Ala Val Arg Gln Arg Val Ile Glu Glu Ala
                435                 440                 445

Lys Thr Ala Phe Leu Leu Asn Ile Gln Leu Phe Glu Glu Leu Gln Glu
    450                 455                 460

Leu Leu Thr His Asp Thr Lys Asp Gln Ser Pro Ser Arg Ala Pro Gly
465                 470                 475                 480

Leu Arg Gln Arg Ala Ser Asn Lys Val Gln Asp Ser Ala Pro Val Glu
                485                 490                 495

Thr Pro Arg Gly Lys Pro Pro Leu Asn Thr
                500                 505
```

```
<210> SEQ ID NO 44
<211> LENGTH: 245
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 44

```
Met Gly Trp Ser Cys Ile Ile Leu Phe Leu Val Ala Thr Ala Thr Gly
1               5                   10                  15

Val His Ser Asp Lys Thr His Thr Cys Pro Pro Cys Pro Ala Pro Glu
                20                  25                  30

Ala Ala Gly Gly Pro Ser Val Phe Leu Phe Pro Pro Lys Pro Lys Asp
            35                  40                  45

Thr Leu Met Ile Ser Arg Thr Pro Glu Val Thr Cys Val Val Val Asp
        50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
                100                 105                 110

Leu Asn Gly Lys Glu Tyr Lys Cys Lys Val Ser Asn Lys Ala Leu Pro
            115                 120                 125

Ala Pro Ile Glu Lys Thr Ile Ser Lys Ala Lys Gly Gln Pro Arg Glu
        130                 135                 140

Pro Gln Val Cys Thr Leu Pro Pro Ser Arg Asp Glu Leu Thr Lys Asn
145                 150                 155                 160

Gln Val Ser Leu Ser Cys Ala Val Lys Gly Phe Tyr Pro Ser Asp Ile
                165                 170                 175

Ala Val Glu Trp Glu Ser Asn Gly Gln Pro Glu Asn Asn Tyr Lys Thr
                180                 185                 190

Thr Pro Pro Val Leu Asp Ser Asp Gly Ser Phe Phe Leu Val Ser Lys
            195                 200                 205

Leu Thr Val Asp Lys Ser Arg Trp Gln Gln Gly Asn Val Phe Ser Cys
        210                 215                 220

Ser Val Met His Glu Ala Leu His Asn His Tyr Thr Gln Lys Ser Leu
225                 230                 235                 240

Ser Leu Ser Pro Gly
                245
```

```
<210> SEQ ID NO 45
<211> LENGTH: 506
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 45

```
Met Gly Trp Ser Cys Ile Ile Leu Phe Leu Val Ala Thr Ala Thr Gly
1               5                   10                  15

Val His Ser Asp Lys Thr His Thr Cys Pro Pro Cys Pro Ala Pro Glu
                20                  25                  30

Ala Ala Gly Gly Pro Ser Val Phe Leu Phe Pro Pro Lys Pro Lys Asp
            35                  40                  45

Thr Leu Met Ile Ser Arg Thr Pro Glu Val Thr Cys Val Val Val Asp
        50                  55                  60

Val Ser His Glu Asp Pro Glu Val Lys Phe Asn Trp Tyr Val Asp Gly
65                  70                  75                  80
```

-continued

```
Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Asp Thr
            180                 185                 190

Thr Pro Pro Val Leu Asp Ser Asp Gly Ser Phe Phe Leu Tyr Ser Asp
            195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Met Glu Arg Pro Gln Pro Asp Ser Met Pro Gln
            245                 250                 255

Asp Leu Ser Glu Ala Leu Lys Glu Ala Thr Lys Glu Val His Thr Gln
            260                 265                 270

Ala Glu Asn Ala Glu Phe Met Arg Asn Phe Gln Lys Gly Gln Val Thr
            275                 280                 285

Arg Asp Gly Phe Lys Leu Val Met Ala Ser Leu Tyr His Ile Tyr Val
    290                 295                 300

Ala Leu Glu Glu Glu Ile Glu Arg Asn Lys Glu Ser Pro Val Phe Ala
305                 310                 315                 320

Pro Val Tyr Phe Pro Glu Glu Leu His Arg Lys Ala Ala Leu Glu Gln
            325                 330                 335

Asp Leu Ala Phe Trp Tyr Gly Pro Arg Trp Gln Glu Val Ile Pro Tyr
            340                 345                 350

Thr Pro Ala Met Gln Arg Tyr Val Lys Arg Leu His Glu Val Gly Arg
            355                 360                 365

Thr Glu Pro Glu Leu Leu Val Ala His Ala Tyr Thr Arg Tyr Leu Gly
    370                 375                 380

Asp Leu Ser Gly Gly Gln Val Leu Lys Lys Ile Ala Gln Lys Ala Leu
385                 390                 395                 400

Asp Leu Pro Ser Ser Gly Glu Gly Leu Ala Phe Phe Thr Phe Pro Asn
            405                 410                 415

Ile Ala Ser Ala Thr Lys Phe Lys Gln Leu Tyr Arg Ser Arg Met Asn
            420                 425                 430

Ser Leu Glu Met Thr Pro Ala Val Arg Gln Arg Val Ile Glu Glu Ala
            435                 440                 445

Lys Thr Ala Phe Leu Leu Asn Ile Gln Leu Phe Glu Glu Leu Gln Glu
    450                 455                 460

Leu Leu Thr His Asp Thr Lys Asp Gln Ser Pro Ser Arg Ala Pro Gly
465                 470                 475                 480

Leu Arg Gln Arg Ala Ser Asn Lys Val Gln Asp Ser Ala Pro Val Glu
            485                 490                 495

Thr Pro Arg Gly Lys Pro Pro Leu Asn Thr
```

-continued

```
                500                 505

<210> SEQ ID NO 46
<211> LENGTH: 245
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Met Gly Trp Ser Cys Ile Ile Leu Phe Leu Val Ala Thr Ala Thr Gly
1               5                   10                  15

Val His Ser Asp Lys Thr His Thr Cys Pro Pro Cys Pro Ala Pro Glu
            20                  25                  30

Ala Ala Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Lys Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Lys Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly
                245

<210> SEQ ID NO 47
<211> LENGTH: 506
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Met Gly Trp Ser Cys Ile Ile Leu Phe Leu Val Ala Thr Ala Thr Gly
1               5                   10                  15

Val His Ser Asp Lys Thr His Thr Cys Pro Pro Cys Pro Ala Pro Glu
            20                  25                  30
```

-continued

```
Ala Ala Gly Gly Pro Ser Val Phe Leu Phe Pro Pro Lys Pro Lys Asp
        35              40              45

Thr Leu Met Ile Ser Arg Thr Pro Glu Val Thr Cys Val Val Val Asp
        50              55              60

Val Ser His Glu Asp Pro Glu Val Lys Phe Asn Trp Tyr Val Asp Gly
65              70              75              80

Val Glu Val His Asn Ala Lys Thr Lys Pro Arg Glu Glu Gln Tyr Asn
        85              90              95

Ser Thr Tyr Arg Val Val Ser Val Leu Thr Val Leu His Gln Asp Trp
        100             105             110

Leu Asn Gly Lys Glu Tyr Lys Cys Lys Val Ser Asn Lys Ala Leu Pro
        115             120             125

Ala Pro Ile Glu Lys Thr Ile Ser Lys Ala Lys Gly Gln Pro Arg Glu
        130             135             140

Pro Gln Val Cys Thr Leu Pro Pro Ser Arg Asp Glu Leu Thr Glu Asn
145             150             155             160

Gln Val Ser Leu Thr Cys Leu Val Lys Gly Phe Tyr Pro Ser Asp Ile
        165             170             175

Ala Val Glu Trp Glu Ser Asn Gly Gln Pro Glu Asn Asn Tyr Lys Thr
        180             185             190

Thr Pro Pro Val Leu Asp Ser Asp Gly Ser Phe Phe Leu Tyr Ser Trp
        195             200             205

Leu Thr Val Asp Lys Ser Arg Trp Gln Gln Gly Asn Val Phe Ser Cys
        210             215             220

Ser Val Met His Glu Ala Leu His Asn His Tyr Thr Gln Lys Ser Leu
225             230             235             240

Ser Leu Ser Pro Gly Met Glu Arg Pro Gln Pro Asp Ser Met Pro Gln
        245             250             255

Asp Leu Ser Glu Ala Leu Lys Glu Ala Thr Lys Glu Val His Thr Gln
        260             265             270

Ala Glu Asn Ala Glu Phe Met Arg Asn Phe Gln Lys Gly Gln Val Thr
        275             280             285

Arg Asp Gly Phe Lys Leu Val Met Ala Ser Leu Tyr His Ile Tyr Val
        290             295             300

Ala Leu Glu Glu Glu Ile Glu Arg Asn Lys Glu Ser Pro Val Phe Ala
305             310             315             320

Pro Val Tyr Phe Pro Glu Glu Leu His Arg Lys Ala Ala Leu Glu Gln
        325             330             335

Asp Leu Ala Phe Trp Tyr Gly Pro Arg Trp Gln Glu Val Ile Pro Tyr
        340             345             350

Thr Pro Ala Met Gln Arg Tyr Val Lys Arg Leu His Glu Val Gly Arg
        355             360             365

Thr Glu Pro Glu Leu Leu Val Ala His Ala Tyr Thr Arg Tyr Leu Gly
        370             375             380

Asp Leu Ser Gly Gly Gln Val Leu Lys Lys Ile Ala Gln Lys Ala Leu
385             390             395             400

Asp Leu Pro Ser Ser Gly Glu Gly Leu Ala Phe Phe Thr Phe Pro Asn
        405             410             415

Ile Ala Ser Ala Thr Lys Phe Lys Gln Leu Tyr Arg Ser Arg Met Asn
        420             425             430

Ser Leu Glu Met Thr Pro Ala Val Arg Gln Arg Val Ile Glu Glu Ala
        435             440             445
```

```
Lys Thr Ala Phe Leu Leu Asn Ile Gln Leu Phe Glu Glu Leu Gln Glu
    450             455             460

Leu Leu Thr His Asp Thr Lys Asp Gln Ser Pro Ser Arg Ala Pro Gly
465             470             475             480

Leu Arg Gln Arg Ala Ser Asn Lys Val Gln Asp Ser Ala Pro Val Glu
            485             490             495

Thr Pro Arg Gly Lys Pro Pro Leu Asn Thr
            500             505
```

```
<210> SEQ ID NO 48
<211> LENGTH: 245
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48
```

```
Met Gly Trp Ser Cys Ile Ile Leu Phe Leu Val Ala Thr Ala Thr Gly
1               5               10              15

Val His Ser Asp Lys Thr His Thr Cys Pro Pro Cys Pro Ala Pro Glu
            20              25              30

Ala Ala Gly Gly Pro Ser Val Phe Leu Phe Pro Pro Lys Pro Lys Asp
        35              40              45

Thr Leu Met Ile Ser Arg Thr Pro Glu Val Thr Cys Val Val Val Asp
    50              55              60

Val Ser His Glu Asp Pro Glu Val Lys Phe Asn Trp Tyr Val Asp Gly
65              70              75              80

Val Glu Val His Asn Ala Lys Thr Lys Pro Arg Glu Glu Gln Tyr Asn
            85              90              95

Ser Thr Tyr Arg Val Val Ser Val Leu Thr Val Leu His Gln Asp Trp
            100             105             110

Leu Asn Gly Lys Glu Tyr Lys Cys Lys Val Ser Asn Lys Ala Leu Pro
            115             120             125

Ala Pro Ile Glu Lys Thr Ile Ser Lys Ala Lys Gly Gln Pro Arg Glu
    130             135             140

Pro Arg Val Tyr Thr Leu Pro Pro Cys Arg Asp Glu Leu Thr Lys Asn
145             150             155             160

Gln Val Ser Leu Thr Cys Leu Val Lys Gly Phe Tyr Pro Ser Asp Ile
            165             170             175

Ala Val Glu Trp Glu Ser Asn Gly Gln Pro Glu Asn Asn Tyr Lys Thr
            180             185             190

Thr Pro Pro Val Leu Val Ser Asp Gly Ser Phe Thr Leu Tyr Ser Lys
            195             200             205

Leu Thr Val Asp Lys Ser Arg Trp Gln Gln Gly Asn Val Phe Ser Cys
    210             215             220

Ser Val Met His Glu Ala Leu His Asn His Tyr Thr Gln Lys Ser Leu
225             230             235             240

Ser Leu Ser Pro Gly
            245
```

```
<210> SEQ ID NO 49
<211> LENGTH: 506
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"

<400> SEQUENCE: 49

```
Met Gly Trp Ser Cys Ile Ile Leu Phe Leu Val Ala Thr Ala Thr Gly
1               5                   10                  15

Val His Ser Met Glu Arg Pro Gln Pro Asp Ser Met Pro Gln Asp Leu
            20                  25                  30

Ser Glu Ala Leu Lys Glu Ala Thr Lys Glu Val His Thr Gln Ala Glu
        35                  40                  45

Asn Ala Glu Phe Met Arg Asn Phe Gln Lys Gly Gln Val Thr Arg Asp
    50                  55                  60

Gly Phe Lys Leu Val Met Ala Ser Leu Tyr His Ile Tyr Val Ala Leu
65                  70                  75                  80

Glu Glu Glu Ile Glu Arg Asn Lys Glu Ser Pro Val Phe Ala Pro Val
                85                  90                  95

Tyr Phe Pro Glu Glu Leu His Arg Lys Ala Ala Leu Glu Gln Asp Leu
            100                 105                 110

Ala Phe Trp Tyr Gly Pro Arg Trp Gln Glu Val Ile Pro Tyr Thr Pro
            115                 120                 125

Ala Met Gln Arg Tyr Val Lys Arg Leu His Glu Val Gly Arg Thr Glu
        130                 135                 140

Pro Glu Leu Leu Val Ala His Ala Tyr Thr Arg Tyr Leu Gly Asp Leu
145                 150                 155                 160

Ser Gly Gly Gln Val Leu Lys Lys Ile Ala Gln Lys Ala Leu Asp Leu
                165                 170                 175

Pro Ser Ser Gly Glu Gly Leu Ala Phe Phe Thr Phe Pro Asn Ile Ala
            180                 185                 190

Ser Ala Thr Lys Phe Lys Gln Leu Tyr Arg Ser Arg Met Asn Ser Leu
        195                 200                 205

Glu Met Thr Pro Ala Val Arg Gln Arg Val Ile Glu Glu Ala Lys Thr
    210                 215                 220

Ala Phe Leu Leu Asn Ile Gln Leu Phe Glu Glu Leu Gln Glu Leu Leu
225                 230                 235                 240

Thr His Asp Thr Lys Asp Gln Ser Pro Ser Arg Ala Pro Gly Leu Arg
                245                 250                 255

Gln Arg Ala Ser Asn Lys Val Gln Asp Ser Ala Pro Val Glu Thr Pro
            260                 265                 270

Arg Gly Lys Pro Pro Leu Asn Thr Asp Lys Thr His Thr Cys Pro Pro
            275                 280                 285

Cys Pro Ala Pro Glu Ala Ala Gly Gly Pro Ser Val Phe Leu Phe Pro
    290                 295                 300

Pro Lys Pro Lys Asp Thr Leu Met Ile Ser Arg Thr Pro Glu Val Thr
305                 310                 315                 320

Cys Val Val Val Asp Val Ser His Glu Asp Pro Glu Val Lys Phe Asn
                325                 330                 335

Trp Tyr Val Asp Gly Val Glu Val His Asn Ala Lys Thr Lys Pro Arg
            340                 345                 350

Glu Glu Gln Tyr Asn Ser Thr Tyr Arg Val Val Ser Val Leu Thr Val
        355                 360                 365

Leu His Gln Asp Trp Leu Asn Gly Lys Glu Tyr Lys Cys Lys Val Ser
    370                 375                 380

Asn Lys Ala Leu Pro Ala Pro Ile Glu Lys Thr Ile Ser Lys Ala Lys
385                 390                 395                 400
```

```
Gly Gln Pro Arg Glu Pro Gln Val Tyr Thr Leu Pro Pro Ser Arg Asp
            405             410             415

Glu Leu Thr Lys Asn Gln Val Ser Leu Trp Cys Leu Val Lys Gly Phe
            420             425             430

Tyr Pro Ser Asp Ile Ala Val Glu Trp Glu Ser Asn Gly Gln Pro Glu
            435             440             445

Asn Asn Tyr Lys Thr Thr Pro Pro Val Leu Asp Ser Asp Gly Ser Phe
    450             455             460

Phe Leu Tyr Ser Lys Leu Thr Val Asp Lys Ser Arg Trp Gln Gln Gly
465             470             475             480

Asn Val Phe Ser Cys Ser Val Met His Glu Ala Leu His Asn His Tyr
            485             490             495

Thr Gln Lys Ser Leu Ser Leu Ser Pro Gly
            500             505
```

```
<210> SEQ ID NO 50
<211> LENGTH: 245
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Met Gly Trp Ser Cys Ile Ile Leu Phe Leu Val Ala Thr Ala Thr Gly
1               5               10              15

Val His Ser Asp Lys Thr His Thr Cys Pro Pro Cys Pro Ala Pro Glu
            20              25              30

Ala Ala Gly Gly Pro Ser Val Phe Leu Phe Pro Pro Lys Pro Lys Asp
            35              40              45

Thr Leu Met Ile Ser Arg Thr Pro Glu Val Thr Cys Val Val Val Asp
    50              55              60

Val Ser His Glu Asp Pro Glu Val Lys Phe Asn Trp Tyr Val Asp Gly
65              70              75              80

Val Glu Val His Asn Ala Lys Thr Lys Pro Arg Glu Glu Gln Tyr Asn
            85              90              95

Ser Thr Tyr Arg Val Val Ser Val Leu Thr Val Leu His Gln Asp Trp
            100             105             110

Leu Asn Gly Lys Glu Tyr Lys Cys Lys Val Ser Asn Lys Ala Leu Pro
            115             120             125

Ala Pro Ile Glu Lys Thr Ile Ser Lys Ala Lys Gly Gln Pro Arg Glu
            130             135             140

Pro Gln Val Tyr Thr Leu Pro Pro Ser Arg Asp Glu Leu Thr Lys Asn
145             150             155             160

Gln Val Ser Leu Ser Cys Ala Val Lys Gly Phe Tyr Pro Ser Asp Ile
            165             170             175

Ala Val Glu Trp Glu Ser Asn Gly Gln Pro Glu Asn Asn Tyr Lys Thr
            180             185             190

Thr Pro Pro Val Leu Asp Ser Asp Gly Ser Phe Phe Leu Val Ser Lys
            195             200             205

Leu Thr Val Asp Lys Ser Arg Trp Gln Gln Gly Asn Val Phe Ser Cys
    210             215             220

Ser Val Met His Glu Ala Leu His Asn His Tyr Thr Gln Lys Ser Leu
225             230             235             240
```

Ser Leu Ser Pro Gly
                245

<210> SEQ ID NO 51
<211> LENGTH: 506
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Met Gly Trp Ser Cys Ile Ile Leu Phe Leu Val Ala Thr Ala Thr Gly
1               5                   10                  15

Val His Ser Met Glu Arg Pro Gln Pro Asp Ser Met Pro Gln Asp Leu
            20                  25                  30

Ser Glu Ala Leu Lys Glu Ala Thr Lys Glu Val His Thr Gln Ala Glu
        35                  40                  45

Asn Ala Glu Phe Met Arg Asn Phe Gln Lys Gly Gln Val Thr Arg Asp
    50                  55                  60

Gly Phe Lys Leu Val Met Ala Ser Leu Tyr His Ile Tyr Val Ala Leu
65                  70                  75                  80

Glu Glu Glu Ile Glu Arg Asn Lys Glu Ser Pro Val Phe Ala Pro Val
                85                  90                  95

Tyr Phe Pro Glu Glu Leu His Arg Lys Ala Ala Leu Glu Gln Asp Leu
            100                 105                 110

Ala Phe Trp Tyr Gly Pro Arg Trp Gln Glu Val Ile Pro Tyr Thr Pro
            115                 120                 125

Ala Met Gln Arg Tyr Val Lys Arg Leu His Glu Val Gly Arg Thr Glu
        130                 135                 140

Pro Glu Leu Leu Val Ala His Ala Tyr Thr Arg Tyr Leu Gly Asp Leu
145                 150                 155                 160

Ser Gly Gly Gln Val Leu Lys Lys Ile Ala Gln Lys Ala Leu Asp Leu
                165                 170                 175

Pro Ser Ser Gly Glu Gly Leu Ala Phe Phe Thr Phe Pro Asn Ile Ala
            180                 185                 190

Ser Ala Thr Lys Phe Lys Gln Leu Tyr Arg Ser Arg Met Asn Ser Leu
            195                 200                 205

Glu Met Thr Pro Ala Val Arg Gln Arg Val Ile Glu Glu Ala Lys Thr
        210                 215                 220

Ala Phe Leu Leu Asn Ile Gln Leu Phe Glu Glu Leu Gln Glu Leu Leu
225                 230                 235                 240

Thr His Asp Thr Lys Asp Gln Ser Pro Ser Arg Ala Pro Gly Leu Arg
            245                 250                 255

Gln Arg Ala Ser Asn Lys Val Gln Asp Ser Ala Pro Val Glu Thr Pro
            260                 265                 270

Arg Gly Lys Pro Pro Leu Asn Thr Asp Lys Thr His Thr Cys Pro Pro
            275                 280                 285

Cys Pro Ala Pro Glu Ala Ala Gly Gly Pro Ser Val Phe Leu Phe Pro
        290                 295                 300

Pro Lys Pro Lys Asp Thr Leu Met Ile Ser Arg Thr Pro Glu Val Thr
305                 310                 315                 320

Cys Val Val Val Asp Val Ser His Glu Asp Pro Glu Val Lys Phe Asn
            325                 330                 335

Trp Tyr Val Asp Gly Val Glu Val His Asn Ala Lys Thr Lys Pro Arg

-continued

```
            340              345              350
Glu Glu Gln Tyr Asn Ser Thr Tyr Arg Val Val Ser Val Leu Thr Val
        355              360              365

Leu His Gln Asp Trp Leu Asn Gly Lys Glu Tyr Lys Cys Lys Val Ser
    370              375              380

Asn Lys Ala Leu Pro Ala Pro Ile Glu Lys Thr Ile Ser Lys Ala Lys
385              390              395              400

Gly Gln Pro Arg Glu Pro Gln Val Tyr Thr Leu Pro Pro Ser Arg Asp
            405              410              415

Glu Leu Thr Glu Asn Gln Val Ser Leu Thr Cys Leu Val Lys Gly Phe
        420              425              430

Tyr Pro Ser Asp Ile Ala Val Glu Trp Glu Ser Asn Gly Gln Pro Glu
        435              440              445

Asn Asn Tyr Lys Thr Thr Pro Pro Val Leu Asp Ser Asp Gly Ser Phe
        450              455              460

Phe Leu Tyr Ser Trp Leu Thr Val Asp Lys Ser Arg Trp Gln Gln Gly
465              470              475              480

Asn Val Phe Ser Cys Ser Val Met His Glu Ala Leu His Asn His Tyr
            485              490              495

Thr Gln Lys Ser Leu Ser Leu Ser Pro Gly
            500              505

<210> SEQ ID NO 52
<211> LENGTH: 245
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Met Gly Trp Ser Cys Ile Ile Leu Phe Leu Val Ala Thr Ala Thr Gly
1                5               10               15

Val His Ser Asp Lys Thr His Thr Cys Pro Pro Cys Pro Ala Pro Glu
            20               25               30

Ala Ala Gly Gly Pro Ser Val Phe Leu Phe Pro Pro Lys Pro Lys Asp
        35               40               45

Thr Leu Met Ile Ser Arg Thr Pro Glu Val Thr Cys Val Val Val Asp
    50               55               60

Val Ser His Glu Asp Pro Glu Val Lys Phe Asn Trp Tyr Val Asp Gly
65               70               75               80

Val Glu Val His Asn Ala Lys Thr Lys Pro Arg Glu Glu Gln Tyr Asn
            85               90               95

Ser Thr Tyr Arg Val Val Ser Val Leu Thr Val Leu His Gln Asp Trp
            100              105              110

Leu Asn Gly Lys Glu Tyr Lys Cys Lys Val Ser Asn Lys Ala Leu Pro
        115              120              125

Ala Pro Ile Glu Lys Thr Ile Ser Lys Ala Lys Gly Gln Pro Arg Glu
        130              135              140

Pro Arg Val Tyr Thr Leu Pro Pro Ser Arg Asp Glu Leu Thr Lys Asn
145              150              155              160

Gln Val Ser Leu Thr Cys Leu Val Lys Gly Phe Tyr Pro Ser Asp Ile
            165              170              175

Ala Val Glu Trp Glu Ser Asn Gly Gln Pro Glu Asn Asn Tyr Lys Thr
            180              185              190
```

-continued

```
Thr Pro Pro Val Leu Val Ser Asp Gly Ser Phe Thr Leu Tyr Ser Lys
        195                 200                 205

Leu Thr Val Asp Lys Ser Arg Trp Gln Gln Gly Asn Val Phe Ser Cys
        210                 215                 220

Ser Val Met His Glu Ala Leu His Asn His Tyr Thr Gln Lys Ser Leu
225                 230                 235                 240

Ser Leu Ser Pro Gly
                245

<210> SEQ ID NO 53
<211> LENGTH: 472
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Met Glu Thr Pro Ala Gln Leu Leu Phe Leu Leu Leu Leu Trp Leu Pro
1               5                   10                  15

Asp Thr Thr Gly Met Glu Arg Pro Gln Pro Asp Ser Met Pro Gln Asp
        20                  25                  30

Leu Ser Glu Ala Leu Lys Glu Ala Thr Lys Glu Val His Thr Gln Ala
        35                  40                  45

Glu Asn Ala Glu Phe Met Arg Asn Phe Gln Lys Gly Gln Val Thr Arg
    50                  55                  60

Asp Gly Phe Lys Leu Val Met Ala Ser Leu Tyr His Ile Tyr Val Ala
65                  70                  75                  80

Leu Glu Glu Glu Ile Glu Arg Asn Lys Glu Ser Pro Val Phe Ala Pro
                85                  90                  95

Val Tyr Phe Pro Glu Glu Leu His Arg Lys Ala Ala Leu Glu Gln Asp
        100                 105                 110

Leu Ala Phe Trp Tyr Gly Pro Arg Trp Gln Glu Val Ile Pro Tyr Thr
        115                 120                 125

Pro Ala Met Gln Arg Tyr Val Lys Arg Leu His Glu Val Gly Arg Thr
        130                 135                 140

Glu Pro Glu Leu Leu Val Ala His Ala Tyr Thr Arg Tyr Leu Gly Asp
145                 150                 155                 160

Leu Ser Gly Gly Gln Val Leu Lys Lys Ile Ala Gln Lys Ala Leu Asp
                165                 170                 175

Leu Pro Ser Ser Gly Glu Gly Leu Ala Phe Phe Thr Phe Pro Asn Ile
                180                 185                 190

Ala Ser Ala Thr Lys Phe Lys Gln Leu Tyr Arg Ser Arg Met Asn Ser
        195                 200                 205

Leu Glu Met Thr Pro Ala Val Arg Gln Arg Val Ile Glu Glu Ala Lys
        210                 215                 220

Thr Ala Phe Leu Leu Asn Ile Gln Leu Phe Glu Glu Leu Gln Glu Leu
225                 230                 235                 240

Leu Thr His Asp Thr Lys Asp Lys Thr His Thr Cys Pro Pro Cys Pro
                245                 250                 255

Ala Pro Glu Ala Ala Gly Gly Pro Ser Val Phe Leu Phe Pro Pro Lys
                260                 265                 270

Pro Lys Asp Thr Leu Met Ile Ser Arg Thr Pro Glu Val Thr Cys Val
        275                 280                 285
```

-continued

```
Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Val Tyr Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Ala Leu
            420                 425                 430

Val Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
    450                 455                 460

Lys Ser Leu Ser Leu Ser Pro Gly
465                 470

<210> SEQ ID NO 54
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Met Glu Thr Pro Ala Gln Leu Leu Phe Leu Leu Leu Leu Trp Leu Pro
1               5                   10                  15

Asp Thr Thr Gly Asp Lys Thr His Thr Cys Pro Pro Cys Pro Ala Pro
                20                  25                  30

Glu Ala Ala Gly Gly Pro Ser Val Phe Leu Phe Pro Pro Lys Pro Lys
            35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
                100                 105                 110

Trp Leu Asn Gly Lys Glu Tyr Lys Cys Lys Val Ser Asn Lys Ala Leu
            115                 120                 125

Pro Ala Pro Ile Glu Lys Thr Ile Ser Lys Ala Lys Gly Gln Pro Arg
    130                 135                 140

Glu Pro Gln Val Tyr Val Leu Pro Pro Ser Arg Asp Glu Leu Thr Lys
145                 150                 155                 160

Asn Gln Val Ser Leu Leu Cys Leu Val Lys Gly Phe Tyr Pro Ser Asp
```

```
                        165                 170                 175

Ile Ala Val Glu Trp Glu Ser Asn Gly Gln Pro Glu Asn Asn Tyr Leu
                180                 185                 190

Thr Trp Pro Pro Val Leu Asp Ser Asp Gly Ser Phe Phe Leu Tyr Ser
            195                 200                 205

Lys Leu Thr Val Asp Lys Ser Arg Trp Gln Gln Gly Asn Val Phe Ser
        210                 215                 220

Cys Ser Val Met His Glu Ala Leu His Asn His Tyr Thr Gln Lys Ser
    225                 230                 235                 240

Leu Ser Leu Ser Pro Gly
                245
```

<210> SEQ ID NO 55
<211> LENGTH: 471
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

```
Met Gly Trp Ser Cys Ile Ile Leu Phe Leu Val Ala Thr Ala Thr Gly
1               5                   10                  15

Val His Ser Asp Lys Thr His Thr Cys Pro Pro Cys Pro Ala Pro Glu
                20                  25                  30

Ala Ala Gly Gly Pro Ser Val Phe Leu Phe Pro Pro Lys Pro Lys Asp
            35                  40                  45

Thr Leu Met Ile Ser Arg Thr Pro Glu Val Thr Cys Val Val Val Asp
        50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
                180                 185                 190

Thr Pro Pro Val Leu Asp Ser Asp Gly Ser Phe Phe Leu Tyr Ser Lys
            195                 200                 205

Leu Thr Val Asp Lys Ser Arg Trp Gln Gln Gly Asn Val Phe Ser Cys
        210                 215                 220

Ser Val Met His Glu Ala Leu His Asn His Tyr Thr Gln Lys Ser Leu
225                 230                 235                 240

Ser Leu Ser Pro Gly Met Glu Arg Pro Gln Pro Asp Ser Met Pro Gln
                245                 250                 255

Asp Leu Ser Glu Ala Leu Lys Glu Ala Thr Lys Glu Val His Thr Gln
            260                 265                 270
```

-continued

```
Ala Glu Asn Ala Glu Phe Met Arg Asn Phe Gln Lys Gly Gln Val Thr
        275                 280                 285

Arg Asp Gly Phe Lys Leu Val Met Ala Ser Leu Tyr His Ile Tyr Val
        290                 295                 300

Ala Leu Glu Glu Glu Ile Glu Arg Asn Lys Glu Ser Pro Val Phe Ala
305                 310                 315                 320

Pro Val Tyr Phe Pro Glu Glu Leu His Arg Lys Ala Ala Leu Glu Gln
                325                 330                 335

Asp Leu Ala Phe Trp Tyr Gly Pro Arg Trp Gln Glu Val Ile Pro Tyr
                340                 345                 350

Thr Pro Ala Met Gln Arg Tyr Val Lys Arg Leu His Glu Val Gly Arg
        355                 360                 365

Thr Glu Pro Glu Leu Leu Val Ala His Ala Tyr Thr Arg Tyr Leu Gly
        370                 375                 380

Asp Leu Ser Gly Gly Gln Val Leu Lys Lys Ile Ala Gln Lys Ala Leu
385                 390                 395                 400

Asp Leu Pro Ser Ser Gly Glu Gly Leu Ala Phe Phe Thr Phe Pro Asn
                405                 410                 415

Ile Ala Ser Ala Thr Lys Phe Lys Gln Leu Tyr Arg Ser Arg Met Asn
                420                 425                 430

Ser Leu Glu Met Thr Pro Ala Val Arg Gln Arg Val Ile Glu Glu Ala
        435                 440                 445

Lys Thr Ala Phe Leu Leu Asn Ile Gln Leu Phe Glu Glu Leu Gln Glu
        450                 455                 460

Leu Leu Thr His Asp Thr Lys
465                 470

<210> SEQ ID NO 56
<211> LENGTH: 471
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Met Gly Trp Ser Cys Ile Ile Leu Phe Leu Val Ala Thr Ala Thr Gly
1               5                   10                  15

Val His Ser Met Glu Arg Pro Gln Pro Asp Ser Met Pro Gln Asp Leu
                20                  25                  30

Ser Glu Ala Leu Lys Glu Ala Thr Lys Glu Val His Thr Gln Ala Glu
        35                  40                  45

Asn Ala Glu Phe Met Arg Asn Phe Gln Lys Gly Gln Val Thr Arg Asp
        50                  55                  60

Gly Phe Lys Leu Val Met Ala Ser Leu Tyr His Ile Tyr Val Ala Leu
65                  70                  75                  80

Glu Glu Glu Ile Glu Arg Asn Lys Glu Ser Pro Val Phe Ala Pro Val
                85                  90                  95

Tyr Phe Pro Glu Glu Leu His Arg Lys Ala Ala Leu Glu Gln Asp Leu
                100                 105                 110

Ala Phe Trp Tyr Gly Pro Arg Trp Gln Glu Val Ile Pro Tyr Thr Pro
        115                 120                 125

Ala Met Gln Arg Tyr Val Lys Arg Leu His Glu Val Gly Arg Thr Glu
        130                 135                 140
```

```
Pro Glu Leu Leu Val Ala His Ala Tyr Thr Arg Tyr Leu Gly Asp Leu
145             150             155             160

Ser Gly Gly Gln Val Leu Lys Lys Ile Ala Gln Lys Ala Leu Asp Leu
                165             170             175

Pro Ser Ser Gly Glu Gly Leu Ala Phe Phe Thr Phe Pro Asn Ile Ala
            180             185             190

Ser Ala Thr Lys Phe Lys Gln Leu Tyr Arg Ser Arg Met Asn Ser Leu
        195             200             205

Glu Met Thr Pro Ala Val Arg Gln Arg Val Ile Glu Glu Ala Lys Thr
    210             215             220

Ala Phe Leu Leu Asn Ile Gln Leu Phe Glu Glu Leu Gln Glu Leu Leu
225             230             235             240

Thr His Asp Thr Lys Asp Lys Thr His Thr Cys Pro Pro Cys Pro Ala
            245             250             255

Pro Glu Ala Ala Gly Gly Pro Ser Val Phe Leu Phe Pro Pro Lys Pro
            260             265             270

Lys Asp Thr Leu Met Ile Ser Arg Thr Pro Glu Val Thr Cys Val Val
            275             280             285

Val Asp Val Ser His Glu Asp Pro Glu Val Lys Phe Asn Trp Tyr Val
    290             295             300

Asp Gly Val Glu Val His Asn Ala Lys Thr Lys Pro Arg Glu Glu Gln
305             310             315             320

Tyr Asn Ser Thr Tyr Arg Val Val Ser Val Leu Thr Val Leu His Gln
            325             330             335

Asp Trp Leu Asn Gly Lys Glu Tyr Lys Cys Lys Val Ser Asn Lys Ala
            340             345             350

Leu Pro Ala Pro Ile Glu Lys Thr Ile Ser Lys Ala Lys Gly Gln Pro
            355             360             365

Arg Glu Pro Gln Val Tyr Thr Leu Pro Pro Ser Arg Asp Glu Leu Thr
    370             375             380

Lys Asn Gln Val Ser Leu Thr Cys Leu Val Lys Gly Phe Tyr Pro Ser
385             390             395             400

Asp Ile Ala Val Glu Trp Glu Ser Asn Gly Gln Pro Glu Asn Asn Tyr
            405             410             415

Lys Thr Thr Pro Pro Val Leu Asp Ser Asp Gly Ser Phe Phe Leu Tyr
            420             425             430

Ser Lys Leu Thr Val Asp Lys Ser Arg Trp Gln Gln Gly Asn Val Phe
            435             440             445

Ser Cys Ser Val Met His Glu Ala Leu His Asn His Tyr Thr Gln Lys
    450             455             460

Ser Leu Ser Leu Ser Pro Gly
465             470

<210> SEQ ID NO 57
<211> LENGTH: 778
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Met Gly Trp Ser Cys Ile Ile Leu Phe Leu Val Ala Thr Ala Thr Gly
1               5               10              15

Val His Ser Met Glu Arg Pro Gln Pro Asp Ser Met Pro Gln Asp Leu
```

```
                20                25                30

Ser Glu Ala Leu Lys Glu Ala Thr Lys Glu Val His Thr Gln Ala Glu
        35                40                45

Asn Ala Glu Phe Met Arg Asn Phe Gln Lys Gly Gln Val Thr Arg Asp
        50                55                60

Gly Phe Lys Leu Val Met Ala Ser Leu Tyr His Ile Tyr Val Ala Leu
65                70                75                80

Glu Glu Glu Ile Glu Arg Asn Lys Glu Ser Pro Val Phe Ala Pro Val
                85                90                95

Tyr Phe Pro Glu Glu Leu His Arg Lys Ala Ala Leu Glu Gln Asp Leu
            100               105               110

Ala Phe Trp Tyr Gly Pro Arg Trp Gln Glu Val Ile Pro Tyr Thr Pro
        115               120               125

Ala Met Gln Arg Tyr Val Lys Arg Leu His Glu Val Gly Arg Thr Glu
        130               135               140

Pro Glu Leu Leu Val Ala His Ala Tyr Thr Arg Tyr Leu Gly Asp Leu
145               150               155               160

Ser Gly Gly Gln Val Leu Lys Lys Ile Ala Gln Lys Ala Leu Asp Leu
                165               170               175

Pro Ser Ser Gly Glu Gly Leu Ala Phe Phe Thr Phe Pro Asn Ile Ala
            180               185               190

Ser Ala Thr Lys Phe Lys Gln Leu Tyr Arg Ser Arg Met Asn Ser Leu
            195               200               205

Glu Met Thr Pro Ala Val Arg Gln Arg Val Ile Glu Glu Ala Lys Thr
        210               215               220

Ala Phe Leu Leu Asn Ile Gln Leu Phe Glu Glu Leu Gln Glu Leu Leu
225               230               235               240

Thr His Asp Thr Lys Asp Gln Ser Pro Ser Arg Ala Pro Gly Leu Arg
            245               250               255

Gln Arg Ala Ser Asn Lys Val Gln Asp Ser Ala Pro Val Glu Thr Pro
            260               265               270

Arg Gly Lys Pro Pro Leu Asn Thr Asp Lys Thr His Thr Cys Pro Pro
            275               280               285

Cys Pro Ala Pro Glu Ala Ala Gly Gly Pro Ser Val Phe Leu Phe Pro
        290               295               300

Pro Lys Pro Lys Asp Thr Leu Met Ile Ser Arg Thr Pro Glu Val Thr
305               310               315               320

Cys Val Val Val Asp Val Ser His Glu Asp Pro Glu Val Lys Phe Asn
            325               330               335

Trp Tyr Val Asp Gly Val Glu Val His Asn Ala Lys Thr Lys Pro Arg
            340               345               350

Glu Glu Gln Tyr Asn Ser Thr Tyr Arg Val Val Ser Val Leu Thr Val
            355               360               365

Leu His Gln Asp Trp Leu Asn Gly Lys Glu Tyr Lys Cys Lys Val Ser
        370               375               380

Asn Lys Ala Leu Pro Ala Pro Ile Glu Lys Thr Ile Ser Lys Ala Lys
385               390               395               400

Gly Gln Pro Arg Glu Pro Gln Val Tyr Thr Leu Pro Pro Ser Arg Asp
            405               410               415

Glu Leu Thr Lys Asn Gln Val Ser Leu Thr Cys Leu Val Lys Gly Phe
            420               425               430

Tyr Pro Ser Asp Ile Ala Val Glu Trp Glu Ser Asn Gly Gln Pro Glu
            435               440               445
```

```
Asn Asn Tyr Lys Thr Thr Pro Pro Val Leu Asp Ser Asp Gly Ser Phe
    450             455             460

Phe Leu Tyr Ser Lys Leu Thr Val Asp Lys Ser Arg Trp Gln Gln Gly
465             470             475             480

Asn Val Phe Ser Cys Ser Val Met His Glu Ala Leu His Asn His Tyr
            485             490             495

Thr Gln Lys Ser Leu Ser Leu Ser Pro Gly Gly Gly Gly Ser Gly
            500             505             510

Gly Gly Gly Ser Gly Gly Gly Gly Ser Gly Gly Gly Gly Ser Gly Gly
            515             520             525

Gly Gly Ser Gly Gly Gly Gly Ser Gly Gly Gly Gly Ser Gly Gly Gly
            530             535             540

Gly Ser Gly Glu Pro Lys Ser Ser Asp Lys Thr His Thr Cys Pro Pro
545             550             555             560

Cys Pro Ala Pro Glu Ala Ala Gly Gly Pro Ser Val Phe Leu Phe Pro
            565             570             575

Pro Lys Pro Lys Asp Thr Leu Met Ile Ser Arg Thr Pro Glu Val Thr
            580             585             590

Cys Val Val Val Asp Val Ser His Glu Asp Pro Glu Val Lys Phe Asn
            595             600             605

Trp Tyr Val Asp Gly Val Glu Val His Asn Ala Lys Thr Lys Pro Arg
    610             615             620

Glu Glu Gln Tyr Asn Ser Thr Tyr Arg Val Val Ser Val Leu Thr Val
625             630             635             640

Leu His Gln Asp Trp Leu Asn Gly Lys Glu Tyr Lys Cys Lys Val Ser
            645             650             655

Asn Lys Ala Leu Pro Ala Pro Ile Glu Lys Thr Ile Ser Lys Ala Lys
            660             665             670

Gly Gln Pro Arg Glu Pro Gln Val Tyr Thr Leu Pro Pro Ser Arg Asp
            675             680             685

Glu Leu Thr Lys Asn Gln Val Ser Leu Thr Cys Leu Val Lys Gly Phe
            690             695             700

Tyr Pro Ser Asp Ile Ala Val Glu Trp Glu Ser Asn Gly Gln Pro Glu
705             710             715             720

Asn Asn Tyr Lys Thr Thr Pro Pro Val Leu Asp Ser Asp Gly Ser Phe
            725             730             735

Phe Leu Tyr Ser Lys Leu Thr Val Asp Lys Ser Arg Trp Gln Gln Gly
            740             745             750

Asn Val Phe Ser Cys Ser Val Met His Glu Ala Leu His Asn His Tyr
            755             760             765

Thr Gln Lys Ser Leu Ser Leu Ser Pro Gly
    770             775
```

```
<210> SEQ ID NO 58
<211> LENGTH: 779
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Met Gly Trp Ser Cys Ile Ile Leu Phe Leu Val Ala Thr Ala Thr Gly
1               5               10              15
```

```
Val His Ser Met Glu Arg Pro Gln Pro Asp Ser Met Pro Gln Asp Leu
            20              25              30

Ser Glu Ala Leu Lys Glu Ala Thr Lys Glu Val His Thr Gln Ala Glu
            35              40              45

Asn Ala Glu Phe Met Arg Asn Phe Gln Lys Gly Gln Val Thr Arg Asp
            50              55              60

Gly Phe Lys Leu Val Met Ala Ser Leu Tyr His Ile Tyr Val Ala Leu
65              70              75              80

Glu Glu Glu Ile Glu Arg Asn Lys Glu Ser Pro Val Phe Ala Pro Val
            85              90              95

Tyr Phe Pro Glu Glu Leu His Arg Lys Ala Ala Leu Glu Gln Asp Leu
            100             105             110

Ala Phe Trp Tyr Gly Pro Arg Trp Gln Glu Val Ile Pro Tyr Thr Pro
            115             120             125

Ala Met Gln Arg Tyr Val Lys Arg Leu His Glu Val Gly Arg Thr Glu
            130             135             140

Pro Glu Leu Leu Val Ala His Ala Tyr Thr Arg Tyr Leu Gly Asp Leu
145             150             155             160

Ser Gly Gly Gln Val Leu Lys Lys Ile Ala Gln Lys Ala Leu Asp Leu
            165             170             175

Pro Ser Ser Gly Glu Gly Leu Ala Phe Phe Thr Phe Pro Asn Ile Ala
            180             185             190

Ser Ala Thr Lys Phe Lys Gln Leu Tyr Arg Ser Arg Met Asn Ser Leu
            195             200             205

Glu Met Thr Pro Ala Val Arg Gln Arg Val Ile Glu Glu Ala Lys Thr
            210             215             220

Ala Phe Leu Leu Asn Ile Gln Leu Phe Glu Glu Leu Gln Glu Leu Leu
225             230             235             240

Thr His Asp Thr Lys Asp Gln Ser Pro Ser Arg Ala Pro Gly Leu Arg
            245             250             255

Gln Arg Ala Ser Asn Lys Val Gln Asp Ser Ala Pro Val Glu Thr Pro
            260             265             270

Arg Gly Lys Pro Pro Leu Asn Thr Pro Ala Pro Glu Ala Ala Gly Gly
            275             280             285

Pro Ser Val Phe Leu Phe Pro Pro Lys Pro Lys Asp Thr Leu Met Ile
            290             295             300

Ser Arg Thr Pro Glu Val Thr Cys Val Val Val Asp Val Ser His Glu
305             310             315             320

Asp Pro Glu Val Lys Phe Asn Trp Tyr Val Asp Gly Val Glu Val His
            325             330             335

Asn Ala Lys Thr Lys Pro Arg Glu Glu Gln Tyr Asn Ser Thr Tyr Arg
            340             345             350

Val Val Ser Val Leu Thr Val Leu His Gln Asp Trp Leu Asn Gly Lys
            355             360             365

Glu Tyr Lys Cys Lys Val Ser Asn Lys Ala Leu Pro Ala Pro Ile Glu
            370             375             380

Lys Thr Ile Ser Lys Ala Lys Gly Gln Pro Arg Glu Pro Gln Val Tyr
385             390             395             400

Thr Leu Pro Pro Ser Arg Asp Lys Leu Thr Lys Asn Gln Val Ser Leu
            405             410             415

Thr Cys Leu Val Lys Gly Phe Tyr Pro Ser Asp Ile Ala Val Glu Trp
            420             425             430

Glu Ser Asn Gly Gln Pro Glu Asn Asn Tyr Lys Thr Thr Pro Pro Val
```

```
                435                     440                     445

Leu Asp Ser Asp Gly Ser Phe Phe Leu Tyr Ser Lys Leu Thr Val Asp
            450                     455                     460

Lys Ser Arg Trp Gln Gln Gly Asn Val Phe Ser Cys Ser Val Met His
        465                     470                     475                 480

Glu Ala Leu His Asn His Tyr Thr Gln Lys Ser Leu Ser Leu Ser Pro
                                485                     490                     495

Gly Gly Gly Gly Gly Ser Gly Gly Gly Gly Ser Gly Gly Gly Gly Ser
                        500                     505                     510

Gly Gly Gly Gly Ser Gly Gly Gly Gly Ser Gly Gly Gly Gly Ser Gly
                        515                     520                     525

Gly Gly Gly Ser Gly Gly Gly Gly Ser Gly Gly Gly Gly Ser Gly Gly
                    530                     535                     540

Gly Gly Ser Gly Gly Gly Gly Ser Gly Gly Gly Gly Ser Gly Gly Gly
        545                     550                     555                 560

Gly Ser Pro Ala Pro Glu Ala Ala Gly Gly Pro Ser Val Phe Leu Phe
                        565                     570                     575

Pro Pro Lys Pro Lys Asp Thr Leu Met Ile Ser Arg Thr Pro Glu Val
                        580                     585                     590

Thr Cys Val Val Val Asp Val Ser His Glu Asp Pro Glu Val Lys Phe
                        595                     600                     605

Asn Trp Tyr Val Asp Gly Val Glu Val His Asn Ala Lys Thr Lys Pro
                610                     615                     620

Arg Glu Glu Gln Tyr Asn Ser Thr Tyr Arg Val Val Ser Val Leu Thr
        625                     630                     635                 640

Val Leu His Gln Asp Trp Leu Asn Gly Lys Glu Tyr Lys Cys Lys Val
                            645                     650                     655

Ser Asn Lys Ala Leu Pro Ala Pro Ile Glu Lys Thr Ile Ser Lys Ala
                        660                     665                     670

Lys Gly Gln Pro Arg Glu Pro Gln Val Tyr Thr Leu Pro Pro Ser Arg
                        675                     680                     685

Asp Glu Leu Thr Lys Asn Gln Val Ser Leu Thr Cys Leu Val Asp Gly
                690                     695                     700

Phe Tyr Pro Ser Asp Ile Ala Val Glu Trp Glu Ser Asn Gly Gln Pro
        705                     710                     715                 720

Glu Asn Asn Tyr Lys Thr Thr Pro Pro Val Leu Asp Ser Asp Gly Ser
                        725                     730                     735

Phe Phe Leu Tyr Ser Lys Leu Thr Val Asp Lys Ser Arg Trp Gln Gln
                        740                     745                     750

Gly Asn Val Phe Ser Cys Ser Val Met His Glu Ala Leu His Asn His
                        755                     760                     765

Tyr Thr Gln Lys Ser Leu Ser Leu Ser Pro Gly
                770                     775
```

<210> SEQ ID NO 59
<211> LENGTH: 743
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

```
        Met Gly Trp Ser Cys Ile Ile Leu Phe Leu Val Ala Thr Ala Thr Gly
        1               5                       10                      15
```

-continued

```
Val His Ser Met Glu Arg Pro Gln Pro Asp Ser Met Pro Gln Asp Leu
            20              25              30

Ser Glu Ala Leu Lys Glu Ala Thr Lys Glu Val His Thr Gln Ala Glu
            35              40              45

Asn Ala Glu Phe Met Arg Asn Phe Gln Lys Gly Gln Val Thr Arg Asp
            50              55              60

Gly Phe Lys Leu Val Met Ala Ser Leu Tyr His Ile Tyr Val Ala Leu
65              70              75              80

Glu Glu Glu Ile Glu Arg Asn Lys Glu Ser Pro Val Phe Ala Pro Val
                85              90              95

Tyr Phe Pro Glu Glu Leu His Arg Lys Ala Ala Leu Glu Gln Asp Leu
            100             105             110

Ala Phe Trp Tyr Gly Pro Arg Trp Gln Glu Val Ile Pro Tyr Thr Pro
            115             120             125

Ala Met Gln Arg Tyr Val Lys Arg Leu His Glu Val Gly Arg Thr Glu
            130             135             140

Pro Glu Leu Leu Val Ala His Ala Tyr Thr Arg Tyr Leu Gly Asp Leu
145             150             155             160

Ser Gly Gly Gln Val Leu Lys Lys Ile Ala Gln Lys Ala Leu Asp Leu
                165             170             175

Pro Ser Ser Gly Glu Gly Leu Ala Phe Phe Thr Phe Pro Asn Ile Ala
                180             185             190

Ser Ala Thr Lys Phe Lys Gln Leu Tyr Arg Ser Arg Met Asn Ser Leu
                195             200             205

Glu Met Thr Pro Ala Val Arg Gln Arg Val Ile Glu Glu Ala Lys Thr
            210             215             220

Ala Phe Leu Leu Asn Ile Gln Leu Phe Glu Glu Leu Gln Glu Leu Leu
225             230             235             240

Thr His Asp Thr Lys Asp Lys Thr His Thr Cys Pro Pro Cys Pro Ala
                245             250             255

Pro Glu Ala Ala Gly Gly Pro Ser Val Phe Leu Phe Pro Pro Lys Pro
            260             265             270

Lys Asp Thr Leu Met Ile Ser Arg Thr Pro Glu Val Thr Cys Val Val
                275             280             285

Val Asp Val Ser His Glu Asp Pro Glu Val Lys Phe Asn Trp Tyr Val
            290             295             300

Asp Gly Val Glu Val His Asn Ala Lys Thr Lys Pro Arg Glu Glu Gln
305             310             315             320

Tyr Asn Ser Thr Tyr Arg Val Val Ser Val Leu Thr Val Leu His Gln
                325             330             335

Asp Trp Leu Asn Gly Lys Glu Tyr Lys Cys Lys Val Ser Asn Lys Ala
                340             345             350

Leu Pro Ala Pro Ile Glu Lys Thr Ile Ser Lys Ala Lys Gly Gln Pro
                355             360             365

Arg Glu Pro Gln Val Tyr Thr Leu Pro Pro Ser Arg Asp Glu Leu Thr
            370             375             380

Lys Asn Gln Val Ser Leu Thr Cys Leu Val Lys Gly Phe Tyr Pro Ser
385             390             395             400

Asp Ile Ala Val Glu Trp Glu Ser Asn Gly Gln Pro Glu Asn Asn Tyr
                405             410             415

Lys Thr Thr Pro Pro Val Leu Asp Ser Asp Gly Ser Phe Phe Leu Tyr
                420             425             430
```

```
Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
        450                 455                 460

Ser Leu Ser Leu Ser Pro Gly Gly Gly Gly Gly Ser Gly Gly Gly Gly
465                 470                 475                 480

Ser Gly Gly Gly Gly Ser Gly Gly Gly Gly Ser Gly Gly Gly Gly Ser
                485                 490                 495

Gly Gly Gly Gly Ser Gly Gly Gly Gly Ser Gly Gly Gly Gly Ser Gly
                500                 505                 510

Glu Pro Lys Ser Ser Asp Lys Thr His Thr Cys Pro Pro Cys Pro Ala
        515                 520                 525

Pro Glu Ala Ala Gly Gly Pro Ser Val Phe Leu Phe Pro Pro Lys Pro
        530                 535                 540

Lys Asp Thr Leu Met Ile Ser Arg Thr Pro Glu Val Thr Cys Val Val
545                 550                 555                 560

Val Asp Val Ser His Glu Asp Pro Glu Val Lys Phe Asn Trp Tyr Val
                565                 570                 575

Asp Gly Val Glu Val His Asn Ala Lys Thr Lys Pro Arg Glu Glu Gln
                580                 585                 590

Tyr Asn Ser Thr Tyr Arg Val Val Ser Val Leu Thr Val Leu His Gln
                595                 600                 605

Asp Trp Leu Asn Gly Lys Glu Tyr Lys Cys Lys Val Ser Asn Lys Ala
        610                 615                 620

Leu Pro Ala Pro Ile Glu Lys Thr Ile Ser Lys Ala Lys Gly Gln Pro
625                 630                 635                 640

Arg Glu Pro Gln Val Tyr Thr Leu Pro Pro Ser Arg Asp Glu Leu Thr
                645                 650                 655

Lys Asn Gln Val Ser Leu Thr Cys Leu Val Lys Gly Phe Tyr Pro Ser
                660                 665                 670

Asp Ile Ala Val Glu Trp Glu Ser Asn Gly Gln Pro Glu Asn Asn Tyr
                675                 680                 685

Lys Thr Thr Pro Pro Val Leu Asp Ser Asp Gly Ser Phe Phe Leu Tyr
        690                 695                 700

Ser Lys Leu Thr Val Asp Lys Ser Arg Trp Gln Gln Gly Asn Val Phe
705                 710                 715                 720

Ser Cys Ser Val Met His Glu Ala Leu His Asn His Tyr Thr Gln Lys
                725                 730                 735

Ser Leu Ser Leu Ser Pro Gly
            740
```

```
<210> SEQ ID NO 60
<211> LENGTH: 744
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Met Gly Trp Ser Cys Ile Ile Leu Phe Leu Val Ala Thr Ala Thr Gly
1               5                   10                  15

Val His Ser Met Glu Arg Pro Gln Pro Asp Ser Met Pro Gln Asp Leu
            20                  25                  30

Ser Glu Ala Leu Lys Glu Ala Thr Lys Glu Val His Thr Gln Ala Glu
```

-continued

```
              35                    40                    45

Asn Ala Glu Phe Met Arg Asn Phe Gln Lys Gly Gln Val Thr Arg Asp
    50                    55                    60

Gly Phe Lys Leu Val Met Ala Ser Leu Tyr His Ile Tyr Val Ala Leu
65                    70                    75                    80

Glu Glu Glu Ile Glu Arg Asn Lys Glu Ser Pro Val Phe Ala Pro Val
                  85                    90                    95

Tyr Phe Pro Glu Glu Leu His Arg Lys Ala Ala Leu Glu Gln Asp Leu
                  100                   105                   110

Ala Phe Trp Tyr Gly Pro Arg Trp Gln Glu Val Ile Pro Tyr Thr Pro
                  115                   120                   125

Ala Met Gln Arg Tyr Val Lys Arg Leu His Glu Val Gly Arg Thr Glu
    130                   135                   140

Pro Glu Leu Leu Val Ala His Ala Tyr Thr Arg Tyr Leu Gly Asp Leu
145                   150                   155                   160

Ser Gly Gly Gln Val Leu Lys Lys Ile Ala Gln Lys Ala Leu Asp Leu
                  165                   170                   175

Pro Ser Ser Gly Glu Gly Leu Ala Phe Phe Thr Phe Pro Asn Ile Ala
                  180                   185                   190

Ser Ala Thr Lys Phe Lys Gln Leu Tyr Arg Ser Arg Met Asn Ser Leu
                  195                   200                   205

Glu Met Thr Pro Ala Val Arg Gln Arg Val Ile Glu Glu Ala Lys Thr
    210                   215                   220

Ala Phe Leu Leu Asn Ile Gln Leu Phe Glu Glu Leu Gln Glu Leu Leu
225                   230                   235                   240

Thr His Asp Thr Lys Pro Ala Pro Glu Ala Ala Gly Gly Pro Ser Val
                  245                   250                   255

Phe Leu Phe Pro Pro Lys Pro Lys Asp Thr Leu Met Ile Ser Arg Thr
                  260                   265                   270

Pro Glu Val Thr Cys Val Val Val Asp Val Ser His Glu Asp Pro Glu
                  275                   280                   285

Val Lys Phe Asn Trp Tyr Val Asp Gly Val Glu Val His Asn Ala Lys
    290                   295                   300

Thr Lys Pro Arg Glu Glu Gln Tyr Asn Ser Thr Tyr Arg Val Val Ser
305                   310                   315                   320

Val Leu Thr Val Leu His Gln Asp Trp Leu Asn Gly Lys Glu Tyr Lys
                  325                   330                   335

Cys Lys Val Ser Asn Lys Ala Leu Pro Ala Pro Ile Glu Lys Thr Ile
                  340                   345                   350

Ser Lys Ala Lys Gly Gln Pro Arg Glu Pro Gln Val Tyr Thr Leu Pro
                  355                   360                   365

Pro Ser Arg Asp Lys Leu Thr Lys Asn Gln Val Ser Leu Thr Cys Leu
    370                   375                   380

Val Lys Gly Phe Tyr Pro Ser Asp Ile Ala Val Glu Trp Glu Ser Asn
385                   390                   395                   400

Gly Gln Pro Glu Asn Asn Tyr Lys Thr Thr Pro Pro Val Leu Asp Ser
                  405                   410                   415

Asp Gly Ser Phe Phe Leu Tyr Ser Lys Leu Thr Val Asp Lys Ser Arg
                  420                   425                   430

Trp Gln Gln Gly Asn Val Phe Ser Cys Ser Val Met His Glu Ala Leu
                  435                   440                   445

His Asn His Tyr Thr Gln Lys Ser Leu Ser Leu Ser Pro Gly Gly Gly
    450                   455                   460
```

```
Gly Gly Ser Gly Gly Gly Gly Ser Gly Gly Gly Ser Gly Gly
465             470             475             480

Gly Ser Gly Gly Gly Gly Ser Gly Gly Gly Gly Ser Gly Gly Gly Gly
            485             490             495

Ser Gly Gly Gly Gly Ser Gly Gly Gly Gly Ser Gly Gly Gly Gly Ser
        500             505             510

Gly Gly Gly Gly Ser Gly Gly Gly Gly Ser Gly Gly Gly Gly Ser Pro
        515             520             525

Ala Pro Glu Ala Ala Gly Gly Pro Ser Val Phe Leu Phe Pro Pro Lys
        530             535             540

Pro Lys Asp Thr Leu Met Ile Ser Arg Thr Pro Glu Val Thr Cys Val
545             550             555             560

Val Val Asp Val Ser His Glu Asp Pro Glu Val Lys Phe Asn Trp Tyr
            565             570             575

Val Asp Gly Val Glu Val His Asn Ala Lys Thr Lys Pro Arg Glu Glu
            580             585             590

Gln Tyr Asn Ser Thr Tyr Arg Val Val Ser Val Leu Thr Val Leu His
        595             600             605

Gln Asp Trp Leu Asn Gly Lys Glu Tyr Lys Cys Lys Val Ser Asn Lys
        610             615             620

Ala Leu Pro Ala Pro Ile Glu Lys Thr Ile Ser Lys Ala Lys Gly Gln
625             630             635             640

Pro Arg Glu Pro Gln Val Tyr Thr Leu Pro Pro Ser Arg Asp Glu Leu
            645             650             655

Thr Lys Asn Gln Val Ser Leu Thr Cys Leu Val Asp Gly Phe Tyr Pro
            660             665             670

Ser Asp Ile Ala Val Glu Trp Glu Ser Asn Gly Gln Pro Glu Asn Asn
            675             680             685

Tyr Lys Thr Thr Pro Pro Val Leu Asp Ser Asp Gly Ser Phe Phe Leu
            690             695             700

Tyr Ser Lys Leu Thr Val Asp Lys Ser Arg Trp Gln Gln Gly Asn Val
705             710             715             720

Phe Ser Cys Ser Val Met His Glu Ala Leu His Asn His Tyr Thr Gln
            725             730             735

Lys Ser Leu Ser Leu Ser Pro Gly
            740
```

```
<210> SEQ ID NO 61
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (1)..(25)
<223> OTHER INFORMATION: /note="This sequence may encompass 1-5 'Gly Gly
      Gly Gly Ser' repeating units"

<400> SEQUENCE: 61

Gly Gly Gly Gly Ser Gly Gly Gly Gly Ser Gly Gly Gly Gly Ser Gly
1               5               10              15

Gly Gly Gly Ser Gly Gly Gly Gly Ser
            20              25
```

-continued

```
<210> SEQ ID NO 62
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="See specification as filed for detailed
      description of substitutions and preferred embodiments"

<400> SEQUENCE: 62

Gly Gly Gly Gly Ser Gly Gly Gly Gly Ser
1               5                   10

<210> SEQ ID NO 63
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 64
<211> LENGTH: 65
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser
65

<210> SEQ ID NO 65
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Gly Gly Gly Gly Ser Gly Gly Gly Gly Ser Gly Gly Gly Gly Ser Gly
```

-continued

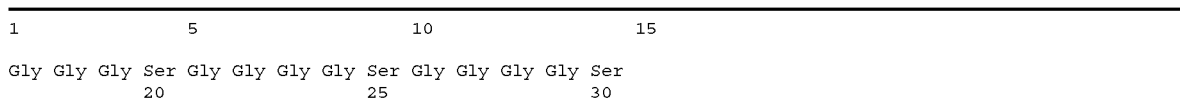

```
1            5              10             15

Gly Gly Gly Ser Gly Gly Gly Gly Ser Gly Gly Gly Gly Ser
        20              25             30
```

RECOMBINANT HEME OXYGENASE-1 (HO-1) FOR THE TREATMENT OF SICKLE CELL DISEASE

CROSS REFERENCE TO RELATED APPLICATIONS

This application is a 35 U.S.C. § 371 National Stage Application of International Application No. PCT/US20/43452, filed on Jul. 24, 2020, which claims priority to U.S. Patent Application Ser. Nos. 62/879,131 filed Jul. 26, 2019; and 63/049,285 filed Jul. 8, 2020; the entirety of each of which is hereby incorporated by reference.

STATEMENT OF FEDERALLY FUNDED RESEARCH

This invention was made with United States government support under grant U01HL117721 awarded by the National Institutes of Health. The United States government has certain rights in the invention.

SEQUENCE LISTING

The instant application contains a Sequence Listing which has been submitted electronically in ASCII format and is hereby incorporated by reference in its entirety. Said ASCII copy, created on Jul. 17, 2020, is named SHR-2009WO_SL.txt and is 200,037 bytes in size.

BACKGROUND

Sickle cell disease (SCD) is a chronic life-threatening blood disorder that is inherited as an autosomal recessive trait. SCD is associated with many acute and chronic complications resulting in part from an excess amount of cell-free hemoglobin (Hb) and cell-free heme due to severe hemolysis.

Patients with SCD have sickle-shaped red blood cells that get lodged in small blood vessels, obstructing the flow of blood and oxygen to major organs in the body. Such blockages result in severe pain, organ damage, stroke and other complications including increased vulnerability to infection, fatigue, and delayed growth. Most people with the disease have shortened life spans. There is a need for effective therapies to treat patients with complications arising from SCD.

SUMMARY OF THE INVENTION

The present invention provides an effective method for treating SCD. The present invention is based, in part, on the discovery that systemic administration of a recombinant heme oxygenase (e.g., a truncated HO-1 protein or a HO-1-Fc fusion protein) reduces or ameliorates symptoms of sickle cell disease in a SCD mouse model. Without wishing to be bound by any particular theory, it is contemplated that HO-1 specifically targets and degrades free heme by converting cell free heme into cytoprotective/anti-inflammatory by-products. Administration of a recombinant heme oxygenase augments the HO-1 activity in plasma, reduces anemia, prevents acute chest syndrome (ACS), pulmonary hypertension, and acute damage to the lungs in a SCD disease model. Furthermore, the SCD therapy described herein harnesses the physiological specificity that an endogenous HO-1 protein has and can potentially minimize off-target effects. Described herein are recombinant therapeutic HO-1 proteins which retain enzymatic activity while extending half-life, increasing stability, and decreasing aggregation compared to a naturally-occurring HO-1 protein.

In one aspect, the present invention provides a method of treating sickle cell disease comprising administering to a subject in need of treatment a recombinant heme oxygenase-1 (rHO-1) protein.

In some embodiments, the method comprises administering an rHO-1 protein comprising an amino acid sequence with at least 85% identity to residues 1-261 of SEQ ID NO:1 (wild type full length rHO-1 protein).

In some embodiments, the method comprises administering an rHO-1 protein comprising an amino acid sequence with at least 90% identity to residues 1-261 of SEQ ID NO:1 (wild type full length rHO-1 protein).

In some embodiments, the method comprises administering an rHO-1 protein comprising an amino acid sequence with at least 95% identity to residues 1-261 of SEQ ID NO:1 (wild type full length rHO-1 protein).

In some embodiments, the method comprises administering an rHO-1 protein comprising an amino acid sequence identical to residues 1-261 of SEQ ID NO:1 (wild type full length rHO-1 protein).

In some embodiments, the method comprises administering an rHO-1 protein comprising SEQ ID NO:1.

In some embodiments, the method comprises administering an rHO-1 protein comprising K18, T21, H25, Y134, G143, L147, K179, and F207 (corresponding to amino acids positions of SEQ ID NO:1).

In some embodiments, the method comprises administering an rHO-1 protein wherein the rHO-1 protein is truncated at the N-terminus at a residue corresponding to M9 of SEQ ID NO: 1. In some embodiments, the method comprises administering an rHO-1 protein, wherein the rHO-1 protein comprises residues 10-225 of SEQ ID NO: 1. In some embodiments, the method comprises administering an rHO-1 protein, wherein the rHO-1 protein comprises residues 10-226 of SEQ ID NO: 1. In some embodiments, the method comprises administering an rHO-1 protein, wherein the rHO-1 protein comprises residues 10-261 of SEQ ID NO: 1.

In some embodiments, the method comprises administering an rHO-1 protein wherein the rHO-1 protein is truncated at residues corresponding to K226, A233, R237, T261, and/or A265.

In some embodiments, the method comprises administering an rHO-1 protein wherein the rHO-1 protein is truncated at residues corresponding to K226.

In some embodiments, the method comprises administering an rHO-1 protein wherein the rHO-1 protein comprises an amino acid sequence with at least 85% identity to residues 1-226 of SEQ ID NO:1.

In some embodiments, the method comprises administering an rHO-1 protein wherein the rHO-1 protein comprises an amino acid sequence with at least 90% identity to residues 1-226 of SEQ ID NO:1.

In some embodiments, the method comprises administering an rHO-1 protein wherein the rHO-1 protein comprises an amino acid sequence with at least 95% identity to residues 1-226 of SEQ ID NO:1.

In some embodiments, the method comprises administering an rHO-1 protein wherein the rHO-1 protein comprises an amino acid sequence identical to residues 1-226 of SEQ ID NO:1.

In some embodiments, the method comprises administering an rHO-1 protein wherein the rHO-1 protein comprises an amino acid substitution at a position corresponding to 33 of SEQ ID NO:1.

In some embodiments, the method comprises administering an rHO-1 protein wherein the rHO-1 protein comprises an F33L substitution.

In some embodiments, the method comprises administering an rHO-1 protein wherein rHO-1 protein comprises an Fc domain fused to an rHO-1 protein domain.

In some embodiments, the method comprises administering an rHO-1 protein wherein the N-terminus of the Fc domain is fused to the C-terminus of the THO-1 protein domain.

In some embodiments, the method comprises administering an rHO-1 protein wherein the C-terminus of the Fc domain is fused to the N-terminus of the rHO-1 protein domain.

In some embodiments, the method comprises administering an rHO-1 protein wherein the rHO-1 protein comprises a linker between the rHO-1 protein domain and the Fc domain.

In some embodiments, the linker comprises a sequence of GGGGS (SEQ ID NO: 10). In some embodiments, the linker comprises repeats of GGGGS (SEQ ID NO: 10). In some embodiments, the linker comprises 1, 2, 3, 4, or 5 repeats of GGGGS (SEQ ID NO: 61; "GGGGS" disclosed as SEQ ID NO: 10). In some embodiments, the linker comprises a sequence of (GGGGS) 4 (SEQ ID NO: 21).

In some embodiments, the method comprises administering an rHO-1 protein wherein the rHO-1 protein is a multimer comprising at least one monomer comprising an Fc domain fused to an rHO-1 protein domain.

In some embodiments, the method comprises administering an rHO-1 protein wherein the multimer is a dimer. In some embodiments, the multimer comprises a monomer comprising an Fc domain not fused to an rHO-1 protein domain.

In some embodiments, the method comprises administering an rHO-1 protein wherein the rHO-1 protein is a dimer with one monomer comprising an Fc domain fused to an rHO-1 protein domain and another monomer comprising an Fc domain not fused to an rHO-1 protein domain.

In some embodiments, the method comprises administering an rHO-1 protein wherein the Fc domain comprises one or more mutations to enhance half-life, reduce aggregation and/or reduce the effector function.

In some embodiments, the method comprises administering an rHO-1 protein wherein the one or more mutations comprise an amino acid substitution at one or more positions corresponding to 234, 235, 251, 252, 254, 255, 256, 308, 309, 311, 312, 314, 347, 349, 350, 351, 354, 360, 366, 385, 386, 387, 389, 392, 394, 399, 405, 405, 407, 409, 428, 433, 434, 435, and/or 436 of IgG1 Fc domain (according to EU numbering).

In some embodiments, the method comprises administering an rHO-1 protein wherein the one or more mutations comprises L234A and L235A amino acid substitutions of IgG1 Fc domain (according to EU numbering).

In some embodiments, the method comprises administering an rHO-1 protein wherein the one or more mutations comprise amino acid substitutions selected from L234A, L235A, Q347R, Y349C, T350V, L351Y, L351V, S354C, E356K, E357K, K360E, T366L, T366W, T366S, K370D, L368A, K392L, K392D, T394W, D399V, D399K, F405T, F405A, Y407V, K409W and K409D of IgG1 Fc domain (according to EU numbering).

In some embodiments, the method comprises administering an rHO-1 protein wherein the one or more mutations on one monomer chain comprises K360E, K409W and Y349C amino acid substitutions and on a second monomer chain, Q347R, D399V, F405T and S354C amino acid substitutions of IgG1 Fc domain (according to EU numbering).

In some embodiments, the method comprises administering an rHO-1 protein wherein the one or more mutations on one monomer chain comprises T350V, L351Y, F405A and Y407V amino acid substitutions and on a second monomer chain, T350V, T366L, K392L and T394W amino acid substitutions of IgG1 Fc domain (according to EU numbering).

In some embodiments, the method comprises administering an rHO-1 protein wherein the one or more mutations comprises K360E, K409W, Y349C, Q347R, D399V, F405T and S354C amino acid substitutions of IgG1 Fc domain (according to EU numbering).

In some embodiments, the method comprises administering an rHO-1 protein wherein the one or more mutations comprises T350V, L351Y, F405A, Y407V, T366L, K392L and T394W amino acid substitutions of IgG1 Fc domain (according to EU numbering).

In some embodiments, the method comprises administering an rHO-1 protein wherein the rHO-1 protein is administered intravenously. In some embodiments, the method comprises administering an rHO-1 protein wherein the rHO-1 protein is administered subcutaneously.

In some embodiments, the method comprises administering an rHO-1 protein wherein administering the rHO-1 protein results in a reduced free heme level in plasma compared to a control.

In some embodiments, the method comprises administering an rHO-1 protein wherein administering the rHO-1 protein results in a reduced free heme level in plasma to below about 1.0 mM, about 1.1 mM, about 1.2 mM, about 1.3 mM, about 1.4 mM, about 1.5 mM, about 1.6 mM, about 1.7 mM, about 1.8 mM, about 1.9 mM, about 2.0 mM, about 2.1 mM, about 2.2 mM, about 2.3 mM, about 2.4 mM, about 2.5 mM, about 2.6 mM, about 2.7 mM, about 2.8 mM, about 2.9 mM, about 3.0 mM. The method of any one of the preceding claims, wherein administering the rHO-1 protein results in a reduced free heme level in plasma to below about 12 mM, about 10 mM, about 8 mM, about 6 mM, about 4 mM or about 2 mM. The method of any one of the preceding claims, wherein administering the rHO-1 protein results in a reduced free heme level in plasma to below about 15 mM, about 10 mM, about 5 mM or about 1 mM. In some embodiments, administering the rHO-1 protein results in a reduced free heme level in plasma to below about 10 mM.

In some embodiments, the method comprises administering an rHO-1 protein wherein administering the rHO-1 protein results in an increased HO-1 activity in plasma compared to a control.

In some embodiments, the method comprises administering an rHO-1 protein wherein administering the rHO-1 protein results in an HO-1 activity in plasma at or above 10% of a normal serum HO-1 activity in a healthy individual. In some embodiments, administering the rHO-1 protein results in an HO-1 activity in plasma at or above 12% of a normal serum HO-1 activity in a healthy individual. In some embodiments, administering the rHO-1 protein results in an HO-1 activity in plasma at or above 15% of a normal serum HO-1 activity in a healthy individual. In some embodiments, administering the rHO-1 protein results in an HO-1 activity in plasma at or above 20% of a normal serum HO-1 activity in a healthy individual. In some embodiments, administering the rHO-1 protein results in an HO-1 activity in plasma at or above 25% of a normal serum HO-1 activity in a healthy individual.

In some embodiments, the method comprises administering an rHO-1 protein wherein administering the rHO-1 protein results in reduced or delayed onset of one or more symptoms including anemia, vasoocclusive crises (VOC), acute chest syndrome (ACS), pulmonary hypertension, or organ damage.

In one aspect, the present invention provides, a recombinant heme oxygenase-1 (rHO-1) protein comprising an rHO-1 protein domain fused to an Fc domain.

In some embodiments, the C-terminus of the rHO-1 protein domain is fused to the N-terminus of the Fc domain. In some embodiments, the N-terminus of the rHO-1 protein domain is fused to the C-terminus of the Fc domain.

In some embodiments, the rHO-1 protein comprises a linker between the rHO-1 protein domain and the Fc domain.

In some embodiments, the linker comprises a sequence of GGGGS (SEQ ID NO: 10). In some embodiments, the linker comprises repeats of GGGGS (SEQ ID NO: 10). In some embodiments, the linker comprises 1, 2, 3, 4, or 5 repeats of GGGGS (SEQ ID NO: 61; "GGGGS" disclosed as SEQ ID NO: 10). In some embodiments, the linker comprises a sequence of (GGGGS) 4 (SEQ ID NO: 21).

In some embodiments, the rHO-1 protein is a multimer comprising at least one monomer comprising an Fc domain fused to an rHO-1 protein domain.

In some embodiments, the multimer is a dimer. In some embodiments, the multimer comprises a monomer comprising an Fc domain not fused to an rHO-1 protein domain.

In some embodiments, the rHO-1 protein is a dimer with one monomer comprising an Fc domain fused to an rHO-1 protein domain and another monomer comprising an Fc domain not fused to an rHO-1 protein domain.

In some embodiments, wherein the rHO-1 protein domain comprises an amino acid sequence with at least 85% identity to residues 1-261 of SEQ ID NO:1 (wild type full length rHO-1 protein).

In some embodiments, the rHO-1 protein domain comprises an amino acid sequence with at least 90% identity to residues 1-261 of SEQ ID NO:1 (wild type full length rHO-1 protein).

In some embodiments, the rHO-1 protein domain comprises an amino acid sequence with at least 95% identity to residues 1-261 of SEQ ID NO:1 (wild type full length rHO-1 protein).

In some embodiments, the rHO-1 protein domain comprises an amino acid sequence identical to residues 1-261 of SEQ ID NO:1 (wild type full length rHO-1 protein).

In some embodiments, the rHO-1 protein domain comprises SEQ ID NO:1.

In some embodiments, the rHO-1 protein domain comprises K18, T21, H25, Y134, G143, L147, K179, and F207 of SEQ ID NO: 1.

In some embodiments, wherein the rHO-1 protein is truncated at the N-terminal at the residue corresponding to M9. In some embodiments, the rHO-1 protein comprises residues 10-225 of SEQ ID NO: 1. In some embodiments, the rHO-1 protein comprises residues 10-226 of SEQ ID NO: 1. In some embodiments, the rHO-1 protein comprises residues 10-261 of SEQ ID NO: 1.

In some embodiments, the rHO-1 protein domain further comprises K226, A233, R237, T261, and A265.

In some embodiments, the rHO-1 protein is truncated at a residue corresponding to K226.

In some embodiments, the rHO-1 protein comprises an amino acid sequence with at least 85% identity to residues 1-226 of SEQ ID NO:1.

In some embodiments, the rHO-1 protein comprises an amino acid sequence with at least 90% identity to residues 1-226 of SEQ ID NO:1.

In some embodiments, the rHO-1 protein comprises an amino acid sequence with at least 95% identity to residues 1-226 of SEQ ID NO:1.

In some embodiments, the rHO-1 protein comprises an amino acid sequence identical to residues 1-226 of SEQ ID NO:1.

In some embodiments, the rHO-1 protein domain comprises an amino acid substitution at a position corresponding to 33 of SEQ ID NO:1.

In some embodiments, the rHO-1 protein domain comprises an F33L substitution.

In some embodiments, the Fc domain comprises one or more mutations to enhance half-life, reduce aggregation and/or reduce the effector function.

In some embodiments, the one or more mutations comprise an amino acid substitution at one or more positions corresponding to 234, 235, 251, 252, 254, 255, 256, 308, 309, 311, 312, 314, 385, 386, 387, 389, 428, 433, 434, 435, and 436 of IgG1 Fc domain (according to EU numbering).

In some embodiments, the one or more mutations comprises L234A and L235A amino acid substitutions of IgG1 Fc domain (according to EU numbering).

In some embodiments, the one or more mutations on one chain comprises K360E, K409W and Y349C amino acid substitutions and on a second chain, Q347R, D399V, F405T and S354C amino acid substitutions of IgG1 Fc domain (according to EU numbering).

In some embodiments, the one or more mutations on one chain comprises T350V, L351Y, F405A and Y407V amino acid substitutions and on a second chain, T350V, T366L, K392L and T394W amino acid substitutions of IgG1 Fc domain (according to EU numbering).

In some embodiments, the one or more mutations on one chain comprises K360E, K409W, Y349C, Q347R, D399V, F405T and S354C amino acid substitutions of IgG1 Fc domain (according to EU numbering).

In some embodiments, the one or more mutations on one chain comprises T350V, L351Y, F405A, Y407V, T366L, K392L and T394W amino acid substitutions of IgG1 Fc domain (according to EU numbering).

In one aspect, the present invention provides a nucleic acid encoding a recombinant heme oxygenase-1 (rHO-1) protein described herein.

In one aspect, the present invention provides a cell comprising a nucleic acid encoding a recombinant heme oxygenase-1 (rHO-1) protein described herein.

Definitions

In order for the present invention to be more readily understood, certain terms are first defined below. Additional definitions for the following terms and other terms are set forth throughout the specification.

A or An: The articles "a" and "an" are used herein to refer to one or to more than one (i.e., to at least one) of the grammatical object of the article. By way of example, "an element" means one element or more than one element.

Amelioration: As used herein, the term "amelioration" is meant the prevention, reduction or palliation of a state, or improvement of the state of a subject. Amelioration includes, but does not require, complete recovery or complete prevention of a disease condition.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: Two events or entities are "associated" with one another, as that term is used herein, if the presence, level and/or form of one is correlated with that of the other. For example, a particular entity (e.g., polypeptide) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Bioavailability: As used herein, the term "bioavailability" generally refers to the percentage of the administered dose that reaches the blood stream of a subject.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a peptide is biologically active, a portion of that peptide that shares at least one biological activity of the peptide is typically referred to as a "biologically active" portion.

Binding Moiety: As used herein, a "binding moiety" is any molecule or part of a molecule capable of specifically binding a target, e.g., a target of interest (e.g., FcR, FcRn). Binding moieties include, e.g., antibodies, antigen binding fragments thereof, Fc regions or Fc fragments thereof, antibody mimetics, peptides, and aptamers.

Constant region: As used herein, the term "constant region" refers to a polypeptide that corresponds to, or is derived from, one or more constant region immunoglobulin domains of an antibody. A constant region can include any or all of the following immunoglobulin domains: a CH1 domain, a hinge region, a CH2 domain, a CH3 domain (derived from an IgA, IgD, IgG, IgE, or IgM), and a CH4 domain (derived from an IgE or IgM).

Fc region: As used herein, the term "Fc region" refers to a dimer of two "Fc polypeptides", each "Fc polypeptide" comprising the constant region of an antibody excluding the first constant region immunoglobulin domain. In some embodiments, an "Fc region" includes two Fc polypeptides linked by one or more disulfide bonds, chemical linkers, or peptide linkers. "Fc polypeptide" refers to the last two constant region immunoglobulin domains of IgA, IgD, and IgG, and the last three constant region immunoglobulin domains of IgE and IgM, and may also include part or all of the flexible hinge N-terminal to these domains. For IgG, "Fc polypeptide" comprises immunoglobulin domains Cgamma2 (Cγ2) and Cgamma3 (Cγ3) and the lower part of the hinge between Cgamma1 (Cγ1) and Cγ2. Although the boundaries of the Fc polypeptide may vary, the human IgG heavy chain Fc polypeptide is usually defined to comprise residues starting at T223 or C226 or P230, to its carboxyl-terminus, wherein the numbering is according to the EU index as in Kabat et al. (1991, NIH Publication 91-3242, National Technical Information Services, Springfield, VA). Unless otherwise specified, numbering of Fc domain residues are according to EU numbering. For IgA, Fc polypeptide comprises immunoglobulin domains Calpha2 (Cα2) and Calpha3 (Cα3) and the lower part of the hinge between Calpha1 (Cα1) and Cα2. An Fc region can be synthetic, recombinant, or generated from natural sources such as IVIG.

Functional equivalent or derivative: As used herein, the term "functional equivalent" or "functional derivative" denotes, in the context of a functional derivative of an amino acid sequence, a molecule that retains a biological activity (either function or structural) that is substantially similar to that of the original sequence. A functional derivative or equivalent may be a natural derivative or is prepared synthetically. Exemplary functional derivatives include amino acid sequences having substitutions, deletions, or additions of one or more amino acids, provided that the biological activity of the protein is conserved. The substituting amino acid desirably has chemico-physical properties which are similar to that of the substituted amino acid. Desirable similar chemico-physical properties include, similarities in charge, bulkiness, hydrophobicity, hydrophilicity, and the like.

Fusion protein: As used herein, the term "fusion protein" or "chimeric protein" refers to a protein created through the joining of two or more originally separate proteins, or portions thereof. In some embodiments, a linker or spacer will be present between each protein. A non-limiting example of a fusion protein is an Fc-fusion protein. A non-limiting example of a fusion protein is a heme oxygenase 1 (HO-1)-Fc fusion protein.

Half-Life: As used herein, the term "half-life" is the time required for a quantity such as protein concentration or activity to fall to half of its value as measured at the beginning of a time period.

Heme oxygenase or recombinant heme oxygenase: As used herein, the term "heme oxygenase (HO)", "recombinant heme oxygenase", "HO-1" or "rHO-1"refers to any wild-type or modified heme oxygenase proteins or polypeptides (e.g., heme oxygenase proteins with amino acid mutations, deletions, insertions, and/or fusion proteins) that retain substantial heme oxygenase biological activity unless otherwise specified.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

Inhibition: As used herein, the terms "inhibition," "inhibit" and "inhibiting" refer to processes or methods of decreasing or reducing activity and/or expression of a protein or a gene of interest. Typically, inhibiting a protein or a gene refers to reducing expression or a relevant activity of the protein or gene by at least 10% or more, for example, 20%, 30%, 40%, or 50%, 60%, 70%, 80%, 90% or more, or a decrease in expression or the relevant activity of greater than 1-fold, 2-fold, 3-fold, 4-fold, 5-fold, 10-fold, 50-fold, 100-fold or more as measured by one or more methods described herein or recognized in the art.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

$K_a$: As used herein, "$K_a$" refers to an association rate of a particular binding moiety and a target to form a binding moiety/target complex.

$K_d$: As used herein, "$K_d$" refers to a dissociation rate of a particular binding moiety/target complex.

$K_D$: As used herein, "$K_D$" refers to a dissociation constant, which is obtained from the ratio of $K_d$ to $K_a$ (i.e., $K_d/K_a$) and is expressed as a molar concentration (M). $K_D$ values can be determined using methods well established in the art, e.g., by using surface plasmon resonance, or using a biosensor system such as a Biacore® system.

Linker: As used herein, the term "linker" refers to, in a fusion protein, an amino acid sequence other than that appearing at a particular position in the natural protein and is generally designed to be flexible or to interpose a structure, such as an α-helix, between two protein moieties. A linker is also referred to as a spacer. A linker or a spacer typically does not have biological function on its own.

Polypeptide: The term "polypeptide" as used herein refers to a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified. As used herein, the terms "polypeptide" and "peptide" are used inter-changeably.

Prevent: As used herein, the term "prevent" or "prevention", when used in connection with the occurrence of a disease, disorder, and/or condition, refers to reducing the risk of developing the disease, disorder and/or condition. See the definition of "risk."

Protein: The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" refers to the multiple polypeptides that are physically coupled and function together as the discrete unit.

Reference: A "reference" entity, system, amount, set of conditions, etc., is one against which a test entity, system, amount, set of conditions, etc. is compared as described herein. For example, in some embodiments, a "reference" antibody is a control antibody that is not engineered as described herein.

Subject: The term "subject", as used herein, means any subject for whom diagnosis, prognosis, or therapy is desired. For example, a subject can be a mammal, e.g., a human or non-human primate (such as an ape, monkey, orangutan, or chimpanzee), a dog, cat, guinea pig, rabbit, rat, mouse, horse, cattle, or cow. In particular embodiments, the term "subject" refers to a human patient, e.g., a child, adolescent or adult.

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215 (3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215 (3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Target: As used herein, a "target" is any molecule specifically bound by a binding moiety of a multi-specific binding molecule. In some embodiments, a target is an FcR (e.g., FcRn). The terms "first target" and "second target" are used herein to refer to molecules of two distinct molecular species, rather than two molecules of the same molecular species. For example, in some embodiments, a first target is a serum protein and a second target is FcRn.

Therapeutically effective amount: As used herein, the term "therapeutically effective amount" refers to an amount of a therapeutic molecule (e.g., an engineered antibody described herein) which confers a therapeutic effect on a treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic molecule or composition effective to treat, ameliorate, or prevent a particular disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount can be administered in a dosing regimen that may comprise multiple unit doses. For any particular therapeutic molecule, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular subject may depend upon a variety of factors including the disorder being treated and the severity of the disorder; the activity of the specific pharmaceutical agent employed; the specific composition employed; the age, body weight, general health, sex and diet of the subject; the time of administration, route of administration, and/or rate of excretion or metabolism of the specific therapeutic molecule employed; the duration of the treatment; and like factors as is well known in the medical arts.

Treatment: As used herein, the term "treatment" (also "treat" or "treating") refers to any administration of a therapeutic molecule (e.g., an engineered antibody described herein) that partially or completely alleviates, ameliorates, relieves, inhibits, delays onset of, reduces severity of and/or reduces incidence of one or more symptoms or features of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

BRIEF DESCRIPTION OF THE DRAWING

Drawings are for illustration purposes only; not for limitation.

DETAILED DESCRIPTION

Figure 1B:
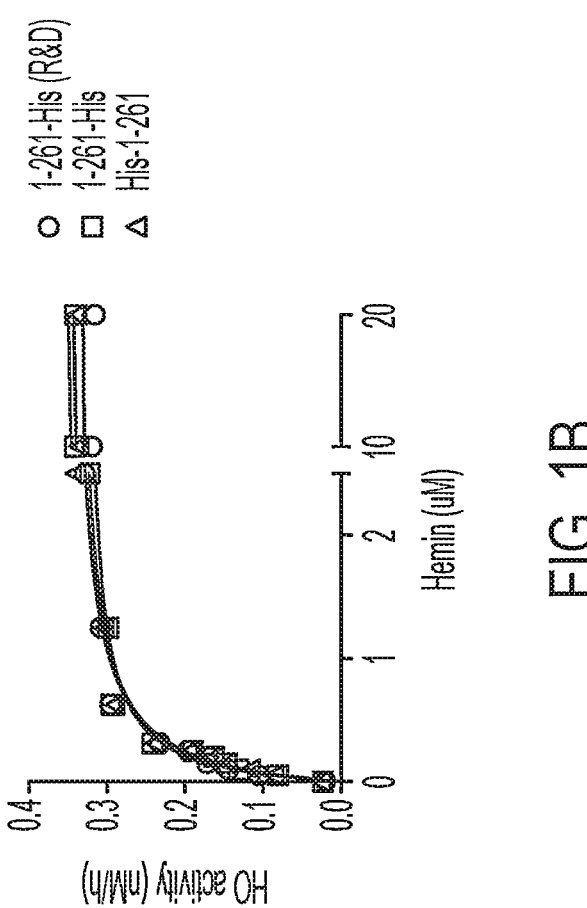
FIG. 1B shows exemplary results of heme oxygenase enzyme kinetics of 1-261-His and His-1-261 relative to 1-261-His (R&D) on a hemin substrate.

The present invention provides, among other things, methods and compositions for treating sickle cell disease, using recombinant heme oxygenase-1 (HO-1) as a protein therapeutic. In some embodiments, administration of recombinant heme oxygenase may ameliorate symptoms of sickle cell disease in acute cases. In some embodiments, administration of recombinant heme oxygenase may provide a treatment modality for long-term prophylaxis.

Various aspects of the invention are described in detail in the following sections. The use of sections is not meant to limit the invention. Each section can apply to any aspect of the invention. In this application, the use of "or" means "and/or" unless stated otherwise.

Sickle Cell Disease

Sickle cell disease (SCD) is a hemolytic disease caused by a single base pair substitution in the β-globin gene on chromosome 11, resulting in an amino acid switch from glutamic acid to valine. in position six of the β-globin chain of hemoglobin. This results in polymerization of deoxygenated hemoglobin through hydrophobic interactions with other hemoglobin molecules forming rigid polymer aggregates within red blood cells (hemoglobin S), distorting their shape, shortening their lifespan from 120 days to 15 days and promoting intravascular hemolysis. When erythrocytes are lysed, extracellular hemoglobin (Hb) is released and oxidized from $Fe^{2+}$ to ferric $Fe^{3+}$ hemoglobin (methemoglobin) which releases heme into the circulation. Oxidation of Hb releases extracellular heme, promotes vascular inflammation and damage in SCD, including painful vaso-occlusive crises (VOC) and Acute Chest Syndrome (ACS). Heme levels in patients with severe symptoms could be up to 2.2 mM. (Ghosh et al., 2013 *J Clin Invest.* 2013; 123 (11): 4809-4820).

Intravascular hemolysis in SCD patients cause oxidative damage and trigger an inflammatory cascade. Free heme increases expression of endothelial adhesion molecules and apoptotic markers, promoting attachment of activated leukocytes and RBCs to the vessel wall. Chronic hemolysis may lead to depressed red blood cell counts and anemia. Chronic anemia may lead to myocardial infarction and increased cardiac output. Infarction may lead to bone necrosis and joint destruction.

Vasoocclusion may lead to leg ulcers and myofascial syndrome, and results in stroke in about 25% of patients by age 45. SCD patients suffer complications such as vaso-occlusive crises (VOC) characterized by severe pain, caused by vascular occlusion resulting from attachment of rigid sickle RBCs, activated leukocytes, and possibly platelets to the underlying activated, damaged vascular endothelium.

Fat embolism or bone ischemia may lead to Acute Chest Syndrome (ACS). Acute chest syndrome (ACS) is a major pulmonary complication of sickle cell disease (SCD). It is typically preceded by acute vaso-occlusive crisis and acute hemolysis. ACS diagnosis is associated with decreasing hemoglobin (Hb) concentration, hypoxemia, and multilobular lung infiltration. Lung injury in ACS is characterized predominantly by edema formation. Danger-associated molecular pattern molecules derived from the lysis of erythrocytes may ultimately contribute to lung injury in ACS. Hemin (the oxidized prosthetic moiety of Hb) is a potent inflammatory agonist and activator of TLR4. Hemolysis inevitably results in the release of hemin into the extracellular space. This process is likely to be accelerated in SCD because of the enhanced auto-oxidation of sickle-cell oxyhemoglobin and the presence of free hemin at high concentrations (~1 μM) inside sickle erythrocytes. Hemin has been shown to induce ACS in a mouse model.

Liver ischemia can lead to hepatic dysfunction. Renal failure can occur in about 20% of SCD patients. Impaired splenic function results in a high incidence of infection. Organ damage is a key cause of death is SCD patients. Opioids (e.g. morphine, hydromorphone, fentanyl) are commonly utilized to manage VOC pain in the U.S., which carry addictive risks and significant side effects.

In newborns, red blood cells contain large proportion of fetal hemoglobin, hemoglobin F which binds to oxygen with greater affinity than adult hemoglobin. After birth, adult hemoglobin, Hemoglobin A expression increases. In children with sickle cell anemia, defective hemoglobin S is produced and continues into adulthood. Due to an elevated fetal hemoglobin level at birth, patients typically do not exhibit signs of sickle cell disease until 6 months after birth. Other than vaso-occlusion, common symptoms of SCD are manifested as fatigue, exercise intolerance, and shortness of breath due to anemia. Pediatric patients may experience delayed growth and fever, while adults may present with ulcers or bone injury. Other symptoms include jaundice, frequent urination, and muscle weakness.

HO-1 gene promoter polymorphism linked with increased HO-1 activity is associated with reduced incidence of ACS among children with SCD (Bean et al., 2012). Children with multiple ACS episodes have significantly higher plasma heme levels in comparison to age-matched counterparts with no history of ACS (Adisa et al., 2013). This can lead to acute hemolysis, severe hypoxemia, and massive infiltration in lung. Biomarkers such as impact on arterial oxygen saturation (% SpO2), hemoglobin (Hb), total plasma heme (TPH), and bilirubin levels, lung-weight, histopathology and vaso-occlusion may be used in diagnosis. Only two SCD disease-modifying oral therapies, hydroxyurea (HU) and Endari® (L-glutamine) are approved, and alternative long-term blood transfusions are the only option. Hydroxyurea was originally approved by the FDA only in adults in 1998, and for children over 2 years in December 2017. This helps red blood cells retain their shape and flexibility, reducing complications and the need for frequent transfusions. Common side effects of hydroxyurea include low blood counts, gastrointestinal symptoms, and loss of appetite. In addition, effectiveness of prophylactic hydroxyurea is limited by poor patient adherence due to variable effectiveness, side effects, and toxicity requiring frequent blood count monitoring. Endari® (L-glutamine) was approved in July 2017 for patients 5 years and older to reduce acute complications of SCD, including sudden, severe pain called sickle cell crises. Common side-effects of Endari® include constipation, nausea, headache, abdominal pain, cough, pain in the extremities, back pain and chest pain. Prophylaxis using L-glutamine has only modest clinical effect. Voxelotor has been approved for treatment of anemia, but it does not reduce incidence of VOCs. Crizanlizumab requires monthly IV infusion that may result in poor adherence. Bone marrow or stem cell transplants may be an option for younger patients with severe SCD, but this necessitates finding a matching bone marrow or stem cell donor and the associated risks of transplant surgery can be serious and potentially life-threatening. Regular blood transfusions are used frequently to treat anemia and prevent long-term complications. There is a need in the art for developing therapeutic molecules to treat patients having sickle cell disease and experiencing VOC.

Recombinant Heme Oxygenase-1

Heme oxygenase protects the endothelium and tissues against hemolysis and oxidative stress. Inducing HO-1 expression may protect tissues and cells against ischemia, oxidative stress, inflammation, transplant rejection, apoptosis and cell proliferation. Heme oxygenase 1 (HO-1) plays an important role in heme detoxification by degrading heme into iron, carbon monoxide, and biliverdin. HO-1 specifically targets and degrades free heme to cytoprotective/anti-inflammatory by-products. Because rHO-1 is based on an endogenous protein it may significantly minimize off-target effects.

In some embodiments, as used herein, recombinant heme oxygenase proteins suitable for the present invention include any wild-type and modified heme oxygenase proteins (e.g., heme oxygenase proteins with amino acid mutations, deletions, insertions, and/or fusion proteins) that retain substantial heme oxygenase biological activity. Typically, a recombinant heme oxygenase protein is produced using recombinant technology. However, heme oxygenase proteins (wild-type or modified) purified from natural resources or synthesized chemically can be used according to the present invention.

In some embodiments, a suitable recombinant heme oxygenase protein or a recombinant heme oxygenase fusion protein has an in vivo half-life of or greater than about 1 minute, 2 minutes, 10 minutes, 15 minutes, 30 minutes, 60 minutes, 70 minutes, 80 minutes, 90 minutes, 100 minutes, 2 hours, 3 hours, 4 hours, 5 hours, 6 hours, 7 hours, 8 hours, 9 hours, 10 hours, 12 hours, or 24 hours. In some embodiments, a suitable recombinant heme oxygenase protein or a recombinant heme oxygenase fusion protein has an in vivo half-life of or greater than about greater than about 24 hours, 30 hours, 36 hours, 42 hours, 48 hours, 54 hours, or 60 hours. In some embodiments, a recombinant heme oxygenase protein has an in vivo half-life of between 0.5 and 24 hours, between 1 day and 10 days, between 1 day and 9 days, between 1 day and 8 days, between 1 day and 7 days, between 1 day and 6 days, or between 1 day and 5 days.

In some embodiments, presented herein are engineered recombinant heme oxygenase variants. In some embodiments, the engineered recombinant HO variants are fused to IgG Fc. In some embodiments, the engineered recombinant HO variants are fused to human IgG1 Fc.

In some embodiments, recombinant heme oxygenase protein described herein comprises SEQ ID NO: 1.

```
                                    (SEQ ID NO: 1)
MERPQPDSMPQDLSEALK₁₈EAT₂₁KEVH₂₅TQAENAEFMRN

FQKGQVTRDGFKLVMASLYHIYVALEEEIERNKESPVFAPVY

FPEELHRKAALEQDLAFWYGPRWQEVIPYTPAMQRYVKRLHE

VGRTEPELLVAHAY₁₃₄TRYLGDLSG₁₄₃GQVL₁₄₇KKIAQK

ALDLPSSGEGLAFFTFPNIASATKFK₁₇₉QLYRSRMNSLEMT

PAVRQRVIEEAKTAF₂₀₇LLNIQLFEELQELLTHDTK226DQ

S229PSRA233PGLR237QRASNKVQDSAPVETPRGKPPLN

T261RSQA265PLLRWVLTLSFLVATVAVGLYAM.
```

In some embodiments, the recombinant HO-1 comprises a heme binding pocket comprising residues 18, 21, 25, 134, 143, 147, 179, 207 of SEQ ID NO: 1. In some embodiments, the recombinant HO-1 is phosphorylated at residue S229 of SEQ ID NO: 1. In some embodiments, the recombinant HO-1 comprises a substitution at residue 261 to facilitate *E coli* expression. In some embodiments, residue 261 is a Threonine (T). In some embodiments, the recombinant HO-1 is truncated HO-1 expression at residues $K_{226}$, $A_{233}$. $R_{237}$. $A_{265}$. In some embodiments, recombinant HO-1 comprises an endoplasmic reticulum (ER) membrane binding region. In some embodiments, the ER membrane binding region comprises the amino acid sequence PLLRWVLTLSFLVATVAVGLYAM (SEQ ID NO: 40).

In some embodiments, recombinant heme oxygenase protein described herein comprises SEQ ID NO: 2.

(SEQ ID NO: 2)
MERPQPDSMPQDLSEALK$_{18}$EAT$_{21}$KEVH$_{25}$TQA

ENAEFMRNFQKGQVTRDGFKLVMASLYHIYVALE

EEIERNKESPVFAPVYFPEELHRKAALEQDLAFW

YGPRWQEVIPYTPAMQRYVKRLHEVGRTEPELLV

AHAY$_{134}$TRYLGDLSG$_{143}$GQVL$_{147}$KKIAQKALDL

PSSGEGLAFFTFPNIASATKFK$_{179}$QLYRSRMNS

LEMTPAVRQRVIEEAKTAF$_{207}$LLNIQLFEELQE

LLTHDTK$_{226}$DQS$_{229}$PSRA$_{233}$PGLR$_{237}$QRAS

NKVQDSAPVETPRGKPPLNT$_{261}$

HHHHHH.

In some embodiments, recombinant heme oxygenase protein described herein comprises SEQ ID NO: 3.

(SEQ ID NO: 3)
MERPQPDSMPQDLSEALK$_{18}$EAT$_{21}$KEVH$_{25}$TQA

ENAEFMRNFQKGQVTRDGFKLVMASLYHIYVALE

EEIERNKESPVFAPVYFPEELHRKAALEQDLAFW

YGPRWQEVIPYTPAMQRYVKRLHEVGRTEPELLV

AHAY$_{134}$TRYLGDLSG$_{143}$GQVL$_{147}$KKIAQKALDL

PSSGEGLAFFTFPNIASATKFK$_{179}$QLYRSRMNS

LEMTPAVRQRVIEEAKTAF$_{207}$LLNIQLFEELQE

LLTHDTK$_{226}$DQS$_{229}$PSRA$_{233}$PGLR$_{237}$QRAS

NKVQDSAPVETPRGKPPLNT$_{261}$.

In some embodiments, recombinant heme oxygenase comprises a sequence at least 70%, 80%, 85%, 90%, 95%, 97%, 98%, 99% sequence identity to SEQ ID NO: 1, SEQ ID NO: 2 or SEQ ID NO: 3.

In some embodiments, recombinant heme oxygenase comprises truncated HO-1, wherein the HO-1 comprises residues selected from the group consisting of 1-226, 1-229, 1-233, 1-239 and 1-265 of SEQ ID NO: 1. A truncated HO-1 lacking the ER membrane binding region is especially useful for the therapeutic application disclosed here. For example, a truncated HO-1 comprising residues 1-226 of SEQ ID NO: 1 or 1-261 of SEQ ID NO: 1 is suitable for practicing the claimed invention.

In some embodiments, recombinant heme oxygenase comprises truncated HO-1 comprising N-terminal deletions of about 1, 2, 3, 4, 5, 6, 7, 8, 9 or 10 residues of SEQ ID NO: 1.

In some embodiments, recombinant heme oxygenase comprises truncated HO-1 comprising C-terminal deletions of about 1, 2, 3, 4, 5, 6, 7, 8, 9 or 10 residues of SEQ ID NO: 1.

In some embodiments, recombinant heme oxygenase comprises truncated HO-1 comprising residues 10-225 of SEQ ID NO: 1. In some embodiments, recombinant heme oxygenase comprises truncated HO-1 comprising residues 10-226 of SEQ ID NO: 1. In some embodiments, recombinant heme oxygenase comprises truncated HO-1 comprising residues 10-261 of SEQ ID NO: 1. In some embodiments, recombinant heme oxygenase comprises truncated HO-1 selected from a group consisting of residues 10-226, 10-229, 10-233, 10-239 and 10-265.

In some embodiments, recombinant heme oxygenase protein comprises amino acid residues comprising K18, T21, H25, Y134, G143, L147, K179 and/or F207 (according to SEQ ID NO:1). In some embodiments, recombinant heme oxygenase protein comprises amino acid residues comprising K18, T21, H25, Y134, G143, L147, K179, F207 and further comprises K226, A233, R237, T261, and/or A265 (according to SEQ ID NO:1). In some embodiments, recombinant heme oxygenase protein comprises one or more an amino acid substitutions wherein the amino acid substitution is F33L (according to SEQ ID NO: 1).

HO-1 Fusion Proteins

It is contemplated that a suitable recombinant HO-1 protein can be in a fusion protein configuration. For example, a recombinant HO-1 protein suitable for the present invention may be a fusion protein between a HO-1 domain and another domain or moiety that typically can facilitate a therapeutic effect of HO-1 by, for example, enhancing or increasing stability, potency and/or delivery of HO-1 protein, or reducing or eliminating immunogenicity, or clearance. Such suitable domains or moieties for a HO-1 fusion protein include but are not limited to Fc domain, XTEN domain, or human albumin fusions.

Fc Domain

In some embodiments, a suitable recombinant HO-1 protein comprises an Fc domain or a portion thereof that binds to the FcRn receptor. As a non-limiting example, a suitable Fc domain may be derived from an immunoglobulin subclass such as IgG. In some embodiments, a suitable Fc domain is derived from IgG1, IgG2, IgG3, or IgG4. In some embodiments, a suitable Fc domain is derived from IgM, IgA, IgD, or IgE. Particularly suitable Fc domains include those derived from human or humanized antibodies. In some embodiments, a suitable Fc domain is a modified Fc portion, such as a modified human Fc portion.

In some embodiments, a suitable Fc domain comprises an amino acid sequence as provided in Table 1.

TABLE 1

| Exemplary Fc domains |
| --- |

| Sequence ID No. (description) | Fc Domain* |
| --- | --- |
| SEQ ID NO: 15 (wild-type human IgG1 Fc) | DKTHTCPPCPAPELLGGPSVFLFPPKPKDTLMISRTPEVTCVVVDVSHEDPEVKFNWYVD GVEVHNAKTKPREEQYNSTYRVVSVLTVLHQDWLNGKEYKCKVSNKALPAPIEKTISKAK GQPREPQVYTLPPSRDELTKNQVSLTCLVKGFYPSDIAVEWESNGQPENNYKTTPPVLDS DGSFFLYSKLTVDKSRWQQGNVFSCSVMHEALHNHYTQKSLSLSPGK |

TABLE 1-continued

Exemplary Fc domains

Sequence ID No.
(description)      Fc Domain*

SEQ ID NO: 16     DKTHTCPPCPAPEAAGGPSVFLFPPKPKDTLMISRTPEVTCVVVDVSHEDPEVKFNWYVD
(human IgG1 Fc-   GVEVHNARTKPREEQYNSTYRVVSVLTVLHQDWLNGKEYKCKVSNKALPAPIEKTISKAK
LALA)             GQPREPQVYTLPPSRDELTKNQVSLTCLVKGFYPSDIAVEWESNGQPENNYKTTPPVLDS
                  DGSFFLYSKLTVDKSRWQQGNVFSCSVMHEALHNHYTQKSLSLSPGK SEQ ID NO: 17     DKTHTCPPCPAPELLGGPSVFLFPPKPKDTLMISRTPEVTCVVVDVSHEDPEVKFNWYVD
(human IgG1 Fc-   GVEVHNAKTKPREEQYNSTYRVVSVLTVLHQDWLNGKEYKCKVSNKALPAPIERTISKAK
NHance)           GQPREPQVYTLPPSRDELTKNQVSLTCLVKGFYPSDIAVEWESNGQPENNYKTTPPVLDS
                  DGSFFLYSKLTVDKSRWQQGNVFSCSVMHEALKFHYTQKSLSLSPGK SEQ ID NO: 18     DKTHTCPPCPAPEAAGGPSVFLFPPKPKDTLMISRTPEVTCVVVDVSHEDPEVKFNWYVD
(human IgG1 Fc-   GVEVHNAKTKPREEQYNSTYRVVSVLTVLHQDWLNGKEYKCKVSNKALPAPIERTISKAK
LALA + NHance)    GQPREPQVYTLPPSRDELTKNQVSLTCLVKGFYPSDIAVEWESNGQPENNYKTTPPVLDS
                  DGSFFLYSKLTVDKSRWQQGNVFSCSVMHEALKFHYTQKSLSLSPGK SEQ ID NO: 19     EPKSCDKTHTCPPCPAPELLGGPSVFLFPPKPKDTLMISRTPEVTCVVVDVSHEDPEVKF
                  NWYVDGVEVHNAKTKPREEQYNSTYRVVSVLTVLHQDWLNGKEYKCKVSNKALPAPIEKT
                  ISKAKGQPREPQVYTLPPSRDELTKNQVSLTCLVKGFYPSDIAVEWESNGQPENNYKTTP
                  PVLDSDGSFFLYSKLTVDKSRWQQGNVFSCSVMHEALHNHYTQKSLSLSPGK SEQ ID NO: 20     KTHTCPPCPAPELLGGPSVFLFPPKPKDTLMISRTPEVTCVVVDVSHEDPEVKFNWYVDG
                  VEVHNAKTKPREEQYNSTYRVVSVLTVLHQDWLNGKEYKCKVSNKALPAPIEKTISKAKG
                  QPREPQVYTLPPSRDELTKNQVSLTCLVKGFYPSDIAVEWESNGQPENNYKTTPPVLDSD
                  GSFFLYSKLTVDKSRWQQGNVFSCSVMHEALHNHYTQKSLSLSPGK

*LALA and NHance mutations are underlined.

In some embodiments, a suitable Fc domain comprises an amino acid sequence at least 50%, 55%, 60%, 65%, 70%, 75%, 80%, 85%, 90%, 91%, 92%, 93%, 94%, 95%, 96%, 97%, 98%, 99% or more homologous or identical to SEQ ID NO: 15, SEQ ID NO: 16, SEQ ID NO:17, SEQ ID NO: 18, SEQ ID NO: 19 or SEQ ID NO:20.

It is contemplated that improved binding between the Fc domain and the FcRn receptor results in prolonged serum half-life of the recombinant protein. Thus, in some embodiments, a suitable Fc domain comprises one or more amino acid mutations that lead to improved binding to FcRn. Various mutations within the Fc domain that effect improved binding to FcRn are known in the art and can be adapted to practice the present invention. In some embodiments, a suitable Fc domain comprises one or more mutations at one or more positions corresponding to Thr 250, Met 252, Ser 254, Thr 256, Thr 307, Glu 380, Met 428, His 433 and/or Asn 434 of human IgG1, according to EU numbering.

In some embodiments, a suitable Fc domain comprises one or more mutations at one or more positions corresponding to L234, L235, H433 and N434 of human IgG1, according to EU numbering.

The Fc portion of a recombinant fusion protein may lead to targeting of cells that express Fc receptors leading to pro-inflammatory effects. Some mutations in the Fc domain reduce binding of the recombinant protein to the Fc gamma receptor and thereby inhibit effector functions. In one embodiment, effector function is antibody-dependent cell-mediated cytotoxicity (ADCC). For example, a suitable Fc domain may contain mutations of L234A (Leu234Ala) and/or L235A (Leu235Ala) (EU numbering). In some embodiments the L234A and L235A mutations are also referred to as the LALA mutations. As a non-limiting example, a suitable Fc domain may contain mutations L234A and L235A (EU numbering). An exemplary Fc domain sequence comprising the L234A and L235A mutations is shown as SEQ ID NO: 16 in Table 1.

In some embodiments, a suitable Fc domain may contain mutations of H433K (His433Lys) and/or N434F (Asn434Phe) (EU numbering). As a non-limiting example, a suitable Fc domain may contain mutations H433K and N434F (EU numbering). In some embodiments the H433K and N434F mutations are also referred to as the NHance mutations. An exemplary Fc domain sequence incorporating the mutations H433K and N434F is shown as SEQ ID NO: 17 in Table 1.

In some embodiments, a suitable Fc domain may contain mutations of L234A (Leu234Ala), L235A (Leu235Ala), H433K (His433Lys) and/or N434F (Asn434Phe) (EU numbering). As a non-limiting example, a suitable Fc domain may contain mutations L234A, L235A, H433K and N434F (EU numbering). In some embodiments, a suitable Fc domain may comprise mutations L234A/L235A, T350V, T366L, K392L, T394W. An exemplary Fc domain sequence incorporating the mutations L234A, L235A, H433K and N434F is shown as SEQ ID NO: 18 in Table 1.

In some embodiments, Chain A and Chain B of a suitable Fc domain may contain sets of complementary mutations. These sets include, e.g., (i) Chain A: T350V/L351Y/F405A/Y407V, Chain B: T350V/T366L/K392L/T394W; (ii); Chain A: T366W, S354C; Chain B: T366S, L368A, Y407V, Y349C; (iii) Chain A: K392D, K409D; Chain B: D399K, E356K; (iv) Chain A: K360E, K409W, Y349C; Chain B: Q347R, D399V, F405T, S354C; (v) Chain A: T366W; Chain B: T366S, L368A, Y407V; (vi) Chain A: K360E, K409W, Chain B: Q347R, D399V, F405T; and (vii) Chain A: T350V/L351Y/F405A/Y407V, Chain B: T350V/T366L/K392L/T394W.

Additional amino acid substitutions that can be included in the Fc domain include those described in, e.g., U.S. Pat. Nos. 6,277,375; 8,012,476; and 8,163,881, T.S. Von Kreutenstein, et al. Improving biophysical properties of a bispecific antibody scaffold to aid developability: quality by molecular design mAbs, 5 (2013), pp. 646-654; and Ha J-H, Kim J-E and Kim Y-S(2016) Immunoglobulin Fc Heterodimer Platform Technology: From Design to Applications in Therapeutic Antibodies and Proteins. Front. Immunol. 7:394; which are incorporated herein by reference.

Exemplary HO-1 Fusion Proteins

In some embodiments, the recombinant heme oxygenase protein is fused to Fc at the N-terminus. In some embodiments, the recombinant heme oxygenase protein is fused to the C-terminus.

In some embodiments, the recombinant heme oxygenase protein comprises a multimer comprising at least one monomer comprising an Fc domain fused to a recombinant heme oxygenase protein domain.

In some embodiments, the recombinant heme oxygenase protein comprises a multimer comprising at least one monomer comprising an Fc domain not fused to a recombinant heme oxygenase protein domain.

In some embodiments, the recombinant heme oxygenase protein is a dimer, trimer, tetramer, pentamer, or larger aggregate.

In some embodiments, a recombinant heme oxygenase dimeric protein comprises one monomer comprising an Fc domain (typically a human Fc domain) fused to a recombinant heme oxygenase protein domain and another monomer comprising an Fc domain (typically a human Fc domain) not fused to a recombinant heme oxygenase protein domain. The Fc domain can be fused either to the N-terminus or the C-terminus of the recombinant heme oxygenase protein domain, optionally via a linker. The optional linker can contain multiple (e.g., 1-4) repeats of the amono acid sequence GGGGS. The heme oxygenase protein domain can be an enzymatically active fragment of a heme oxygenase protein. For example, enzymatically active fragments suitable for use with the invention may comprise an amino acid sequence with residues 1-261 or 1-226 of SEQ ID NO:1. In particular embodiments, an Fc domain is fused to the C-terminus of the heme oxygenase protein domain, typically without a linker.

In some embodiments, the Fc domain comprises one or more mutations to enhance half-life, reduce aggregation and/or alter effector function.

In some embodiments, the IgG1 Fc region comprises amino acid substitutions at positions 234, 235, 251, 252, 254, 255, 256, 308, 309, 311, 312, 314, 385, 386, 387, 389, 428, 433, 434, 435 and/or 436 (according to EU numbering).

In some embodiments, the Fc region comprises L234A and L235A amino acid substitutions.

In some embodiments, the Fc domain fused to the recombinant heme oxygenase protein domain and the Fc domain not fused to a recombinant heme oxygenase protein domain contain complementary mutations that aid heterodimer formation. The complementary sets of mutations located in the two Fc domains (referred to as Chain A and Chain B, respectively) can include, e.g., (i) Chain A: T350V/L351Y/F405A/Y407V, Chain B: T350V/T366L/K392L/T394W; (ii); Chain A: T366W, S354C; Chain B: T366S, L368A, Y407V, Y349C; (iii) Chain A: K392D, K409D; Chain B: D399K, E356K; (iv) Chain A: K360E, K409W, Y349C; Chain B: Q347R, D399V, F405T, S354C; (v) Chain A: T366W; Chain B: T366S, L368A, Y407V; (vi) Chain A: K360E, K409W, Chain B: Q347R, D399V, F405T; and (vii) Chain A: T350V/L351Y/F405A/Y407V, Chain B: T350V/T366L/K392L/T394W. Recombinant heterodimeric proteins monovalent for a heme oxygenase domain (typically an enzymatically active fragment comprising an amino acid sequence with residues 1-261 or 1-226 of SEQ ID NO:1), which include Fc domains with complementray sets of mutations (e.g., sets (i), (iv) or (vii) as listed) above display robust enzymatic activity and can be purified at high yield.

In other embodiments, the monomer comprising the Fc domain fused to the recombinant heme oxygenase protein domain and the monomer comprising the Fc domain not fused to a recombinant heme oxygenase protein domain are linked (e.g., via a linker comprising multiple (e.g., 6-10) repeats of the amino acid sequence GGGGS), thus forming a single chain recombinant heme oxygenase protein. In particular embodiments, the two linked Fc domains are fused to the C-terminus of the heme oxygenase protein domain. Typically, no linker is required to fuse the two linked Fc domains to the heme oxygenase protein domain.

For greater stability, the two linked Fc domains (referred to as Chain A and Chain B, respectively) may include reverse charge mutations, e.g., Chain A: E357K; Chain B: K370D.

In another embodiment, a recombinant heme oxygenase dimeric protein comprises two monomers, each comprising an Fc domain fused to a recombinant heme oxygenase protein domain. In this embodiment, the two monomers may be identical, resulting in the formation of a heme oxygenase bivalent homodimer. The Fc domain can be fused either to the N-terminus or the C-terminus of the recombinant heme oxygenase protein domain, optionally via a linker. The optional linker can contain multiple (e.g., 1-4) repeats of the amono acid sequence GGGGS. The heme oxygenase protein domain can be an enzymatically active fragment of a heme oxygenase protein. For example, enzymatically active fragments suitable for use with the invention comprise an amino acid sequence with residues 1-261 or 1-226 of SEQ ID NO:1. In some embodiments, an Fc domain is fused to the C-terminus of the heme oxygenase protein domain (e.g., an enzymatically active fragments comprising the amino acid sequence with residues 1-226 of SEQ ID NO:1), typically without a linker the fragment. Fusing an Fc domain to the C-terminus of a heme oxygenase protein domain has been found to yield a recombinant heme oxygenase homodimeric protein with robust enzymatic activity that can be purified with a high yield.

In certain embodiments, an engineered protein as described herein can be PEGylated to include mono- or poly-(e.g., 2-4) PEG moieties. Such PEGylated proteins may display increased half-life in comparison to a non-PEGylated reference protein, e.g., a protein having the same amino acid sequence but different, a different amount of, or no PEGylation. Methods for preparing a PEGylated protein can generally include (a) reacting a polypeptide with polyethylene glycol (such as a reactive ester or aldehyde derivative of PEG) under conditions whereby the polypeptide becomes attached to one or more PEG groups; and (b) obtaining the reaction product(s). In general, the conditions for the reactions can be determined case by case based on known parameters and the desired result. A number of PEG attachment methods are available to those skilled in the art. For example, the step of PEGylating a multi-specific binding molecule described herein can be carried out via an acylation reaction or an alkylation reaction with a reactive polyethylene glycol molecule.

In some embodiments, serum half-life is increased by binding to a homo amino acid polymer (HAPylation), a proline-alanine-serine polymer (PAS, PASylation, or an elastin-like peptide (ELPylation), or fusion with artificial GLK.

In some embodiments, serum half-life of an engineered protein is increased. For example, binding of an engineered protein to FcRn increases serum half-life of the antibody to about 4 days to about 45 days, e.g., about 5 days to about 30 days, about 10 days to about 30 days, or about 20 days to about 30 days. In certain embodiments, an engineered antibody described herein has a serum half-life of about 5 days, about 10 days, about 15 days, about 20 days, about 25 days, about 30 days, about 35 days, about 40 days, about 45 days, about 50 days or longer.

In some embodiments, serum half-life is increased by binding to human serum albumin protein or transferrin protein or human IgG, via genetic fusion, or by non-covalent binding or chemical conjugation.

In some embodiments, serum half-life is increased by fusion with an anionic highly-sialylated peptide, such as the carboxy-terminal peptide (CTP, of chorionic gonadotropin β chain).

In some embodiments, serum half-life is increased by the use of a linker. In some embodiments, aggregation is reduced by the use of a linker.

In some embodiments, the recombinant heme oxygenase protein comprises a linker sequence of GGGGS (SEQ ID NO: 10).

In some embodiments, aggregation is reduced by use of a monomer or single-chain moiety.

In some embodiments, recombinant heme oxygenase is an Fc fusion comprising SEQ ID NO: 4 (1-261-Fc V1):

```
                                             (SEQ ID NO: 4)
MERPQPDSMPQDLSEALKEATKEVHTQAENAEFMRNFQKGQVTRDGFKLV

MASLYHIYVALEEEIERNKESPVFAPVYFPEELHRKAALEQDLAFWYGPR

WQEVIPYTPAMQRYVKRLHEVGRTEPELLVAHAYTRYLGDLSGGQVLKKI

AQKALDLPSSGEGLAFFTFPNIASATKFKQLYRSRMNSLEMTPAVRQRVI

EEAKTAFLLNIQLFEELQELLTHDTKDQSPSRAPGLRQRASNKVQDSAPV

ETPRGKPPLNTDKTHTCPPCPAPEAAGGPSVFLFPPKPKDTLMISRTPEV

TCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSK

LTVDKSRWQQGNVFSCSVMHEALHNHYTQKSLSLSPGK
```

In some embodiments, recombinant heme oxygenase is an Fc fusion comprising 1-161 Fc of SEQ ID NO: 4 and a signal peptide comprising MDMRVPAQLL GLLLLWFPGS RC (SEQ ID NO: 9).

In some embodiments, recombinant HO-1 comprises amino acid 1-261 of wild-type HO-1. In some embodiments, rHO-1 Fc fusions comprise an IgG1 Fc with LALA mutation. See Hezareh et al., J. Virol. 75, 12161-12168 (2001). In some embodiments, rHO-1-Fc fusion comprises a sequence that is at least 70%, 80%, 85%, 90%, 95%, 97%, 98%, 99% or 100% identical to SEQ ID NO: 4.

In some embodiments, recombinant heme oxygenase comprises an Fc fusion comprising SEQ ID NO: 5 (1-261-Fc V2). In some embodiments, rHO-1-Fc fusion comprises a sequence that is at least 70%, 80%, 85%, 90%, 95%, 97%, 98%, 99% or 100% identical to SEQ ID NO: 5.

```
                                             (SEQ ID NO: 5)
MERPQPDSMPQDLSEALKEATKEVHTQAENAEFMRNFQKGQVTRDGFKLV

MASLYHIYVALEEEIERNKESPVFAPVYFPEELHRKAALEQDLAFWYGPR
```

```
                   -continued
WQEVIPYTPAMQRYVKRLHEVGRTEPELLVAHAYTRYLGDLSGGQVLKKI

AQKALDLPSSGEGLAFFTFPNIASATKFKQLYRSRMNSLEMTPAVRQRVI

EEAKTAFLLNIQLFEELQELLTHDTKDQSPSRAPGLRQRASNKVQDSAPV

ETPRGKPPLNT GGGGS GGGGS GGGGS GGGGS DKTHTCPPCPA-
PEAAG

GPSVFLFPPPKPKDTLMISRTPEVTCVVVDVSHEDPEVKFNWYVDGVEVHN

AKTKPREEQYNSTYRVVSVLTVLHQDWLNGKEYKCKVSNKALPAPIEKTI

SKAKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHNHY

TQKSLSLSPGK
```

In some embodiments, rHO-1 comprises a signal peptide. In some embodiments, recombinant heme oxygenase is an Fc fusion comprising 1-161 Fc of SEQ ID NO: 5 and a signal peptide comprising MDMRVPAQLL GLLLLWFPGS RC (SEQ ID NO: 9).

In some embodiments, rHO-1 comprises a linker peptide. In some embodiments, the linker comprises GGGGS (SEQ ID NO: 10). In some embodiments, the linker comprises two or more repeats of GGGGS (SEQ ID NO: 62; "GGGGS" disclosed as SEQ ID NO: 10). In some embodiments, the linker comprises 4 repeats of GGGGS (SEQ ID NO: 21; "GGGGS" disclosed as SEQ ID NO: 10).

In some embodiments, recombinant heme oxygenase comprises an Fc fusion comprising SEQ ID NO: 6 (1-261-Fc V3). In some embodiments, rHO-1-Fc fusion comprises a sequence that is at least 70%, 80%, 85%, 90%, 95%, 97%, 98%, 99% or 100% identical to SEQ ID NO: 6.

```
                                             (SEQ ID NO: 6)
MDKTHTCPPCPAPEAAGGPSVFLFPPKPKDTLMISRTPEVTCVVVDVSHE

DPEVKFNWYVDGVEVHNAKTKPREEQYNSTYRVVSVLTVLHQDWLNGKEY

KCKVSNKALPAPIEKTISKAKGQPREPQVYTLPPSRDELTKNQVSLTCLV

KGFYPSDIAVEWESNGQPENNYKTTPPVLDSDGSFFLYSKLTVDKSRWQQ

GNVFSCSVMHEALHNHYTQKSLSL-
SPGK GGGGS GGGGS GGGGS GGGGS

ERPQPDSMPQDLSEALKEATKEVHTQAENAEFMRNFQKGQVTRDGFKLVM

ASLYHIYVALEEEIERNKESPVFAPVYFPEELHRKAALEQDLAFWYGPRW

QEVIPYTPAMQRYVKRLHEVGRTEPELLVAHAYTRYLGDLSGGQVLKKIA

QKALDLPSSGEGLAFFTFPNIASATKFKQLYRSRMNSLEMTPAVRQRVIE

EAKTAFLLNIQLFEELQELLTHDTKDQSPSRAPGLRQRASNKVQDSAPVE

TPRGKPPLNT
```

In some embodiments, rHO-1 comprises a signal peptide. In some embodiments, the signal peptide comprises MDMRVPAQLL GLLLLWFPGS RC (SEQ ID NO: 9). In some embodiments, recombinant heme oxygenase is an Fc fusion comprising 1-161 Fc of SEQ ID NO: 6 and a signal peptide comprising MDMRVPAQLL GLLLLWFPGS RC (SEQ ID NO: 9).

In some embodiments, recombinant heme oxygenase is an Fc fusion comprising SEQ ID NO: 7 (1-261-Fc V4 Chain A). In some embodiments, HO-1-Fc fusion comprises a sequence that is at least 70%, 80%, 85%, 90%, 95%, 97%, 98%, 99% or 100% identical to SEQ ID NO: 7.

(SEQ ID NO: 7)

```
MERPQPDSMPQDLSEALKEATKEVHTQAENAEFMRNFQKGQVTRDGFKLV

MASLYHIYVALEEEIERNKESPVFAPVYFPEELHRKAALEQDLAFWYGPR

WQEVIPYTPAMQRYVKRLHEVGRTEPELLVAHAYTRYLGDLSGGQVLKKI

AQKALDLPSSGEGLAFFTFPNIASATKFKQLYRSRMNSLEMTPAVRQRVI

EEAKTAFLLNIQLFEELQELLTHDTKDQSPSRAPGLRQRASNKVQDSAPV

ETPRGKPPLNTDKTHTCPPCPAPEAAGGPSVFLFPPKPKDTLMISRTPEV

TCVVVDVSHEDPEVKFNWYVDGVEVHNAKTKPREEQYNSTYRVVSVLTVL

HQDWLNGKEYKCKVSNKALPAPIEKTISKAKGQPREPQVYVYPPSRDELT

KNQVSLTCLVKGFYPSDIAVEWESNGQPENNYKTTPPVLDSDGSFALVSK

LTVDKSRWQQGNVFSCSVMHEALHNHYTQKSLSLSPGK
```

In some embodiments, rHO-1 comprises a signal peptide. In some embodiments, recombinant heme oxygenase is an Fc fusion comprising 1-161 Fc of SEQ ID NO: 7 and a signal peptide comprising MDMRVPAQLL GLLLLWFPGS RC (SEQ ID NO: 9).

In some embodiments, recombinant heme oxygenase is an Fc fusion comprising SEQ ID NO: 7 (1-261-Fc V4 Chain A). In some embodiments, the rHO-1 Fc fusion is expressed with a signal peptide (SEQ ID NO: 41). In some embodiments, the signal peptide is cleaved. In some embodiments, rHO-1-Fc fusion comprises a sequence that is at least 70%, 80%, 85%, 90%, 95%, 97%, 98%, 99% or 100% identical to SEQ ID NO: 41.

(SEQ ID NO: 41)

```
METPAQLLFLLLLWLPDTTGMERPQPDSMPQDLSEALKEATKEVHTQAEN

AEFMRNFQKGQVTRDGFKLVMASLYHIYVALEEEIERNKESPVFAPVYFP

EELHRKAALEQDLAFWYGPRWQEVIPYTPAMQRYVKRLHEVGRTEPELLV

AHAYTRYLGDLSGGQVLKKIAQKALDLPSSGEGLAFFTFPNIASATKFKQ

LYRSRMNSLEMTPAVRQRVIEEAKTAFLLNIQLFEELQELLTHDTKDQSP

SRAPGLRQRASNKVQDSAPVETPRGKPPLNTDKTHTCPPCPAPEAAGGPS

VFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKA

KGQPREPQVYVYPPSRDELTKNQVSLTCLVKGFYPSDIAVEWESNGQPEN

NYKTTPPVLDSDGSFALVSKLTVDKSRWQQGNVFSCSVMHEALHNHYTQK

SLSLSPGK
```

In some embodiments, recombinant heme oxygenase is an Fc fusion comprising SEQ ID NO: 8 (1-261-Fc V4 Chain B). In some embodiments, rHO-1-Fc fusion comprises a sequence that is at least 70%, 80%, 85%, 90%, 95%, 97%, 98%, 99% or 100% identical to SEQ ID NO: 8.

(SEQ ID NO: 8)

```
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYVLPPSRDELTKNQVSLLCLVK

GFYPSDIAVEWESNGQPENNYLTWPPVLDSDGSFFLYSKLTVDKSRWQQG

NVFSCSVMHEALHNHYTQKSLSLSPGK
```

In some embodiments, recombinant heme oxygenase is an Fc fusion comprising SEQ ID NO: 8 (1-261-Fc V4 Chain B). In some embodiments, the rHO-1 Fc fusion is expressed with a signal peptide (SEQ ID NO: 42). In some embodiments, the signal peptide is cleaved. In some embodiments, rHO-1-Fc fusion comprises a sequence that is at least 70%, 80%, 85%, 90%, 95%, 97%, 98%, 99% or 100% identical to SEQ ID NO: 42 including the signal peptide shown in bold below.

(SEQ ID NO: 42)

```
METPAQLLFLLLLWLPDTTGDKTHTCPPCPAPEAAGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYV

LPPSRDELTKNQVSLLCLVKGFYPSDIAVEWESNGQPENNYLTWPPVLDS

DGSFFLYSKLTVDKSRWQQGNVFSCSVMHEALHNHYTQKSLSLSPGK
```

In some embodiments, recombinant heme oxygenase is an Fc fusion comprising SEQ ID NO: 22 (1-261-Fc V5 Chain A, T366W and S354C; HO-1 underlined). In some embodiments, rHO-1-Fc fusion comprises a sequence that is at least 70%, 80%, 85%, 90%, 95%, 97%, 98%, 99% or 100% identical to SEQ ID NO: 22.

(SEQ ID NO: 22)

```
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGMERPQPDSMPQDLSEALKEATKEV

HTQAENAEFMRNFQKGQVTRDGFKLVMASLYHIYVALEEEIERNKESPVF

APVYFPEELHRKAALEQDLAFWYGPRWQEVIPYTPAMQRYVKRLHEVGRT

EPELLVAHAYTRYLGDLSGGQVLKKIAQKALDLPSSGEGLAFFTFPNIAS

ATKFKQLYRSRMNSLEMTPAVRQRVIEEAKTAFLLNIQLFEELQELLTHD

TKDQSPSRAPGLRQRASNKVQDSAPVETPRGKPPLNT
```

In some embodiments, recombinant heme oxygenase is an Fc fusion comprising SEQ ID NO: 22 (1-261-Fc V5 Chain A, T366W and S354C; HO-1 underlined). In some embodiments, the rHO-1 Fc fusion is expressed with a signal peptide (SEQ ID NO: 43). In some embodiments, the signal peptide is cleaved. In some embodiments, rHO-1-Fc fusion comprises a sequence that is at least 70%, 80%, 85%, 90%, 95%, 97%, 98%, 99% or 100% identical to SEQ ID NO: 43 including the signal peptide shown in bold below.

(SEQ ID NO: 43)

```
MGWSCHILFLVATATGVHSDKTHTCPPCPAPEAAGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPCRDELTKNQVSLWCLVKGFYPSDIAVEWESNGQPENNYKTTPPVLDSD

GSFFLYSKLTVDKSRWQQGNVFSCSVMHEALHNHYTQKSLSLSPGMERPQ

PDSMPQDLSEALKEATKEVHTQAENAEFMRNFQKGQVTRDGFKLVMASLY
```

-continued

HIYVALEEEIERNKESPVFAPVYFPEELHRKAALEQDLAFWYGPRWQEVI

PYTPAMQRYVKRLHEVGRTEPELLVAHAYTRYLGDLSGGQVLKKIAQKAL

DLPSSGEGLAFFTFPNIASATKFKQLYRSRMNSLEMTPAVRQRVIEEAKT

AFLLNIQLFEELQELLTHDTKDQSPSRAPGLRQRASNKVQDSAPVETPRG

KPPLNT

In some embodiments, recombinant heme oxygenase is an Fc fusion comprising SEQ ID NO: 23 (1-261-Fc V5 Chain B, T366S, L368A, Y407V and Y349C). In some embodiments, rHO-1-Fc fusion comprises a sequence that is at least 70%, 80%, 85%, 90%, 95%, 97%, 98%, 99% or 100% identical to SEQ ID NO: 23.

(SEQ ID NO: 23)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPG

In some embodiments, recombinant heme oxygenase is an Fc fusion comprising SEQ ID NO: 23 (1-261-Fc V5 Chain B, T366S, L368A, Y407V and Y349C). In some embodiments, the rHO-1 Fc fusion is expressed with a signal peptide (SEQ ID NO: 44). In some embodiments, the signal peptide is cleaved. In some embodiments, rHO-1-Fc fusion comprises a sequence that is at least 70%, 80%, 85%, 90%, 95%, 97%, 98%, 99% or 100% identical to SEQ ID NO: 44 including the signal peptide shown in bold below.

(SEQ ID NO: 44)
MGWSCHILFLVATATGVHSDKTHTCPPCPAPEAAGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVCTL

PPSRDELTKNQVSLSCAVKGFYPSDIAVEWESNGQPENNYKTTPPVLDSD

GSFFLVSKLTVDKSRWQQGNVFSCSVMHEALHNHYTQKSLSLSPG

In some embodiments, recombinant heme oxygenase is an Fc fusion comprising SEQ ID NO: 24 (1-261-Fc V6 Chain A, K392D, K409D, bold). In some embodiments, rHO-1-Fc fusion comprises a sequence that is at least 70%, 80%, 85%, 90%, 95%, 97%, 98%, 99% or 100% identical to SEQ ID NO: 24.

(SEQ ID NO: 24)
SDKTHTCPPCPAPEAAGGPSVFLFPPKPKDTLMISRTPEVTCVVVDVSHE

DPEVKFNWYVDGVEVHNAKTKPREEQYNSTYRVVSVLTVLHQDWLNGKEY

KCKVSNKALPAPIEKTISKAKGQPREPQVYTLPPSRDELTKNQVSLTCLV

KGFYPSDIAVEWESNGQPENNYDTTPPVLDSDGSFFLYSDLTVDKSRWQQ

GNVFSCSVMHEALHNHYTQKSLSLSPGMERPQPDSMPQDLSEALKEATKE

VHTQAENAEFMRNFQKGQVTRDGFKLVMASLYHIYVALEEEIERNKESPV

FAPVYFPEELHRKAALEQDLAFWYGPRWQEVIPYTPAMQRYVKRLHEVGR

TEPELLVAHAYTRYLGDLSGGQVLKKIAQKALDLPSSGEGLAFFTFPNIA

-continued

SATKFKQLYRSRMNSLEMTPAVRQRVIEEAKTAFLLNIQLFEELQELLTH

DTKDQSPSRAPGLRQRASNKVQDSAPVETPRGKPPLNT

In some embodiments, recombinant heme oxygenase is an Fc fusion comprising SEQ ID NO: 24 (1-261-Fc V6 Chain A, K392D, K409D). In some embodiments, the rHO-1 Fc fusion is expressed with a signal peptide (SEQ ID NO: 45). In some embodiments, the signal peptide is cleaved. In some embodiments, rHO-1-Fc fusion comprises a sequence that is at least 70%, 80%, 85%, 90%, 95%, 97%, 98%, 99% or 100% identical to SEQ ID NO: 45 including the signal peptide shown in bold below.

(SEQ ID NO: 45)
MGWSCHILFLVATATGVHSDKTHTCPPCPAPEAAGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDELTKNQVSLTCLVKGFYPSDIAVEWESNGQPENNYDTTPPVLDSD

GSFFLYSDLTVDKSRWQQGNVFSCSVMHEALHNHYTQKSLSLSPGMERPQ

PDSMPQDLSEALKEATKEVHTQAENAEFMRNFQKGQVTRDGFKLVMASLY

HIYVALEEEIERNKESPVFAPVYIPEEIHRKAALEQDLAFWYGPRWQEVI

PYTPAMQRYVKRLHEVGRTEPELLVAHAYTRYLGDLSGGQVLKKIAQKAL

DLPSSGEGLAFFTFPNIASATKFKQLYRSRMNSLEMTPAVRQRVIEEAKT

AFLLNIQLFEELQELLTHDTKDQSPSRAPGLRQRASNKVQDSAPVETPRG

KPPLNT

In some embodiments, recombinant heme oxygenase is an Fc fusion comprising SEQ ID NO: 25 (1-261-Fc V6 Chain B, D399K, E356K, bold). In some embodiments, rHO-1-Fc fusion comprises a sequence that is at least 70%, 80%, 85%, 90%, 95%, 97%, 98%, 99% or 100% identical to SEQ ID NO: 25.

(SEQ ID NO: 25)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRKELTKNQVSLTCLVK

GFYPSDIAVEWESNGQPENNYKTTPPVLKSDGSFFLYSKLTVDKSRWQQG

NVFSCSVMHEALHNHYTQKSLSLSPG

In some embodiments, recombinant heme oxygenase is an Fc fusion comprising SEQ ID NO: 25 (1-261-Fc V6 Chain B, D399K, E356K). In some embodiments, the rHO-1 Fc fusion is expressed with a signal peptide (SEQ ID NO: 46). In some embodiments, the signal peptide is cleaved. In some embodiments, rHO-1-Fc fusion comprises a sequence that is at least 70%, 80%, 85%, 90%, 95%, 97%, 98%, 99% or 100% identical to SEQ ID NO: 46 including the signal peptide shown in bold below.

(SEQ ID NO: 46)
MGWSCIILFLVATATGVHSDKTHTCPPCPAPEAAGGPSVFLFPPKPKDTL

MISRTPEVTCVVVDVSHEDPEVKFNWYVDGVEVHNAKTKPREEQYNSTYR

-continued
```
VVSVLTVLHQDWLNGKEYKCKVSNKALPAPIEKTISKAKGQPREPQVYTL

PPSRKELTKNQVSLTCLVKGFYPSDIAVEWESNGQPENNYKTTPPVLKSD

GSFFLYSKLTVDKSRWQQGNVFSCSVMHEALHNHYTQKSLSLSPG
```

In some embodiments, recombinant heme oxygenase is an Fc fusion comprising SEQ ID NO: 26 (1-261-Fc V7 Chain A, K360E, K409W, Y349C, bold). In some embodiments, rHO-1-Fc fusion comprises a sequence that is at least 70%, 80%, 85%, 90%, 95%, 97%, 98%, 99% or 100% identical to SEQ ID NO: 26.

```
                                              (SEQ ID NO: 26)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTENQVSLTCLVK

GFYPSDIAVEWESNGQPENNYKTTPPVLDSDGSFFLYSWLTVDKSRWQQG

NVFSCSVMHEALHNHYTQKSLSLSPGMERPQPDSMPQDLSEALKEATKEV

HTQAENAEFMRNFQKGQVTRDGFKLVMASLYHIYVALEEEIERNKESPVF

APVYFPEELHRKAALEQDLAFWYGPRWQEVIPYTPAMQRYVKRLHEVGRT

EPELLVAHAYTRYLGDLSGGQVLKKIAQKALDLPSSGEGLAFFTFPNIAS

ATKFKQLYRSRMNSLEMTPAVRQRVIEEEAKTAFLLNIQLFEELQELLTHD

TKDQSPSRAPGLRQRASNKVQDSAPVETPRGKPPLNT
```

In some embodiments, recombinant heme oxygenase is an Fc fusion comprising SEQ ID NO: 26 (1-261-Fc V7 Chain A, K360E, K409W, Y349C). In some embodiments, the rHO-1 Fc fusion is expressed with a signal peptide (SEQ ID NO: 47). In some embodiments, the signal peptide is cleaved. In some embodiments, rHO-1-Fc fusion comprises a sequence that is at least 70%, 80%, 85%, 90%, 95%, 97%, 98%, 99% or 100% identical to SEQ ID NO: 47 including the signal peptide shown in bold below.

```
                                              (SEQ ID NO: 47)
MGWSCIILFLVATATGVHSDKTHTCPPCPAPEAAGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVCTL

PPSRDELTENQVSLTCLVKGFYPSDIAVEWESNGQPENNYKTTPPVLDSD

GSFFLYSWLTVDKSRWQQGNVFSCSVMHEALHNHYTQKSLSLSPGMERPQ

PDSMPQDLSEALKEATKEVHTQAENAEFMRNFQKGQVTRDGFKLVMASLY

HIYVALEEEIERNKESPVFAPVYFPEELHRKAALEQDLAFWYGPRWQEVI

PYTPAMQRYVKRLHEVGRTEPELLVAHAYTRYLGDLSGGQVLKKIAQKAL

DLPSSGEGLAFFTFPNIASATKFKQLYRSRMNSLEMTPAVRQRVIEEAKT

AFLLNIQLFEELQELLTHDTKDQSPSRAPGLRQRASNKVQDSAPVETPRG

KPPLNT
```

In some embodiments, recombinant heme oxygenase is an Fc fusion comprising SEQ ID NO: 27 (1-261-Fc V7 Chain B, Q347R, D399V, F405T, S354C, bold). In some embodiments, rHO-1-Fc fusion comprises a sequence that is at least 70%, 80%, 85%, 90%, 95%, 97%, 98%, 99% or 100% identical to SEQ ID NO: 27.

```
                                              (SEQ ID NO: 27)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPRVYTLPPCRDELTKNQVSLTCLVK

GFYPSDIAVEWESNGQPENNYKTTPPVLVSDGSFTLYSKLTVDKSRWQQG

NVFSCSVMHEALHNHYTQKSLSLSPG
```

In some embodiments, recombinant heme oxygenase is an Fc fusion comprising SEQ ID NO: 27 (1-261-Fc V7 Chain B, Q347R, D399V, F405T, S354C). In some embodiments, the rHO-1 Fc fusion is expressed with a signal peptide (SEQ ID NO: 48). In some embodiments, the signal peptide is cleaved. In some embodiments, rHO-1-Fc fusion comprises a sequence that is at least 70%, 80%, 85%, 90%, 95%, 97%, 98%, 99% or 100% identical to SEQ ID NO: 48 including the signal peptide shown in bold below.

```
                                              (SEQ ID NO: 48)
MGWSCIILFLVATATGVHSDKTHTCPPCPAPEAAGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPRVYTL

PPCRDELTKNQVSLTCLVKGFYPSDIAVEWESNGQPENNYKTTPPVLVSD

GSFTLYSKLTVDKSRWQQGNVFSCSVMHEALHNHYTQKSLSLSPG
```

In some embodiments, recombinant heme oxygenase is an Fc fusion comprising SEQ ID NO: 28 (1-261-Fc V8 Chain A, T366W, bold; HO-1 underlined). In some embodiments, rHO-1-Fc fusion comprises a sequence that is at least 70%, 80%, 85%, 90%, 95%, 97%, 98%, 99% or 100% identical to SEQ ID NO: 28.

```
                                              (SEQ ID NO: 28)
MERPQPDSMPQDLSEALKEATKEVHTQAENAEFMRNFQKGQVTRDGFKLV

MASLYHIYVALEEEIERNKESPVFAPVYFPEELHRKAALEQDLAFWYGPR

WQEVIPYTPAMQRYVKRLHEVGRTEPELLVAHAYTRYLGDLSGGQVLKKI

AQKALDLPSSGEGLAFFTFPNIASATKFKQLYRSRMNSLEMTPAVRQRVI

EEAKTAFLLNIQLFEELQELLTHDTKDQSPSRAPGLRQRASNKVQDSAPV

ETPRGKPPLNTDKTHTCPPCPAPEAAGGPSVFLFPPKPKDTLMISRTPEV

TCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELT

KNQVSLWCLVKGFYPSDIAVEWESNGQPENNYKTTPPVLDSDGSFFLYSK

LTVDKSRWQQGNVFSCSVMHEALHNHYTQKSLSLSPG
```

In some embodiments, recombinant heme oxygenase is an Fc fusion comprising SEQ ID NO: 28 (1-261-Fc V8 Chain A, T366W). In some embodiments, the rHO-1 Fc fusion is expressed with a signal peptide (SEQ ID NO: 49). In some embodiments, the signal peptide is cleaved. In some embodiments, rHO-1-Fc fusion comprises a sequence that is at least 70%, 80%, 85%, 90%, 95%, 97%, 98%, 99% or 100% identical to SEQ ID NO: 49 including the signal peptide shown in bold below.

(SEQ ID NO: 49)
MGWSCHILFLVATATGVHSMERPQPDSMPQDLSEALKEATKEVHTQAENA

EFMRNFQKGQVTRDGFKLVMASLYHIYVALEEEIERNKESPVFAPVYFPE

ELHRKAALEQDLAFWYGPRWQEVIPYTPAMQRYVKRLHEVGRTEPELLVA

HAYTRYLGDLSGGQVLKKIAQKALDLPSSGEGLAFFTFPNIASATKFKQL

YRSRMNSLEMTPAVRQRVIEEAKTAFLLNIQLFEELQELLTHDTKDQSPS

RAPGLRQRASNKVQDSAPVETPRGKPPLNTDKTHTCPPCPAPEAAGGPSV

FLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK

GQPREPQVYTLPPSRDELTKNQVSLWCLVKGFYPSDIAVEWESNGQPENN

YKTTPPVLDSDGSFFLYSKLTVDKSRWQQGNVFSCSVMHEALHNHYTQKS

LSLSPG

In some embodiments, recombinant heme oxygenase is an Fc fusion comprising SEQ ID NO: 29 (1-261-Fc V8 Chain B, T366S, L368A, Y407V, bold). In some embodiments, rHO-1-Fc fusion comprises a sequence that is at least 70%, 80%, 85%, 90%, 95%, 97%, 98%, 99% or 100% identical to SEQ ID NO: 29.

(SEQ ID NO: 29)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPG

In some embodiments, recombinant heme oxygenase is an Fc fusion comprising SEQ ID NO: 29 (1-261-Fc V8 Chain B, T366S, L368A, Y407V). In some embodiments, the rHO-1 Fc fusion is expressed with a signal peptide (SEQ ID NO: 50). In some embodiments, the signal peptide is cleaved. In some embodiments, rHO-1-Fc fusion comprises a sequence that is at least 70%, 80%, 85%, 90%, 95%, 97%, 98%, 99% or 100% identical to SEQ ID NO: 50 including the signal peptide shown in bold below.

(SEQ ID NO: 50)
MGWSCIILFLVATATGVHSDKTHTCPPCPAPEAAGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDELTKNQVSLSCAVKGFYPSDIAVEWESNGQPENNYKTTPPVLDSD

GSFFLVSKLTVDKSRWQQGNVFSCSVMHEALHNHYTQKSLSLSPG

In some embodiments, recombinant heme oxygenase is an Fc fusion comprising SEQ ID NO: 30 (1-261-Fc V9 Chain A, K360E, K409W, bold). In some embodiments, rHO-1-Fc fusion comprises a sequence that is at least 70%, 80%, 85%, 90%, 95%, 97%, 98%, 99% or 100% identical to SEQ ID NO: 30.

(SEQ ID NO: 30)
MERPQPDSMPQDLSEALKEATKEVHTQAENAEFMRNFQKGQVTRDGFKLV

MASLYHIYVALEEEIERNKESPVFAPVYFPEELHRKAALEQDLAFWYGPR

-continued

WQEVIPYTPAMQRYVKRLHEVGRTEPELLVAHAYTRYLGDLSGGQVLKKI

AQKALDLPSSGEGLAFFTFPNIASATKFKQLYRSRMNSLEMTPAVRQRVI

EEAKTAFLLNIQLFEELQELLTHDTKDQSPSRAPGLRQRASNKVQDSAPV

ETPRGKPPLNTDKTHTCPPCPAPEAAGGPSVFLFPPKPKDTLMISRTPEV

TCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELT

ENQVSLTCLVKGFYPSDIAVEWESNGQPENNYKTTPPVLDSDGSFFLYSW

LTVDKSRWQQGNVFSCSVMHEALHNHYTQKSLSLSPG

In some embodiments, recombinant heme oxygenase is an Fc fusion comprising SEQ ID NO: 30 (1-261-Fc V9 Chain A, K360E, K409W). In some embodiments, the rHO-1 Fc fusion is expressed with a signal peptide (SEQ ID NO: 51). In some embodiments, the signal peptide is cleaved. In some embodiments, rHO-1-Fc fusion comprises a sequence that is at least 70%, 80%, 85%, 90%, 95%, 97%, 98%, 99% or 100% identical to SEQ ID NO: 51 including the signal peptide shown in bold below.

(SEQ ID NO: 51)
MGWSCIILFLVATATGVHSMERPQPDSMPQDLSEALKEATKEVHTQAENA

EFMRNFQKGQVTRDGFKLVMASLYHIYVALEEEIERNKESPVFAPVYFPE

ELHRKAALEQDLAFWYGPRWQEVIPYTPAMQRYVKRLHEVGRTEPELLVA

HAYTRYLGDLSGGQVLKKIAQKALDLPSSGEGLAFFTFPNIASATKFKQL

YRSRMNSLEMTPAVRQRVIEEAKTAFLLNIQLFEELQELLTHDTKDQSPS

RAPGLRQRASNKVQDSAPVETPRGKPPLNTDKTHTCPPCPAPEAAGGPSV

FLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK

GQPREPQVYTLPPSRDELTENQVSLTCLVKGFYPSDIAVEWESNGQPENN

YKTTPPVLDSDGSFFLYSWLTVDKSRWQQGNVFSCSVMHEALHNHYTQKS

LSLSPG

In some embodiments, recombinant heme oxygenase is an Fc fusion comprising SEQ ID NO: 31 (1-261-Fc V9 Chain B, Q347R, D399V, F405T, bold). In some embodiments, rHO-1-Fc fusion comprises a sequence that is at least 70%, 80%, 85%, 90%, 95%, 97%, 98%, 99% or 100% identical to SEQ ID NO: 31.

(SEQ ID NO: 31)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPRVYTLPPSRDELTKNQVSLTCLVK

GFYPSDIAVEWESNGQPENNYKTTPPVLVSDGSFTLYSKLTVDKSRWQQG

NVFSCSVMHEALHNHYTQKSLSLSPG

In some embodiments, recombinant heme oxygenase is an Fc fusion comprising SEQ ID NO: 31 (1-261-Fc V9 Chain B, Q347R, D399V, F405T). In some embodiments, the rHO-1 Fc fusion is expressed with a signal peptide (SEQ ID NO: 52). In some embodiments, the signal peptide is cleaved. In some embodiments, rHO-1-Fc fusion comprises a sequence that is at least 70%, 80%, 85%, 90%, 95%, 97%, 98%, 99% or 100% identical to SEQ ID NO: 52 including the signal peptide shown in bold below.

```
                                    (SEQ ID NO: 52)
MGWSCHILFLVATATGVHSDKTHTCPPCPAPEAAGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPRVYTL

PPSRDELTKNQVSLTCLVKGFYPSDIAVEWESNGQPENNYKTTPPVLVSD

GSFTLYSKLTVDKSRWQQGNVFSCSVMHEALHNHYTQKSLSLSPG
```

In some embodiments, recombinant heme oxygenase is an Fc fusion comprising SEQ ID NO: 32 (1-226-Fc V10 Chain A, T350V, L351Y, F405A, Y407V, bold; HO-1 underlined). In some embodiments, rHO-1-Fc fusion comprises a sequence that is at least 70%, 80%, 85%, 90%, 95%, 97%, 98%, 99% or 100% identical to SEQ ID NO: 31.

```
                                    (SEQ ID NO: 32)
MERPQPDSMPQDLSEALKEATKEVHTQAENAEFMRNFQKGQVTRDGFKLV

MASLYHIYVALEEEIERNKESPVFAPVYFPEELHRKAALEQDLAFWYGPR

WQEVIPYTPAMQRYVKRLHEVGRTEPELLVAHAYTRYLGDLSGGQVLKKI

AQKALDLPSSGEGLAFFTFPNIASATKFKQLYRSRMNSLEMTPAVRQRVI

EEAKTAFLLNIQLFEELQELLTHDTKDKTHTCPPCPAPEAAGGPSVFLFP

PKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPR

EPQVYVYPPSRDELTKNQVSLTCLVKGFYPSDIAVEWESNGQPENNYKTT

PPVLDSDGSFALVSKLTVDKSRWQQGNVFSCSVMHEALHNHYTQKSLSLS

PG
```

In some embodiments, recombinant heme oxygenase is an Fc fusion comprising SEQ ID NO: 32 (1-226-Fc V10 Chain A, T350V, L351Y, F405A, Y407V). In some embodiments, the rHO-1 Fc fusion is expressed with a signal peptide (SEQ ID NO: 53). In some embodiments, the signal peptide is cleaved. In some embodiments, rHO-1-Fc fusion comprises a sequence that is at least 70%, 80%, 85%, 90%, 95%, 97%, 98%, 99% or 100% identical to SEQ ID NO: 53 including the signal peptide shown in bold below.

```
                                    (SEQ ID NO: 53)
METPAQLLFLLLLWLPDTTGMERPQPDSMPQDLSEALKEATKEVHTQAEN

AEFMRNFQKGQVTRDGFKLVMASLYHIYVALEEEIERNKESPVFAPVYFP

EELHRKAALEQDLAFWYGPRWQEVIPYTPAMQRYVKRLHEVGRTEPELLV

AHAYTRYLGDLSGGQVLKKIAQKALDLPSSGEGLAFFTFPNIASATKFKQ

LYRSRMNSLEMTPAVRQRVIEEAKTAFLLNIQLFEELQELLTHDTKDKTH

TCPPCPAPEAAGGPSVFLFPPKPKDTLMISRTPEVTCVVVDVSHEDPEVK

FNWYVDGVEVHNAKTKPREEQYNSTYRVVSVLTVLHQDWLNGKEYKCKVS

NKALPAPIEKTISKAKGQPREPQVYVYPPSRDELTKNQVSLTCLVKGFYP

SDIAVEWESNGQPENNYKTTPPVLDSDGSFALVSKLTVDKSRWQQGNVFS

CSVMHEALHNHYTQKSLSLSPG
```

In some embodiments, recombinant heme oxygenase is an Fc fusion comprising SEQ ID NO: 33 (1-226-Fc V10 Chain B, T350V, T366L, K392L, T394W, bold). In some embodiments, rHO-1-Fc fusion comprises a sequence that is at least 70%, 80%, 85%, 90%, 95%, 97%, 98%, 99% or 100% identical to SEQ ID NO: 33.

```
                                    (SEQ ID NO: 33)
DKTHTCPPCPAPEAAGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYVLPPSRDELTKNQVSLLC

LVKGFYPSDIAVEWESNGQPENNYLTWPPVLDSDGSFFLYSKLTVDKSR

WQQGNVFSCSVMHEALHNHYTQKSLSLSPG
```

In some embodiments, recombinant heme oxygenase is an Fc fusion comprising SEQ ID NO: 33 (1-226-Fc V10 Chain B, T350V, T366L, K392L, T394W). In some embodiments, the rHO-1 Fc fusion is expressed with a signal peptide (SEQ ID NO: 54). In some embodiments, the signal peptide is cleaved. In some embodiments, rHO-1-Fc fusion comprises a sequence that is at least 70%, 80%, 85%, 90%, 95%, 97%, 98%, 99% or 100% identical to SEQ ID NO: 54 including the signal peptide shown in bold below.

```
                                    (SEQ ID NO: 54)
METPAQLLFLLLLWLPDTTGDKTHTCPPCPAPEAAGGPSVFLFPPKPKD

TLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQ

VYVLPPSRDELTKNQVSLLCLVKGFYPSDIAVEWESNGQPENNYLTWPP

VLDSDGSFFLYSKLTVDKSRWQQGNVFSCSVMHEALHNHYTQKSLSLSP

G
```

In some embodiments, recombinant heme oxygenase is an Fc fusion comprising SEQ ID NO: 34 (1-226-Fc V11; HO-1 underlined). In some embodiments, rHO-1-Fc fusion comprises a sequence that is at least 70%, 80%, 85%, 90%, 95%, 97%, 98%, 99% or 100% identical to SEQ ID NO: 34.

```
                                    (SEQ ID NO: 34)
DKTHTCPPCPAPEAAGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSR

WQQGNVFSCSVMHEALHNHYTQKSLSLSPGMERPQPDSMPADLSEALKE

ATKEVHTAAENAEFMRNFQKGAVTRDGFKLVMASLYHIYVALEEEIERN

KESPVFAPVYFPEELHRKAALEADLAFWYGPRWAEVIPYTPAMARYVKR

LHEVGRTEPELLVAHAYTRYLGDLSGGAVLKKIAAKALDLPSSGEGLAF

FTFPNIASATKFKALYRSRMNSLEMTPAVRARVIEEAKTAFLLNIALFE

ELAELLTHDTK
```

In some embodiments, recombinant heme oxygenase is an Fc fusion comprising SEQ ID NO: 34 (1-226-Fc V11). In some embodiments, the rHO-1 Fc fusion is expressed with a signal peptide (SEQ ID NO: 55). In some embodiments, the signal peptide is cleaved. In some embodiments, rHO-1-Fc fusion comprises a sequence that is at least 70%, 80%, 85%, 90%, 95%, 97%, 98%, 99% or 100% identical to SEQ ID NO: 55 including the signal peptide shown in bold below.

(SEQ ID NO: 55)

MGWSCHILFLVATATGVHSDKTHTCPPCPAPEAAGGPSVFLFPPKPKDT

LMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

MERPQPDSMPQDLSEALKEATKEVHTQAENAEFMRNFQKGQVTRDGFKL

VMASLYHIYVALEEEIERNKESPVFAPVYFPEELHRKAALEQDLAFWYG

PRWQEVIPYTPAMQRYVKRLHEVGRTEPELLVAHAYTRYLGDLSGGQVL

KKIAQKALDLPSSGEGLAFFTFPNIASATKFKQLYRSRMNSLEMTPAVR

QRVIEEAKTAFLLNIQLFEELQELLTHDTK

In some embodiments, recombinant heme oxygenase is an Fc fusion comprising SEQ ID NO: 35 (1-226-Fc V12; HO-1 underlined). In some embodiments, rHO-1-Fc fusion comprises a sequence that is at least 70%, 80%, 85%, 90%, 95%, 97%, 98%, 99% or 100% identical to SEQ ID NO: 35.

(SEQ ID NO: 35)

MGWSCHILFLVATATGVHSMERPQPDSMPQDLSEALKEATKEVHTQAEN

AEFMRNFQKGQVTRDGFKLVMASLYHIYVALEEEIERNKESPVFAPVYF

PEELHRKAALEQDLAFWYGPRWQEVIPYTPAMQRYVKRLHEVGRTEPEL

LVAHAYTRYLGDLSGGQVLKKIAQKALDLPSSGEGLAFFTFPNIASATK

FKQLYRSRMNSLEMTPAVRQRVIEEAKTAFLLNIQLFEELQELLTHDTK

DKTHTCPPCPAPEAAGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSR

WQQGNVFSCSVMHEALHNHYTQKSLSLSPG

In some embodiments, recombinant heme oxygenase is an Fc fusion comprising SEQ ID NO: 35 (1-226-Fc V12). In some embodiments, the rHO-1 Fc fusion is expressed with a signal peptide (SEQ ID NO: 56). In some embodiments, the signal peptide is cleaved. In some embodiments, rHO-1-Fc fusion comprises a sequence that is at least 70%, 80%, 85%, 90%, 95%, 97%, 98%, 99% or 100% identical to SEQ ID NO: 56 including the signal peptide shown in bold below.

(SEQ ID NO: 56)

MGWSCIILFLVATATGVHSMERPQPDSMPQDLSEALKEATKEVHTQAEN

AEFMRNFQKGQVTRDGFKLVMASLYHIYVALEEEIERNKESPVFAPVYF

PEELHRKAALEQDLAFWYGPRWQEVIPYTPAMQRYVKRLHEVGRTEPEL

LVAHAYTRYLGDLSGGQVLKKIAQKALDLPSSGEGLAFFTFPNIASATK

FKQLYRSRMNSLEMTPAVRQRVIEEAKTAFLLNIQLFEELQELLTHDTK

DKTHTCPPCPAPEAAGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC

-continued

LVKGFYPSDIAVEWESNGQPENNYKTTPPVLDSDGSFFLYSKLTVDKSR

WQQGNVFSCSVMHEALHNHYTQKSLSLSPG

In some embodiments, recombinant heme oxygenase is an Fc fusion comprising SEQ ID NO: 36 (1-261-Fc V13; HO-1 underlined). In some embodiments, rHO-1-Fc fusion comprises a sequence that is at least 70%, 80%, 85%, 90%, 95%, 97%, 98%, 99% or 100% identical to SEQ ID NO: 36.

(SEQ ID NO: 36)

MERPQPDSMPQDLSEALKEATKEVHTQAENAEFMRNFQKGQVTRDGFKL

VMASLYHIYVALEEEIERNKESPVFAPVYFPEELHRKAALEQDLAFWYG

PRWQEVIPYTPAMQRYVKRLHEVGRTEPELLVAHAYTRYLGDLSGGQVL

KKIAQKALDLPSSGEGLAFFTFPNIASATKFKQLYRSRMNSLEMTPAVR

QRVIEEAKTAFLLNIQLFEELQELLTHDTKDQSPSRAPGLRQRASNKVQ

DSAPVETPRGKPPLNTDKTHTCPPCPAPEAAGGPSVFLFPPKPKDTLMI

SRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGGGG

GSGGGGSGGGGSGGGGSGGGGSGGGGSGGGGSGGGGSGEPKSSDKTHTC

PPCPAPEAAGGPSVFLFPPKPKDTLMISRTPEVTCVVVDVSHEDPEVKF

NWYVDGVEVHNAKTKPREEQYNSTYRVVSVLTVLHQDWLNGKEYKCKVS

NKALPAPIEKTISKAKGQPREPQVYTLPPSRDELTKNQVSLTCLVKGFY

PSDIAVEWESNGQPENNYKTTPPVLDSDGSFFLYSKLTVDKSRWQQGNV

FSCSVMHEALHNHYTQKSLSLSPG

In some embodiments, recombinant heme oxygenase is an Fc fusion comprising SEQ ID NO: 36 (1-261-Fc V13). In some embodiments, the rHO-1 Fc fusion is expressed with a signal peptide (SEQ ID NO: 57). In some embodiments, the signal peptide is cleaved. In some embodiments, rHO-1-Fc fusion comprises a sequence that is at least 70%, 80%, 85%, 90%, 95%, 97%, 98%, 99% or 100% identical to SEQ ID NO: 57 including the signal peptide shown in bold below.

(SEQ ID NO: 57)

MGWSCIILFLVATATGVHSMERPQPDSMPQDLSEALKEATKEVHTQAEN

AEFMRNFQKGQVTRDGFKLVMASLYHIYVALEEEIERNKESPVFAPVYF

PEELHRKAALEQDLAFWYGPRWQEVIPYTPAMQRYVKRLHEVGRTEPEL

LVAHAYTRYLGDLSGGQVLKKIAQKALDLPSSGEGLAFFTFPNIASATK

FKQLYRSRMNSLEMTPAVRQRVIEEAKTAFLLNIQLFEELQELLTHDTK

DQSPSRAPGLRQRASNKVQDSAPVETPRGKPPLNTDKTHTCPPCPAPEA

AGGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHE

ALHNHYTQKSLSLSPGGGGGSGGGGSGGGGSGGGGSGGGGSGGGGSGGG

-continued

```
GSGGGGGSGEPKSSDKTHTCPPCPAPEAAGGPSVFLFPPKPKDTLMISRT

PEVTCVVVDVSHEDPEVKFNWYVDGVEVHNAKTKPREEQYNSTYRVVSV

LTVIHQDW1NGKEYKCKVSNKALPAPIEKTISKAKGQPREPQVYTLPPS

RDELTKNQVSLTCLVKGFYPSDIAVEWESNGQPENNYKTTPPVLDSDGS

FFLYSKLTVDKSRWQQGNVFSCSVMHEALHNHYTQKSLSLSPG
```

In some embodiments, recombinant heme oxygenase is an Fc fusion comprising SEQ ID NO: 37 (1-261-Fc V14; HO-1 underlined). In some embodiments, rHO-1-Fc fusion comprises a sequence that is at least 70%, 80%, 85%, 90%, 95%, 97%, 98%, 99% or 100% identical to SEQ ID NO: 37.

```
                                         (SEQ ID NO: 37)
MERPQPDSMPQDLSEALKEATKEVHTQAENAEFMRNFQKGQVTRDGFKL

VMASLYHIYVALEEEIERNKESPVFAPVYFPEELHRKAALEQDLAFWYG

PRWQEVIPYTPAMQRYVKRLHEVGRTEPELLVAHAYTRYLGDLSGGQVL

KKIAQKALDLPSSGEGLAFFTFPNIASATKFKQLYRSRMNSLEMTPAVR

QRVIEEAKTAFLLNIQLFEELQELLTHDTKDQSPSRAPGLRQRASNKVQ

DSAPVETPRGKPPLNTPAPEAAGGPSVFLFPPKPKDTLMISRTPEVTCV

VVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRDKLTK

NQVSLTCLVKGFYPSDIAVEWESNGQPENNYKTTPPVLDSDGSFFLYSK

LTVDKSRWQQGNVFSCSVMHEALHNHYTQKSLSLSPGGGGGGSGGGGSGG

GGSGGGGSGGGGSGGGGSGGGGSGGGGSGGGGSGGGGSGGGGSGGGGSG

GGGSPAPEAAGGPSVFLFPPKPKDTLMISRTPEVTCVVVDVSHEDPEVK

FNWYVDGVEVHNAKTKPREEQYNSTYRVVSVLTVLHQDWLNGKEYKCKV

SNKALPAPIEKTISKAKGQPREPQVYTLPPSRDELTKNQVSLTCLVDGF

YPSDIAVEWESNGQPENNYKTTPPVLDSDGSFFLYSKLTVDKSRWQQGN

VFSCSVMHEALHNHYTQKSLSLSPG
```

In some embodiments, recombinant heme oxygenase is an Fc fusion comprising SEQ ID NO: 37 (1-261-Fc V14). In some embodiments, the rHO-1 Fc fusion is expressed with a signal peptide (SEQ ID NO: 58). In some embodiments, the signal peptide is cleaved. In some embodiments, rHO-1-Fc fusion comprises a sequence that is at least 70%, 80%, 85%, 90%, 95%, 97%, 98%, 99% or 100% identical to SEQ ID NO: 58 including the signal peptide shown in bold below.

```
                                         (SEQ ID NO: 58)
MGWSCIILFLVATATGVHSMERPQPDSMPQDLSEALKEATKEVHTQAEN

AEFMRNFQKGQVTRDGFKLVMASLYHIYVALEEEIERNKESPVFAPVYF

PEELHRKAALEQDLAFWYGPRWQEVIPYTPAMQRYVKRLHEVGRTEPEL

LVAHAYTRYLGDLSGGQVLKKIAQKALDLPSSGEGLAFFTFPNIASATK

FKQLYRSRMNSLEMTPAVRQRVIEEAKTAFLLNIQLFEELQELLTHDTK

DQSPSRAPGLRQRASNKVQDSAPVETPRGKPPLNTPAPEAAGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG
```

-continued

```
QPREPQVYTLPPSRDKLTKNQVSLTCLVKGFYPSDIAVEWESNGQPENN

YKTTPPVLDSDGSFFLYSKLTVDKSRWQQGNVFSCSVMHEALHNHYTQK

SLSLSPGGGGGSGGGGSGGGGSGGGGSGGGGSGGGGSGGGGSGGGGSGG

GGSGGGGSGGGGSGGGGSGGGGSPAPEAAGGPSVFLFPPKPKDTLMISR

TPEVTCVVVDVSHEDPEVKFNWYVDGVEVHNAKTKPREEQYNSTYRVVS

VLTVLHQDWLNGKEYKCKVSNKALPAPIEKTISKAKGQPREPQVYTLPP

SRDELTKNQVSLTCLVDGFYPSDIAVEWESNGQPENNYKTTPPVLDSDG

SFFLYSKLTVDKSRWQQGNVFSCSVMHEALHNHYTQKSLSLSPG
```

In some embodiments, recombinant heme oxygenase is an Fc fusion comprising SEQ ID NO: 38 (1-226-Fc V15; HO-1 underlined). In some embodiments, rHO-1-Fc fusion comprises a sequence that is at least 70%, 80%, 85%, 90%, 95%, 97%, 98%, 99% or 100% identical to SEQ ID NO: 38.

```
                                         (SEQ ID NO: 38)
MERPQPDSMPQDLSEALKEATKEVHTQAENAEFMRNFQKGQVTRDGFKL

VMASLYHIYVALEEEIERNKESPVFAPVYFPEELHRKAALEQDLAFWYG

PRWQEVIPYTPAMQRYVKRLHEVGRTEPELLVAHAYTRYLGDLSGGQVL

KKIAQKALDLPSSGEGLAFFTFPNIASATKFKQLYRSRMNSLEMTPAVR

QRVIEEAKTAFLLNIQLFEELQELLTHDTKDKTHTCPPCPAPEAAGGPS

VFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHNH

YTQKSLSLSPGGGGGSGGGGSGGGGSGGGGSGGGGSGGGGSGGGGSGGG

GSGEPKSSDKTHTCPPCPAPEAAGGPSVFLFPPKPKDTLMISRTPEVTC

VVVDVSHEDPEVKFNWYVDGVEVHNAKTKPREEQYNSTYRVVSVITVLH

QDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYS

KLTVDKSRWQQGNVFSCSVMHEALHNHYTQKSLSLSPG
```

In some embodiments, recombinant heme oxygenase is an Fc fusion comprising SEQ ID NO: 38 (1-226-Fc V15). In some embodiments, the rHO-1 Fc fusion is expressed with a signal peptide (SEQ ID NO: 59). In some embodiments, the signal peptide is cleaved. In some embodiments, rHO-1-Fc fusion comprises a sequence that is at least 70%, 80%, 85%, 90%, 95%, 97%, 98%, 99% or 100% identical to SEQ ID NO: 59 including the signal peptide shown in bold below.

```
                                         (SEQ ID NO: 59)
MGWSCHILFLVATATGVHSMERPQPDSMPQDLSEALKEATKEVHTQAEN

AEFMRNFQKGQVTRDGFKLVMASLYHIYVALEEEIERNKESPVFAPVYF

PEELHRKAALEQDLAFWYGPRWQEVIPYTPAMQRYVKRLHEVGRTEPEL

LVAHAYTRYLGDLSGGQVLKKIAQKALDLPSSGEGLAFFTFPNIASATK

FKQLYRSRMNSLEMTPAVRQRVIEEAKTAFLLNIQLFEELQELLTHDTK

DKTHTCPPCPAPEAAGGPSVFLFPPKPKDTLMISRTPEVTCVVVDVSHE
```

-continued

```
DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSR

WQQGNVFSCSVMHEALHNHYTQKSLSLSPGGGGGSGGGGSGGGGSGGGG

SGGGGSGGGGSGGGGSGGGGSGEPKSSDKTHTCPPCPAPEAAGGPSVFL

FPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQ

KSLSLSPG
```

In some embodiments, recombinant heme oxygenase is an Fc fusion comprising SEQ ID NO: 39 (1-226-Fc V16; HO-1 underlined). In some embodiments, rHO-1-Fc fusion comprises a sequence that is at least 70%, 80%, 85%, 90%, 95%, 97%, 98%, 99% or 100% identical to SEQ ID NO: 39.

(SEQ ID NO: 39)

```
MERPQPDSMPQDLSEALKEATKEVHTQAENAEFMRNFQKGQVTRDGFKL

VMASLYHIYVALEEEIERNKESPVFAPVYFPEELHRKAALEQDLAFWYG

PRWQEVIPYTPAMQRYVKRLHEVGRTEPELLVAHAYTRYLGDLSGGQVL

KKIAQKALDLPSSGEGLAFFTFPNIASATKFKQLYRSRMNSLEMTPAVR

QRVIEEAKTAFLLNIQLFEELQELLTHDTKPAPPAAGGPSVFLFPPKPK

DTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREP

QVYTLPPSRDKLTKNQVSLTCLVKGFYPSDIAVEWESNGQPENNYKTTP

PVLDSDGSFFLYSKLTVDKSRWQQGNVFSCSVMHEALHNHYTQKSLSLS

PGGGGGSGGGGSGGGGSGGGGSGGGGSGGGGSGGGGSGGGGSGGGGSGG

GGSGGGGSGGGGSGGGGSPAPEAAGGPSVFLFPPKPKDTLMISRTPEVT

CVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDEL

TKNQVSLTCLVDGFYPSDIAVEWESNGQPENNYKTTPPVLDSDGSFFLY

SKLTVDKSRWQQGNVFSCSVMHEALHNHYTQKSLSLSPG
```

In some embodiments, recombinant heme oxygenase is an Fc fusion comprising SEQ ID NO:39 (1-226-Fc V16). In some embodiments, the rHO-1 Fc fusion is expressed with a signal peptide (SEQ ID NO: 60). In some embodiments, the signal peptide is cleaved. In some embodiments, rHO-1-Fc fusion comprises a sequence that is at least 70%, 80%, 85%, 90%, 95%, 97%, 98%, 99% or 100% identical to SEQ ID NO: 60 including the signal peptide shown in bold below.

(SEQ ID NO: 60)

```
MGWSCHILFLVATATGVHSMERPQPDSMPQDLSEALKEATKEVHTQAEN

AEFMRNFQKGQVTRDGFKLVMASLYHIYVALEEEIERNKESPVFAPVYF

PEELHRKAALEQDLAFWYGPRWQEVIPYTPAMQRYVKRLHEVGRTEPEL

LVAHAYTRYLGDLSGGQVLKKIAQKALDLPSSGEGLAFFTFPNIASATK
```

-continued

```
FKQLYRSRMNSLEMTPAVRQRVIEEAKTAFLLNIQLFEELQELLTHDTK

PAPEAAGGPSVFLFPPPKPKDTLMISRTPEVTCVVVDVSHEDPEVKFNWY

VDGVEVHNAKTKPREEQYNSTYRVVSVLTVLHQDWLNGKEYKCKVSNKA

LPAPIEKTISKAKGQPREPQVYTLPPSRDKLTKNQVSLTCLVKGFYPSD

IAVEWESNGQPENNYKTTPPVLDSDGSFFLYSKLTVDKSRWQQGNVFSC

SVMHEALHNHYTQKSLSLSPGGGGGSGGGGSGGGGSGGGGSGGGGSGGGG

GSGGGGSGGGGSGGGGSGGGGSGGGGSGGGGSGGGGSGGGGSPAPEAAGGPSVF

LFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKA

KGQPREPQVYTLPPSRDELTKNQVSLTCLVDGFYPSDIAVEWESNGQPE

NNYKTTPPVLDSDGSFFLYSKLTVDKSRWQQGNVFSCSVMHEALHNHYT

QKSLSLSPG
```

Linker or Spacer

An HO-1 domain may be directly or indirectly linked to an Fc domain. In some embodiments, a suitable recombinant HO-1 protein comprises a linker or spacer that joins a HO-1 domain and an Fc domain. An amino acid linker or spacer is generally designed to be flexible or to interpose a structure, such as an alpha-helix, between the two protein moieties. A linker or spacer can be relatively short, or can be longer. Typically, a linker or spacer comprises for example 3-100 (e.g., 5-100, 10-100, 20-100 30-100, 40-100, 50-100, 60-100, 70-100, 80-100, 90-100, 5-55, 10-50, 10-45, 10-40, 10-35, 10-30, 10-25, 10-20) amino acids in length. In some embodiments, a linker or spacer is equal to or longer than 2, 3, 4, 5, 6, 7, 8, 9, 10, 15, 20, 25, 30, 35, 40, 45, 50, 55, 60, 65, 70, 75, 80, 85, 90, 95, or 100 amino acids in length. Typically, a longer linker may decrease steric hindrance. In some embodiments, a linker will comprise a mixture of glycine and serine residues. In some embodiments, the linker may additionally comprise threonine, proline and/or alanine residues. Thus, in some embodiments, the linker comprises between 10-100, 10-90, 10-80, 10-70, 10-60, 10-50, 10-40, 10-30, 10-20, 10-15 amino acids. In some embodiments, the linker comprises at least 10, 15, 20, 25, 30, 35, 40, 45, 50, 55, 60, 65, 70, 75, 80, 85, 90, or 95 amino acids.

As non-limiting examples, linkers or spacers suitable for the present invention include but are not limited to:

(SEQ ID NO: 10)
```
GGGGS
```

(SEQ ID NO: 10)
```
(GGGGS)n
```

(SEQ ID NO: 11)
```
GGG;
```

(GAG linker, SEQ ID NO: 12)
```
GAPGGGGGAAAAAGGGGGGAP;
```

(GAG2 linker, SEQ ID NO:13)
```
GAPGGGGGAAAAAGGGGGGAPGGGGGAAAAAGGGGGGAP;
```

(GAG3 linker, SEQ ID NQ: 14)
```
GAPGGGGGAAAAAGGGGGGAPGGGGGAAAAAGGGGGGAPGGGGGAAAA
AGGGGGGAP;
and
```

(SEQ ID NQ: 65)
```
GGGGSGGGGSGGGGSGGGGSGGGGSGGGGS.
```

Suitable linkers or spacers also include those having an amino acid sequence at least 50%, 55%, 60%, 65%, 70%, 75%, 80%, 85%, 90%, 91%, 92%, 93%, 94%, 95%, 96%, 97%, 98%, 99% or more homologous or identical to the above exemplary linkers, e.g., GAG linker (SEQ ID NO:12), GAG2 linker (SEQ ID NO:13), or GAG3 linker (SEQ ID NO: 14). Additional linkers suitable for use with some embodiments may be found in US20120232021, filed on Mar. 2, 2012, the disclosure of which is hereby incorporated by reference in its entirety.

In some embodiments, a linker is provided that associates the HO-1 polypeptide with the Fc domain without substantially affecting the ability of the HO-1 polypeptide to bind to any of its cognate ligands (e.g., heme). In some embodiments, a linker is provided such that the binding of a HO-1 peptide to heme is not altered as compared to the HO-1 polypeptide alone.

Nucleotide Sequences

The present disclosure includes nucleotide sequences encoding one or more signal peptides, light chains, heavy chains, heavy chain constant domains, light chain constant domains, or other immunoglobulin-like sequences, antibodies, linker sequences, sequences comprising heme oxygenase proteins or fragments thereof, including variants, or binding molecules disclosed herein. In various instances, such nucleotide sequences may be present in a vector. In various instances such nucleotides may be present in the genome of a cell, e.g., a cell of a subject in need of treatment or a cell for production of a truncated protein or a fusion protein, e.g. a mammalian cell for production of a truncated protein or a fusion protein. In some embodiments, the nucleotide sequences for protein expression of HO-1 (e.g., truncated HO-1 and HO-1 Fc fusion proteins) are codon optimized. In some embodiments, the nucleotide sequences are codon optimized for protein expression to facilitate *E. coli* expression of HO-1. In some embodiments, the nucleotide sequences are codon optimized for protein expression to facilitate CHO cell expression of HO-1 Fc fusion proteins (e.g., 1-261-Fc V1-V4).

The term "Fc fragment", as used herein, refers to one or more fragments of an Fc region that retains an Fc function and/or activity described herein, such as binding to an Fc receptor.

In some embodiments, a multi-specific molecule described herein is an engineered antibody (e.g., engineered to have pH sensitive binding to antigen and to FcRn).

In some embodiments, a binding moiety is or includes an antibody (e.g., an IgG antibody, e.g., an IgG1, IgG2, or IgG3 antibody), or an antigen binding fragment, engineered to bind to a target (i.e., antigen) in an altered manner (e.g., in a pH sensitive manner, e.g., in a more or less pH sensitive manner) relative to a reference antibody or antigen binding fragment. For example, an antibody can be engineered by modifying (e.g., by adding, deleting, or substituting) an amino acid within one or more antibody CDRs and/or at a position involved in antibody CDR structure. Exemplary, non-limiting sites of an antibody that can be modified include the following (amino acid positions are indicated based on the Kabat numbering (Kabat et al., (1991) Sequences of Proteins of Immunological Interest, NIH)).

Heavy chain: H27, H31, H32, H33, H35, H50, H58, H59, H61, H62, H63, H64, H65, H99, H100b, and H102

Light chain: L24, L27, L28, L32, L53, L54, L56, L90, L92, and L94.

In some embodiments, one or more of these disclosed amino acids can be substituted with histidine, arginine, lysine, aspartic acid, glutamic acid, serine, threonine, asparagine, or glutamine. Without wishing to be bound by theory, it is believed that substituting an amino acid at one or more of these positions with a histidine can result in an antibody having pH-dependent antigen-binding properties. In some embodiments, a non-histidine residue is substituted with a histidine residue. In some embodiments, a histidine residue is substituted with a non-histidine residue. Additional engineered antigen binding regions include those described in, e.g., U.S. Publ. No. 20110229489.

In some instances, a binding moiety is or includes an antibody constant region, Fc region or Fc fragment that binds one or more Fc receptors (e.g., FcγRI, FcγRIIA, FcγRIIB, FcγRIIIA, FcγRIIIB, FcγRIV, or FcRn receptor). In some embodiments, a constant region, Fc region or Fc fragment is engineered to bind to a target (e.g., an Fc receptor) in an altered manner (e.g., in a pH sensitive manner, e.g., in a more or less pH sensitive manner) relative to a reference constant region, Fc region or Fc fragment.

In some instances, a binding moiety can be or include a constant region, Fc region or Fc fragment of an IgG antibody engineered to include an amino acid addition, deletion, or substitution, of one or more of amino acid residues described herein (e.g., 251-256, 285-290, 308-314, 385-389, and 428-436 (Kabat numbering (Kabat et al., (1991) Sequences of Proteins of Immunological Interest, NIH))).

Recombinant Gene Technology

In accordance with the present disclosure, there may be employed conventional molecular biology, microbiology, and recombinant DNA techniques within the skill of the art. Such techniques are described in the literature (see, e.g., Sambrook, Fritsch & Maniatis, Molecular Cloning: A Laboratory Manual, Second Edition (1989) Cold Spring Harbor Laboratory Press, Cold Spring Harbor, N.Y.; DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells and Enzymes (IRL Press, (1986)); B. Perbal, A Practical Guide To Molecular Cloning (1984); F. M. Ausubel et al. (eds.), Current Protocols in Molecular Biology, John Wiley & Sons, Inc. (1994).

Recombinant expression of a gene, such as a nucleic acid encoding a polypeptide, such as an engineered antibody described herein, can include construction of an expression vector containing a nucleic acid that encodes the polypeptide. Once a polynucleotide has been obtained, a vector for the production of the polypeptide can be produced by recombinant DNA technology using techniques known in the art. Known methods can be used to construct expression vectors containing polypeptide coding sequences and appropriate transcriptional and translational control signals. These methods include, for example, in vitro recombinant DNA techniques, synthetic techniques, and in vivo genetic recombination.

An expression vector can be transferred to a host cell by conventional techniques, and the transfected cells can then be cultured by conventional techniques to produce polypeptides.

Methods of Treatment

The present disclosure also provides a recombinant heme oxygenase-1 (rHO-1) of the invention for use in a method of treating sickle cell disease in a subject in need of such treatment. As described herein, the present disclosure provides a method of treating sickle cell disease comprising administering to a subject in need of treatment a recombinant heme oxygenase-1 (rHO-1). The present disclosure also provides a recombinant heme oxygenase-1 (rHO-1) of the invention for use in the manufacture of a medicament for treating sickle cell disease in a subject in need of such treatment.

In some embodiments, recombinant heme oxygenase protein is administered intravenously.

In some embodiments, administration of recombinant heme oxygenase to a subject results in a reduction of free heme level in serum by 95%, 90%, 85%, 80%, 75%, 70%, 65%, 60%, 55% or 50% compared to a control sample. The control sample can be a serum sample taken from the subject prior to treatment with the recombinant heme oxygenase.

In some embodiments, administration of recombinant heme oxygenase results in reduced free heme level in serum. In some embodiments, free heme levels in serum are reduced by about 90%, 80%, 70%, 60%, 50%, 40%, 30%, 25%, 20%, 15%, 10%, 5%, or 2%. In some embodiments, free heme levels are reduced by 5 $\mu$M, 10 $\mu$M, 11, 12, 13, 14, 15 $\mu$M, 16 $\mu$M, 17 $\mu$M, 18 $\mu$M, 19 $\mu$M, 20 UM or more to approach levels in healthy adults (e.g., about 20 $\mu$M).

In some embodiments, administration of recombinant heme oxygenase to a subject results in increased recombinant heme oxygenase activity by 2%, 5%, 10%, 15%, 20%, 25%, 30%, 35%, 40%, 45%, 50%, 60%, 65%, 70%, 75%, 80%, 85%, 90%, 95%, 99% or more in serum relative to a control individual. In some embodiments, administration of recombinant heme oxygenase to a subject results in increased recombinant heme oxygenase activity by 2-fold, 3-fold, 4-fold, 5-fold, 10-fold, 50-fold, 100-fold, or more in serum relative to a control individual. The control individual can be the subject prior to administration of recombinant heme oxygenase.

In some embodiments, a control individual has endogenous HO-1 levels of approximately 1 ng/ml (See e.g., Bao, et al. PLOS, 2010).

In some embodiments, administration of recombinant heme oxygenase results in increased recombinant HO-1 activity in serum at or above 2%, 5%, 10%, 15%, 20%, 25%, 30%, 35%, 40%, 45%, 50%, 55%, 60%, 65%, 70%, 75%, 80%, 85%, 90%, 95%, 99% or more relative to normal serum HO-1 activity in a healthy individual.

In some embodiments, administration of recombinant heme oxygenase to a subject in need of treatment results in HO-1 activity in serum at or above 2%, 5%, 10%, 15%, 20%, 25%, 30%, 35%, 40%, 45%, 50%, 55%, 60%, 65%, 70%, 75%, 80%, 85%, 90%, 95%, 99% of normal serum HO-1 activity in a healthy individual.

In some embodiments, administration of recombinant heme oxygenase results in amelioration of symptoms of sickle cell disease, including reduced or delayed onset of anemia, vasoocclusive crises (VOC), acute chest syndrome (ACS), pulmonary hypertension or organ damage.

In some embodiments, administration of recombinant heme oxygenase results in peripheral blood oxygen saturation values above 90%, 92%, 94%, 96%, 98%, or 99%.

In some embodiments, administration of recombinant heme oxygenase to a subject results in an increase in peripheral blood oxygen saturation values by at least 50%, 55%, 60%, 65%, 70%, 75%, 80%, 85%, 90%, 95%, or 95% compared to a control. The control can be peripheral blood oxygen saturation values taken from the subject prior to treatment with the recombinant heme oxygenase.

In some embodiments, administration of recombinant heme oxygenase results in 20%, 25%, 30%, 35%, 40%, 45%, 50%, 55%, 60% increase in breaths per minute, approaching 12-18 breaths per minute in normal healthy humans.

In some embodiments, administration of recombinant heme oxygenase results in 20%, 25%, 30%, 35%, 40%, 45%, 50%, 55%, 60% improvement in heart rate per minute, approaching 60-100 bpm in normal healthy humans.

Pharmaceutical Composition and Administration

The present invention further provides pharmaceutical compositions comprising therapeutically active ingredients in accordance with the invention (e.g., recombinant heme oxygenase protein, recombinant heme oxygenase fusion protein or recombinant heme oxygenase-Fc fusion protein), together with one or more pharmaceutically acceptable carriers or excipients. Such pharmaceutical compositions may optionally comprise one or more additional therapeutically-active substances.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

Formulations of the pharmaceutical compositions described herein may be prepared by any method known or hereafter developed in the art of pharmacology. In general, such preparatory methods include the step of bringing the active ingredient into association with a diluent or another excipient or carrier and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient or carrier, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations may additionally comprise a pharmaceutically acceptable excipient or carrier, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21st Edition, A. R. Gennaro (Lippincott, Williams & Wilkins, Baltimore, MD, 2006; incorporated herein by reference) discloses various excipients used in formulating pharmaceutical compositions and known techniques for the preparation thereof. Except insofar as any conventional excipient medium or carrier is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient or carrier is at least 95%, at least 96%, at least 97%, at least 98%, at least 99%, or 100% pure. In some embodiments, an excipient or carrier is approved for use in humans and for veterinary use. In some embodiments, an excipient or carrier is approved by United States Food and Drug Administration. In some embodiments, an excipient or carrier is pharmaceutical grade. In some embodiments, an excipient or carrier meets the standards of the United States Pharmacopoeia (USP), the European Pharmacopoeia (EP), the British Pharmacopoeia, and/or the International Pharmacopoeia.

Pharmaceutically acceptable excipients or carriers used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients or carriers may optionally be included in pharmaceutical formulations. Excipients or carriers such as cocoa butter and suppository waxes, coloring agents, coating agents, sweetening, flavoring, and/or perfuming agents can be present in the composition, according to the judgment of the formulator.

Suitable pharmaceutically acceptable excipients or carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interfere with their activity. In a preferred embodiment, a water-soluble carrier suitable for intravenous administration is used.

A suitable pharmaceutical composition or medicament, if desired, can also contain minor amounts of wetting or emulsifying agents, or pH buffering agents. A composition can be a liquid solution, suspension, emulsion, tablet, pill, capsule, sustained release formulation, or powder. A composition can also be formulated as a suppository, with traditional binders and carriers such as triglycerides. Oral formulations can include standard carriers such as pharmaceutical grades of mannitol, lactose, starch, magnesium stearate, polyvinyl pyrrolidone, sodium saccharine, cellulose, magnesium carbonate, etc.

A pharmaceutical composition or medicament can be formulated in accordance with the routine procedures as a pharmaceutical composition adapted for administration to human beings. For example, in some embodiments, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

A recombinant heme oxygenase protein or recombinant heme oxygenase-Fc fusion protein described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

General considerations in the formulation and/or manufacture of pharmaceutical agents may be found, for example, in *Remington: The Science and Practice of Pharmacy* 21st ed., Lippincott Williams & Wilkins, 2005 (incorporated herein by reference).

Routes of Administration

A recombinant heme oxygenase protein or recombinant heme oxygenase-Fc fusion protein described herein (or a composition or medicament containing a recombinant heme oxygenase protein described herein) is administered by any appropriate route. In some embodiments, a recombinant heme oxygenase protein, recombinant heme oxygenase-Fc fusion protein or a pharmaceutical composition containing the same is administered systemically. Systemic administration may be intravenous, intradermal, inhalation, transdermal (topical), intraocular, intramuscular, subcutaneous, intramuscular, oral and/or transmucosal administration. In some embodiments, a recombinant heme oxygenase protein, recombinant heme oxygenase-Fc fusion protein or a pharmaceutical composition containing the same is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, the thigh region, abdominal region, gluteal region, or scapular region. In some embodiments, a recombinant heme oxygenase protein, recombinant heme oxygenase-Fc fusion protein or a pharmaceutical composition comprising the same is administered intravenously. In some embodiments, a recombinant heme oxygenase protein, recombinant heme oxygenase-Fc fusion protein or a pharmaceutical composition containing the same is administered orally. In some embodiments, a recombinant heme oxygenase protein, recombinant heme oxygenase-Fc fusion protein or a pharmaceutical composition containing the same is administered intramuscularly. In some embodiments, more than one route can be used concurrently.

In some embodiments, administration results only in a localized effect in an individual, while in other embodiments, administration results in effects throughout multiple portions of an individual, for example, systemic effects. Typically, administration results in delivery of a recombinant heme oxygenase protein or recombinant heme oxygenase-Fc fusion protein systemically. In some embodiments, the recombinant heme oxygenase protein or recombinant heme oxygenase-Fc fusion protein is delivered to one or more target tissues including, but not limited to, heart, brain, spinal cord, striated muscle (e.g., skeletal muscle), smooth muscle, kidney, liver, lung, and/or spleen.

Dosage Forms and Dosing Regimen

In some embodiments, a composition is administered in a therapeutically effective amount and/or according to a dosing regimen that is correlated with a particular desired outcome (e.g., with treating or reducing risk for sickle cell disease).

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, etc., or combinations thereof). Such doses or amounts can be determined by those of ordinary skill. In some embodiments, an appropriate dose or amount is determined in accordance with standard clinical techniques. Alternatively or additionally, in some embodiments, an appropriate dose or amount is determined through use of one or more in vitro or in vivo assays to help identify desirable or optimal dosage ranges or amounts to be administered.

In various embodiments, a recombinant heme oxygenase protein is administered at a therapeutically effective amount. Generally, a therapeutically effective amount is sufficient to achieve a meaningful benefit to the subject (e.g., treating, modulating, curing, preventing and/or ameliorating the underlying disease or condition). In some particular embodiments, appropriate doses or amounts to be administered may be extrapolated from dose-response curves derived from in vitro or animal model test systems.

In some embodiments, a provided composition is provided as a pharmaceutical formulation. In some embodiments, a pharmaceutical formulation is or comprises a unit dose amount for administration in accordance with a dosing regimen correlated with achievement of the reduced incidence or risk of sickle cell disease.

In some embodiments, a formulation comprising a recombinant heme oxygenase protein or recombinant heme oxygenase-Fc fusion protein described herein administered as a single dose. In some embodiments, a formulation comprising a recombinant heme oxygenase protein or recombinant heme oxygenase-Fc fusion protein described herein is administered at regular intervals. Administration at an "interval," as used herein, indicates that the therapeutically effective amount is administered periodically (as distinguished from a one-time dose). The interval can be determined by standard clinical techniques. In some embodiments, a formulation comprising a recombinant heme oxygenase protein or recombinant heme oxygenase-Fc fusion protein described herein is administered bimonthly, monthly, twice monthly, triweekly, biweekly, weekly, twice weekly, thrice weekly, daily, twice daily, or every six hours. The administration interval for a single individual need not be a fixed interval, but can be varied over time, depending on the needs of the individual.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

In some embodiments, a formulation comprising a recombinant heme oxygenase protein or recombinant heme oxygenase-Fc fusion protein described herein is administered at regular intervals indefinitely. In some embodiments, a formulation comprising a recombinant heme oxygenase protein or recombinant heme oxygenase-Fc fusion protein described herein is administered at regular intervals for a defined period.

As described herein, the term "therapeutically effective amount" is largely determined based on the total amount of the therapeutic agent contained in the pharmaceutical compositions of the present invention. A therapeutically effective amount is commonly administered in a dosing regimen that may comprise multiple unit doses. For any particular composition, a therapeutically effective amount (and/or an appropriate unit dose within an effective dosing regimen) may vary, for example, depending on route of administration or on combination with other pharmaceutical agents.

In some embodiments, administration of a recombinant heme oxygenase protein or recombinant heme oxygenase-Fc fusion protein reduces the intensity, severity, or frequency, or delays the onset of at least one sickle cell disease sign or symptom. In some embodiments administration of a recombinant heme oxygenase protein or recombinant heme oxygenase-Fc fusion protein reduces the intensity, severity, or frequency, or delays the onset of at least one sickle cell disease sign or symptom selected from the group consisting of vasoocclusion, acute chest syndrome, or organ damage.

In some embodiments, administration of a recombinant heme oxygenase protein or recombinant heme oxygenase-Fc fusion protein results in improved clinical outcomes as measured by increased real-time peripheral arterial blood oxygen saturation, breath rate, heart rate, pulse distention and reduced lung wet/dry ratio.

TABLE 2

| | | | | | |
|---|---|---|---|---|---|
| | | | | rHO-1-Fc fusion proteins | |
| Name | HO-1 Seq | Linker | IgG1 FcLALA Position | Heterodimeric Mutations on IgG1 FcLALA | Format |
| HO1-Fc-v1 | 1-261 | no linker | C-terminal fusion | Wild-type | Homodimer Fc bivalent |
| HO1-Fc-v2 | 1-261 | (GGG GS)₄ linker (SEQ ID NO: 21) | C-terminal fusion | Wild-type | Homodimer Fc bivalent |
| HO1-Fc-v3 | 1-261 | (GGG GS)₄ linker (SEQ ID NO: 21) | N-terminal fusion | Wild-type | Homodimer Fc bivalent |

TABLE 2-continued

| | | | | | Heterodimeric | |
| | HO-1 | | IgGl FcLALA | | Mutations on | |
| Name | Seq | Linker | Position | | IgG1 FcLALA | Format |
| --- | --- | --- | --- | --- | --- | --- |
| HO1-Fc-v4 | 1-261 | no linker | C-terminal fusion | Wild-type | Chain A: T350V/L351Y/F405A/Y407V Chain B: T350V/T366L/K392L/T394W | monovalent |
| HO1-Fc-v5 | 1-261 | no linker | N-terminal fusion | Knob-Hole S-S | Chain A: T366W, S354C; Chain B: T366S, L368A, Y407V, Y349C | monovalent |
| HO1-Fc-v6 | 1 -261 | no linker | N-terminal fusion | DD-KK | Chain A: K392D, K409D; Chain B: D399K E356K | monovalent |
| HO1-Fe-v7 | 1-261 | no linker | N-terminal fusion | EW-RVT S-S | Chain A: K360E, K409W, Y349C; Chain B: Q347R, D399V, F405T, S354C | monovalent |
| HO1-Fc-v8 | 1-261 | no linker | C-terminal fusion | Knob-Hole | Chain A: T366W; Chain B: T366S, L368A, Y407V | monovalent |
| HO1-Fc-v9 | 1-261 | no linker | C-terminal fusion | EW-RVT | Chain A: K360E, K409W Chain B: Q347R, D399V, F405T | monovalent |
| HO1-Fc-v10 | 1-226 | no linker | C-terminal fusion | | Chain A: T350V/L351Y/F405A/Y407V Chain B: T350V/T3 66L/K3 92L/T3 94W | monovalent |
| HO1-Fc-v11 | 1-226 | no linker | N-terminal fusion | Wild-type | | homodimer Fc |
| HO1-Fc-v12 | 1-226 | no linker | C-terminal fusion | Wild-type | | homodimer Fc |
| HO1-Fc-v13 | 1-261 | no linker | C-terminal fusion | Wild-type | | single chain (G4S)$_8$ (SEQ ID NO: 63) monovalent |
| HO1-Fc-v14 | 1-261 | no linker | C-terminal fusion | K-D | Reverse charge mutations: Chain A: E357K; Chain B: K370D | single chain (G4S)$_{13}$ (SEQ ID NO: 64) monovalent |
| HO1-Fc-v15 | 1-226 | no linker | C-terminal fusion | Wild-type | | single chain (G4S)$_8$ (SEQ ID NO: 63) monovalent |
| HO1-Fc-v16 | 1-226 | no linker | C-terminal fusion | K-D | Reverse charge mutations: Chain A: E357K; Chain B: K370D | single chain (G4S)$_{13}$ (SEQ ID NO: 64) monovalent |

Examples

The following examples describe some of the preferred modes of making and practicing the present invention. However, it should be understood that these examples are for illustrative purposes only and are not meant to limit the scope of the invention.

Example 1. Production of Truncated Recombinant Human Heme-Oxygenase 1 (rHO-1)

This example illustrates expression of recombinant heme oxygenase (rHO-1). A series of recombinant heme oxygenase (rHO) truncated proteins were engineered with a His-tag at the C-terminal end. Five truncated variants (1-226, 1-233, 1-237, 1-261, 1-265) were assessed for expression in *E. coli*. All truncated HO-1 constructs showed stable expression and solubility. His-1-261 was selected for further purification and evaluation.

A 2 L culture of BL21 (DE3) cells expressing rHO-1 was centrifuged and was lysed in PBS buffer containing 5 mM imidazole in the presence of a protease inhibitor. His-tag rHO-1 was affinity purified using Ni-FF XK 16/20 column eluted with 500 mM imidazole PBS elution buffer. rHO-1-His fractions were pooled and desalted.

rHO-1-His was further purified using a Superdex® 75 SEC column. Purified rHO-1 protein was onto Detoxi-Gel™ Endotoxin Removing Gel column for resulting in a final endotoxin level of 1.10 Eu/mg. Purity was determined to be 95% by SDS-PAGE and a protein yield of 160 mg was achieved in a final concentration of 4.02 mg/ml.

Example 2. Enzymatic Activity of Purified rHO-1

This example demonstrates enzymatic activity of purified rHO-1. HO-1 was incubated with hemin, BSA, and catalase enzyme. Rat Kidney Cytosolic Fraction was added to the reaction to provide sufficient biliverdin reductase. The reaction was started by the addition of 1 mM β-NADPH and incubated at 37° C. for 30 minutes. The reaction was stopped by placing on ice.

Chloroform was vortexed on ice, added to the reaction mixture, mixed 3×in the dark, centrifuged at 1000 rpm for 2 minutes to separate organic phases cleanly. Formed bilirubin was extracted in the chloroform phase and collected from the bottom of the tube into a fresh amber colored tube on ice. Spectrophotometric absorbance was measured between 420-540 nm in a 1 cm path length quartz cuvette.

Figure 1A:
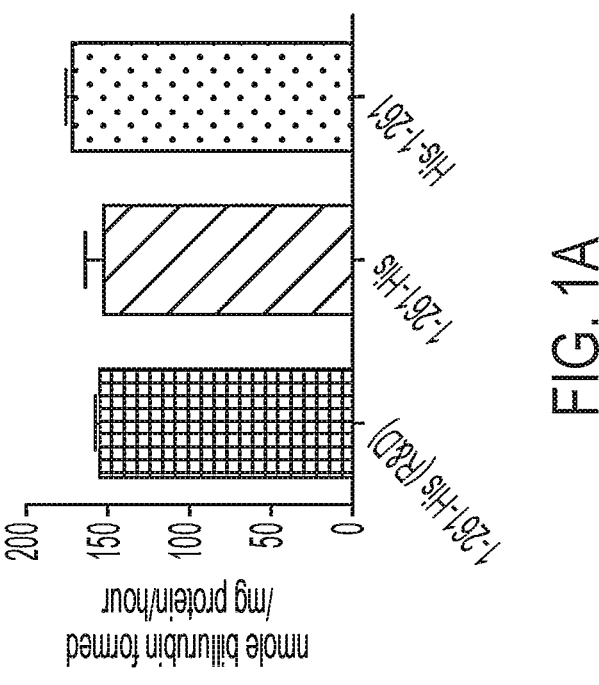
FIG. 1A shows exemplary results of HO-1 enzymatic activity measured by nmole bilirubin product formed per mg of recombinant heme oxygenase per hour.

Heme oxygenase activity was calculated as bilirubin product formed (nmol)/mg protein/hr using the extinction coefficient of bilirubin as 58 mM/cm. Enzymatic activity of truncated rHO-1 is shown in FIGS. 1A and 1B and Table 3.

TABLE 3

| Enzymatic activity of 1-261-His and His-1-261 | | | |
|---|---|---|---|
| Michaelis-Menten (Best fit values) | 1-261-His (R&D) | 1-261-His | His-1-261 |
| Vmax | 0.3332 | 0.3456 | 0.3523 |
| Km | 0.1401 | 0.1767 | 0.1874 |

Example 3. Pharmacokinetic (PK) Profile and In Vivo Efficacy of rHO-1-his in Mice This example illustrates that systemic administration of recombinant heme oxygenase (HO-1) in mice showed a trend of increased survival following hemin challenge and amelioration of symptoms of sickle cell disease.

Transgenic Townes sickle mouse model (SS mice) was used since it recapitulates many of the major pathophysiologic aspects of SCD, in particular vaso-occlusive crises (VOC) and Acute Chest Syndrome (ACS) (See Ghosh et al., 2013 *J Clin Invest.* 2013; 123 (11): 4809-4820). Free heme triggers Acute Chest Syndrome with severe hypoxemia and death in sickle cell mice. The SS transgenic Sickle cell disease mouse model mimics chronic anemia seen in human disease. Similarly, in SS mice, extracellular heme triggers hemolysis and VOC/ACS.

Both young (4-6 weeks) and adult (12 weeks or and older) SS mice suffer hemolytic crises when challenged with intravenous hemin (35 micromoles/kg bw). However, the young mice do not develop acute lung injury (ALI) while the adults succumb to respiratory failure. The young mice rapidly cleared excess heme from the circulation suggesting this may be the reason for their resistance to intravenous hemin. Interestingly, the young mice had significantly lower plasma hemopexin levels compared to the adult mice excluding the classical heme scavenging pathway for their resistance.

Figure 2:
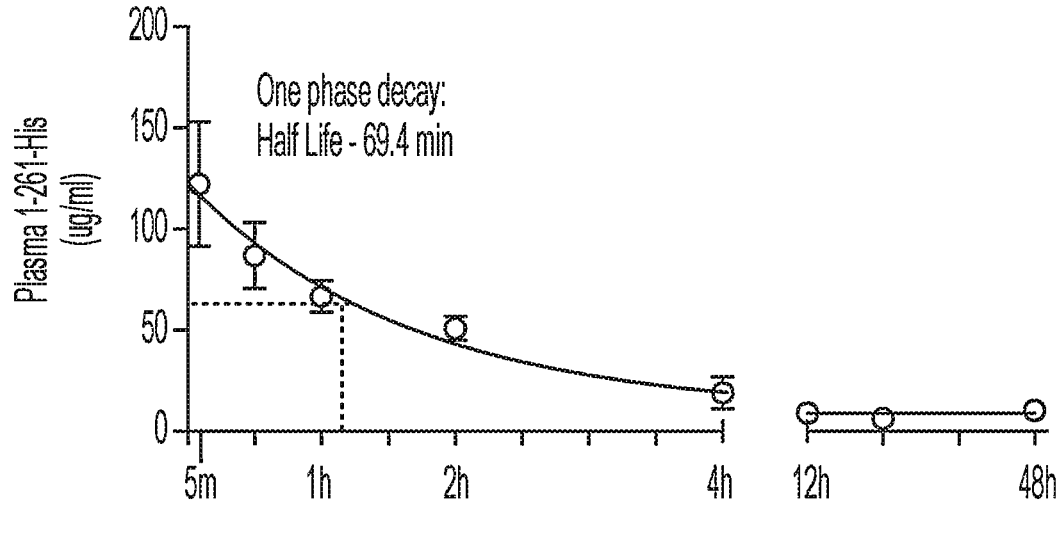
FIG. 2 shows exemplary results of pharmacokinetic analysis of 1-261-His in transgenic Townes sickle mice (SS mice).

SS mice were systemically administered a single dose of 5 mg/kg of 1-261-His or vehicle control intravenously. Blood was collected at 5 minutes, 1 hour, 2 hours, 4 hours, 12 hours and 48 hours after injection of rHO-1-His. and plasma separated for analysis. As shown in FIG. 2, 1-261-His exhibited a one-phase decay with a half-life of 69.4 minutes. A 2 log difference in levels of plasma HO-1 was observed in animals injected with HO-1-His within 48h. (FIG. 2).

Figure 3:
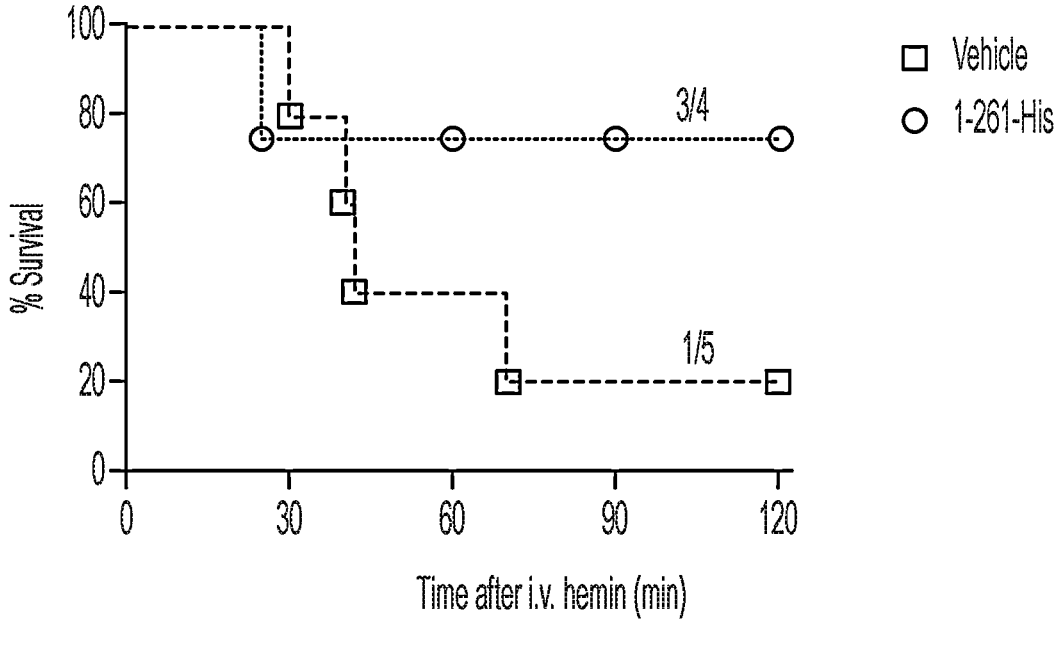
FIG. 3 shows exemplary results of survival of transgenic SCD mice infused with purified hemin to induce ACS treated with 1-261-His or a vehicle control.
Figure 4B:
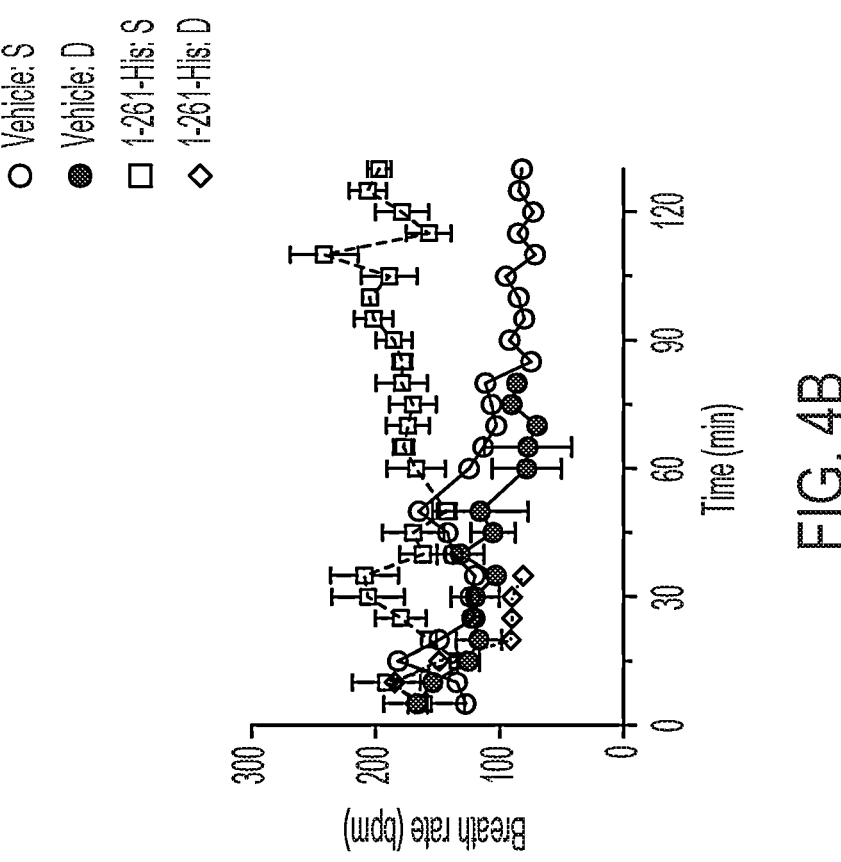
FIG. 4B shows exemplary results of breath rate measurements of transgenic SCD mice infused with purified hemin to induce ACS treated with 1-261-His or a vehicle control.
Figure 4A:
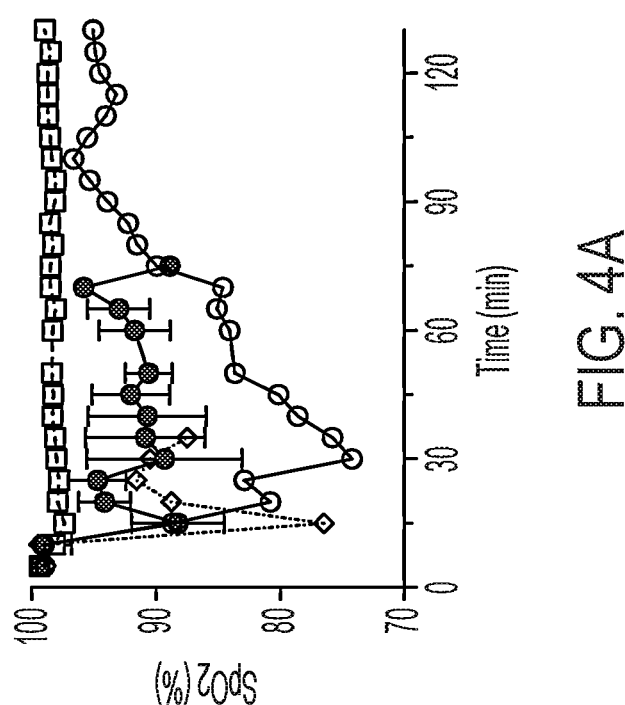
FIG. 4A shows exemplary results of real-time oxygen saturation of transgenic SCD mice infused with purified hemin to induce ACS treated with 1-261-His or a vehicle control.
Figure 4D:
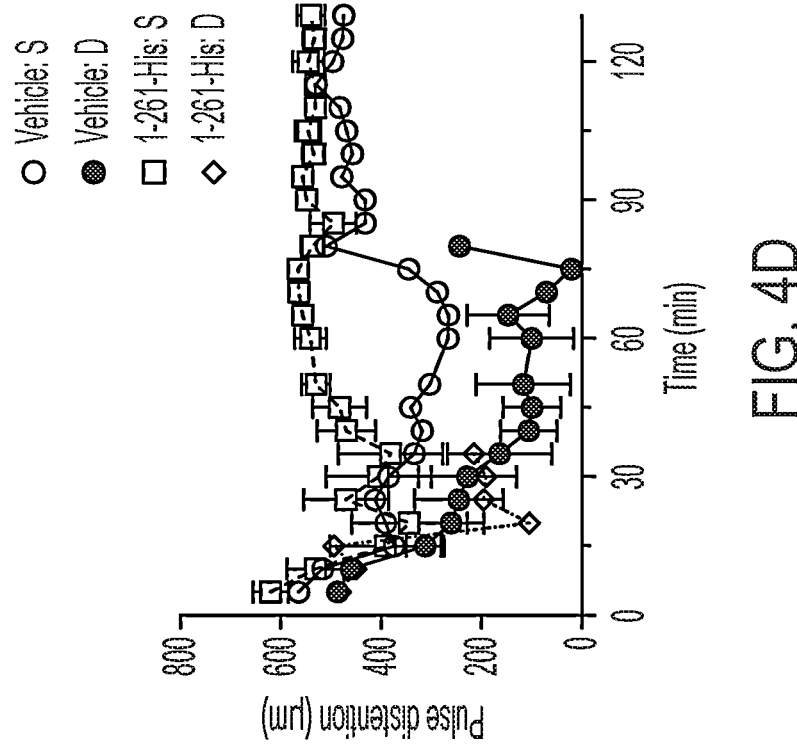
FIG. 4D shows exemplary results of pulse distention measurements of transgenic SCD mice infused with purified hemin to induce ACS treated with 1-261-His or a vehicle control.
Figure 4C:
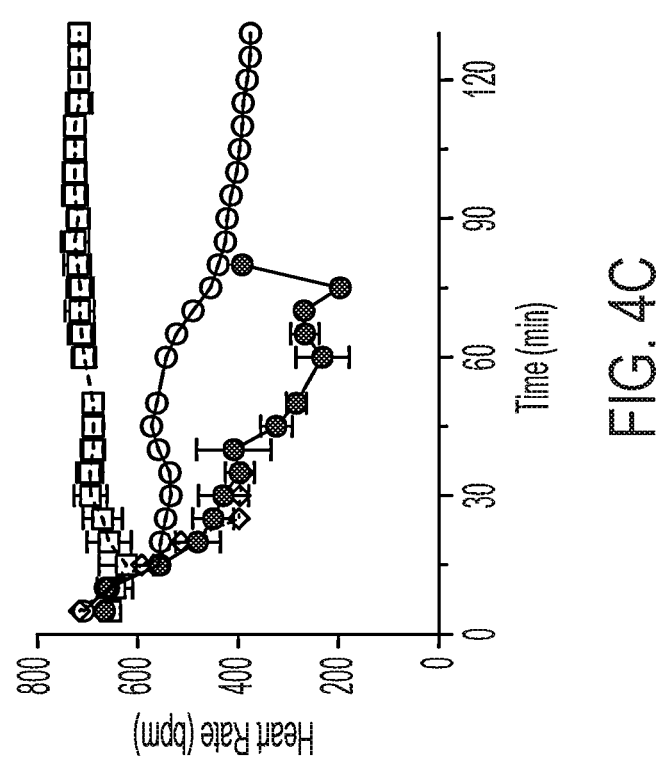
FIG. 4C shows exemplary results of heart-rate measurements of transgenic SCD mice infused with purified hemin to induce ACS treated with 1-261-His or a vehicle control.
Figure 4E:
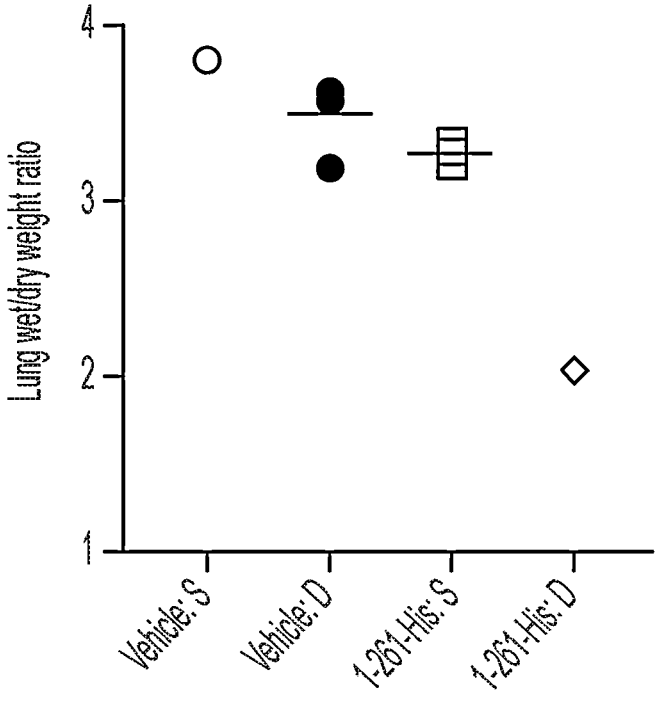
FIG. 4E shows exemplary wet/dry weight ratios of the lungs of transgenic SCD mice infused with purified hemin to induce ACS treated with 1-261-His or vehicle control. S and D denotes mice that survived(S) or died (D) from the ACS.

To evaluate survival in SS Mice following treatment with 1-261-His and heme-induced acute-chest syndrome. Transgenic SS mice with human HbS were systemically injected with 5 mg/kg 1-261-His or vehicle control and monitored for survival following intravenous administration of 35 μmol/kg heme up to 120 minutes after delivery. 75% mice receiving heme oxygenase survived 120 minutes after delivery (FIG. 3).

Response following in vivo treatment with 1-261-His was monitored by evaluating real time oxygen saturation, breath rate, heart rate, pulse distention and lung wet/dry ratio as surrogate clinical outcomes (FIG. 4A-4E).

Peripheral arterial oxygen saturation in blood (% SpO2) was measured in real time by pulse oximetry up to 120 minutes following treatment with hemin. Pulse oximetry uses spectrophotometry to determine the proportion of hemoglobin that is saturated with oxygen (i.e., oxygenated hemoglobin; oxyhemoglobin) in peripheral arterial blood. Light, at two separate wavelengths, illuminates oxygenated and deoxygenated hemoglobin in blood. The ratio of light absorbance between oxyhemoglobin and the sum of oxyhemoglobin plus deoxyhemoglobin is calculated and compared with previously calibrated direct measurements of arterial oxygen saturation (SaO2) to establish an estimated measure of peripheral arterial oxygen saturation (SpO2). Pulse oximeter probes consist of two light-emitting diodes and a photodetector. Deoxyhemoglobin absorbs light maximally in the red band of the spectrum (600 to 750 nm), and oxyhemoglobin absorbs maximally in the infrared band (850 to 1000 nm). Thus, the emitters emit light at 660 nm and 940 nm for optimal detection of these two substances. Peripheral arterial oxygen saturation is used as a biomarker for tissue oxygenation. In this exemplary study, increased oxygen saturation was observed in SS mice following a 35 μmol/kg hemin challenge.

Breath rate per minute was measured in real time was measured by pulse oximetry up to 120 minutes following treatment with hemin. The MouseOx® pulse-oximeter (Starr Life Sciences) was used to measure real-time SpO2 (percentage of functional arterial Hb) and breath rate per minute in awake conditions. Hairs from the collar region (back of the neck) were removed using a depilatory agent 1 day before actual measurement. A disposable sensory collar clip attached to the pulse-oximeter was placed on the hairless area, and measurements were initiated through MouseOx® software (version 6.3; provided by the manufacturer) when data displays were without error codes. Recorded values were pooled for each consecutive 5-minute interval, and mean values were used for analysis where continuous screening was presented. Breath rate is derived from respiratory effort and not airflow and will be present even if the animal is experiencing obstructive apnea.

Heart rate per minute was measured in real time cardiac pulse rate (bpm) up to 120 minutes following treatment with hemin. The MouseOx® pulse-oximeter (Starr Life Sciences) was used to carry out measurements. Pulse distention was measured in real time up to 120 minutes following treatment with hemin. Pulse distention is a measurement of the change in distention of the arterial blood vessels residing between the sensors pads due to a cardiac output pulse. It is a direct measurement of changes in local blood volume that accompany each cardiac pulse. For a given vascular compliance, pulse distention can also provide a surrogate for pulse pressure.

Pulse distention was measured in real time up to 120 minutes following treatment with hemin. Pulse distention is a measure of change in the effect path length of light that passes through the arterial or pulsating blood and has true linear distance unites of μm. Pulse distention provides a measure of arterial blood available to make oximetry measurement for parameters such as blood oxygen saturation, heart rate and breath rate.

Lung wet/dry ratio was measured up to 120 minutes following treatment with hemin. Higher lung wet/dry weight ratio is indicative of lung edema, and is a biomarker of Acute Chest Syndrome. The whole lungs were harvested from mice, either immediately after death or 2 hours after hemin injection, and weighed using an isometric transducer. Lungs were then dried in an oven at 80° C. containing desiccant crystals for 24 hours, dry weight was determined, and lung wet/dry weight ratios were calculated.

Mice treated with 1-261-His showed HO-1 level with a half-life of 69.4 min. Mice treated with 1-261-His showed increased survival, increased oxygen saturation, breath rate, heart rate and decreased lung wet/dry ratio in SS mice following a 35 μmol/kg hemin challenge.

Example 4. In Vitro Activity and PK Analysis of HO-1-Fc Fusion Proteins

This example illustrates the development of HO-1 fusion proteins designed to increase the half-life of recombinant HO-1.

Four Fc fusion constructs were engineered using truncated rHO-1 protein fused with an Fc domain. 1-261-Fc V1 (SEQ ID NO: 3) was produced using HEK293 cells. V2 (SEQ ID NO: 4), V3 (SEQ ID NO: 5) and V4 (SEQ ID NO: 6) were produced using ExpiCHO cells (FIG. 5A-5E).

Expression plasmids encoding the 1-261-Fc fusion constructs (V1, V2 and V3) or two plasmids encoding chains A and B respectively (V4) were transfected with PEI. Conditioned medium was harvested 9 days post transfection by centrifugation and filtration. 1-261-Fc proteins were purified from conditioned medium by binding and elution from MabSelect SuRe. Eluates from MabSeclect SuRe were further purified using a Superdex® 200 column and 1-261-Fc containing fractions were pooled. Purified protein was analyzed by SDS-PAGE and SEC-HPLC.

This example illustrates that systemic administration of 1-261-Fc fusion protein in mice showed extended half-life.

Figure 6:
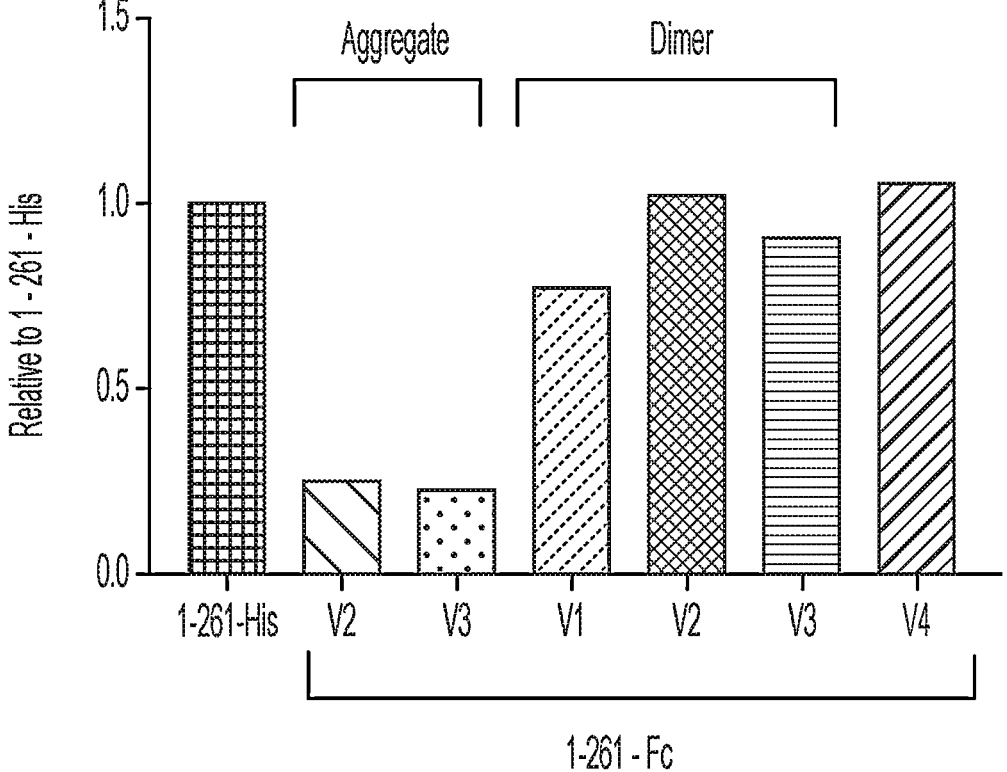
FIG. 6 shows exemplary results of enzymatic activity of 1-261-Fc fusion forms relative to 1-261-His and also compares the activity of V2 and V3 aggregates.

Enzymatic activity of V1, V2, V3 and V4 Fc fusion proteins was measured in vitro. rHO-1 (80 μg/ml) was incubated with hemin (60 μM), BSA (4 mg/mL), Cytochrome P450 Reductase (80 g/mL). Biliverdin Reductase A (80 μg/mL) and catalase (1000 U/mL). Read absorbance at 468 nm (bottom read) in kinetic mode for 5 minutes at 37° C. after the reaction was started by the addition of 1 mM β-NADPH. 1-261-Fc fusion proteins V1, V2, V3 and V4 had similar activity profiles as 1-261-His protein. V2 and V3 aggregates showed lower activity than the 1-261-His control (FIG. 6).

Figure 7:
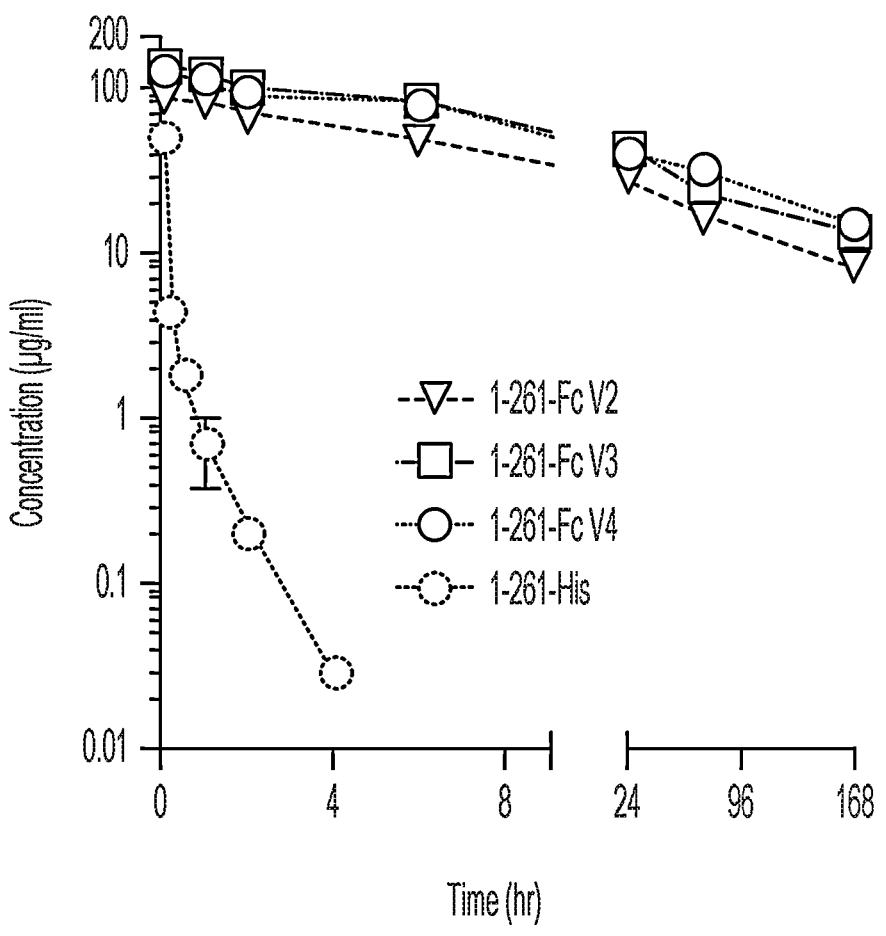
FIG. 7 shows exemplary results of a pharmacokinetic profile of 1-261-Fc V2, V3 and V4 fusion constructs in SS mice relative to 1-261-His.

To evaluate the pharmacokinetic profile of the HO-1 Fc fusion proteins, WT CD1 mice (4 mice per time points) were administered intravenous injections of V2, V3, V4 and 1-261-His. Plasma rHO-1 levels were measured by ELISA assay as described in Example 3. As shown in Table 4, V2, V3 and V4 demonstrated showed extended half life and were detectable at 168 hours and 1-261-His had a half-life of approximately 40 min (0.67 h) (FIG. 7).

TABLE 4

| In vivo PK parameters of rHO-1 proteins | | | | |
|---|---|---|---|---|
| Construct | Terminal half-life (hr) | $C_0$ (μg/mL) | $AUC_{0-168\ hr.}$ (hr* ug/mL) | Clearance (mL/r/kg) |
| 1-261-Fc V2 | 85 | 84 | 3321 | 1.15 |
| 1-261-Fc V3 | 92 | 129 | 5053 | 0.730 |
| 1-261-Fc V4 | 101 | 128 | 5568 | 0.641 |
| 1-261-His | 0.67 | 173 | 15.9 | 14 |

Example 5. In Vivo Efficacy of Fc Fusion Heme Oxygenase Truncated Proteins

This example illustrates the in vivo efficacy of recombinant heme oxygenase Fc fusion proteins in increasing survival in mice that received the treatment. Young SS mice have 2-fold higher plasma HO-1 than adult mice. Fractionization experiments showed that HO-1 co-localizes with the enzymatic and co-factor machinery required for heme degradation in the plasma affirming that heme can be degraded in the plasma. To determine whether young SS mice use HO-1 to rapidly degrade circulating heme, 3 week old animals were treated with an HO-1 inhibitor (tin protoporphyrin (SnPP)) or vehicle. Seven days later, the animals were challenged with hemin to induce ALI/ACS. A majority (10/12; 83%) of the vehicle-treated mice survived, while the SnPP-treated mice (10/14; 71%) developed lethal ALI/ACS.

Young SS mice were treated for three months through adulthood with Nrf2 activator to stimulate HO-1 expression, and then treated with vehicle or SnPP prior to ALI/ACS induction. The SnPP-treated group developed lethal ALI-ACS while the vehicle treated SS mice with elevated HO-1 in adulthood survived. Finally, adult SS mice were concomitantly induced to develop ALI/ACS and infused with novel HO-1 recombinants or vehicle. The HO-1 recombinants attenuated lung injury and improved survival with one variant V4 affording 100% protection among a cohort of adult SS mice that would normally succumb to respiratory failure at a lethality rate of 70%.

SS mice were administered V3 (9.2 mg/kg) and V4 (13.9 mg/kg) at equivalent molar amounts to 1-261-His (5 mg/kg). Survival in mice was measured up to 120 minutes after intravenous hemin challenge to induce ACS. 100% of mice that received 1-261-Fc V3 or 1-261-Fc V4 survived (FIG. 8A) while only 20% mice that received vehicle control survived.

Figures 8A, 8B, 8C:
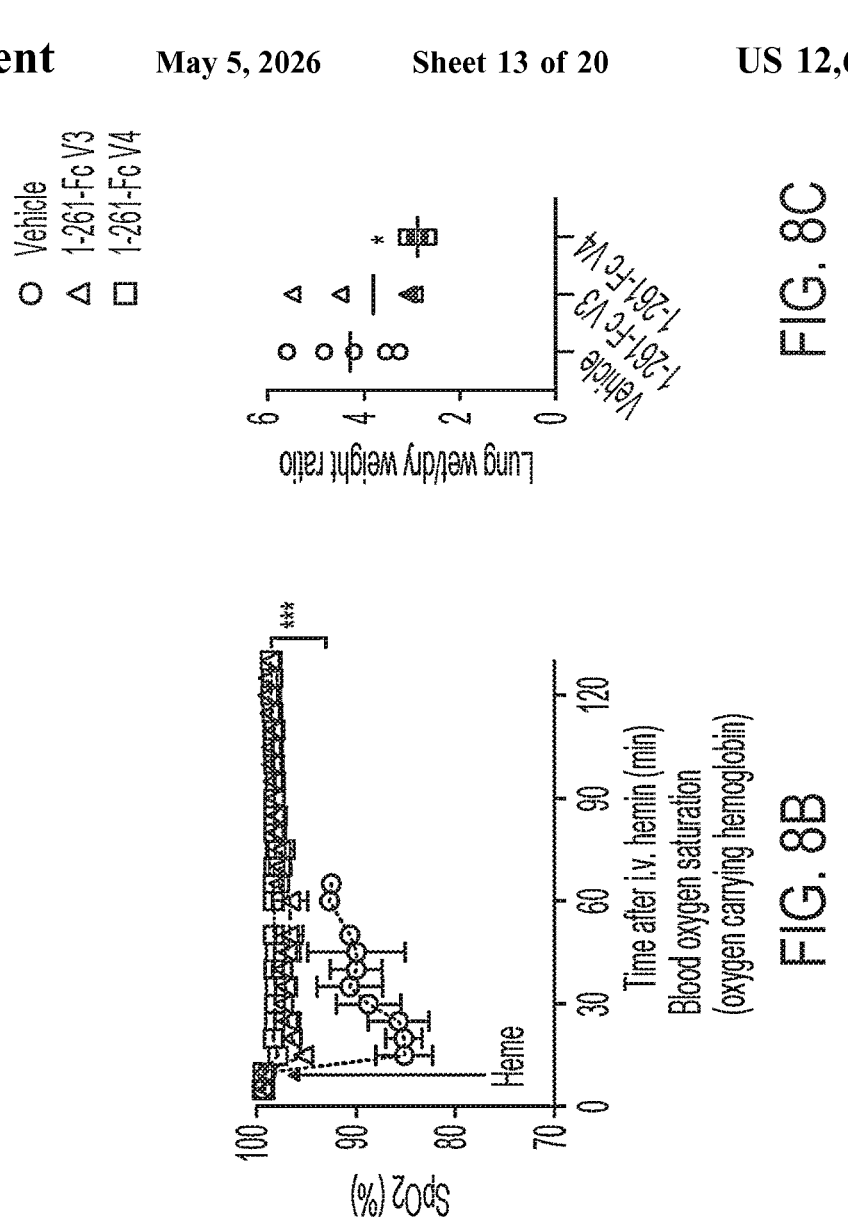
FIG. 8A shows exemplary results of survival of transgenic SCD mice infused with purified hemin to induce ACS and treated with 1-261-Fc V3, 1-261-Fc V4 or vehicle control.
FIG. 8B shows exemplary results of blood oxygen saturation levels (i.e. oxygen carrying hemoglobin) of transgenic SCD mice infused with purified hemin to induce ACS treated with 1-261-Fc V3, 1-261-Fc V4 or vehicle control.
FIG. 8C shows exemplary measurements of wet/dry weight ratios of the lungs of transgenic SCD mice infused with purified hemin to induce ACS and treated with 1-261-Fc V3, 1-261-Fc V4 or vehicle control

Blood oxygen saturation, lung wet/dry weight ratio, breath rate per minute, heart rate per minute and pulse distention were measured following intravenous challenge with hemin. Peripheral arterial blood oxygen saturation was significantly increased following administration of 1-261-Fc V3 or 1-261-Fc V4 treatment relative to a vehicle control (FIG. 8B). Mice treated with 1-261-Fc V3 (outliers included 2 visibly sick mice with low SpO2) and 1-261-Fc V4 showed reduced lung wet/dry ratio (FIG. 8C).

Figure 9C:
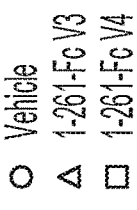
FIG. 9C shows exemplary pulse distention of transgenic SCD mice infused with purified hemin to induce ACS and treated with 1-261-Fc V3, 1-261-Fc V4 or vehicle control.
Figure 9C:
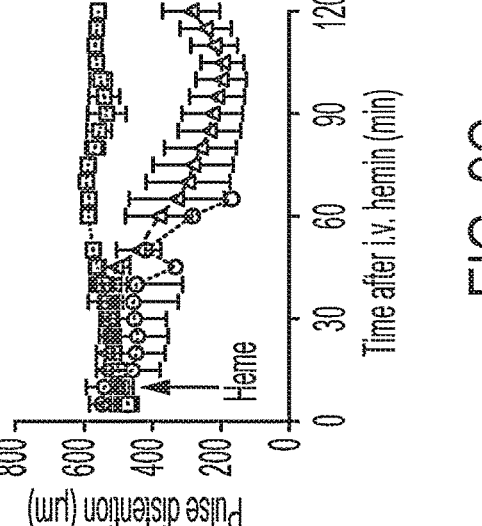
Figure 9B:
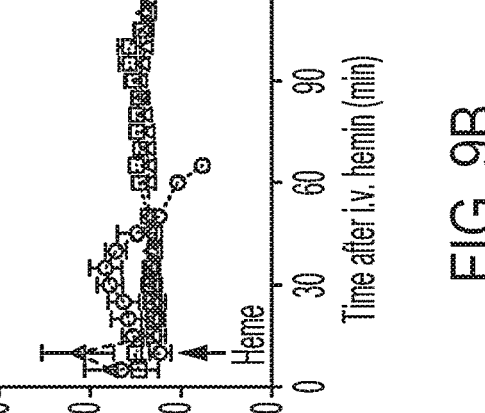
FIG. 9B shows exemplary breath rate measurements of transgenic SCD mice infused with purified hemin to induce ACS and treated with 1-261-Fc V3, 1-261-Fc V4 or vehicle control.
Figure 9A:
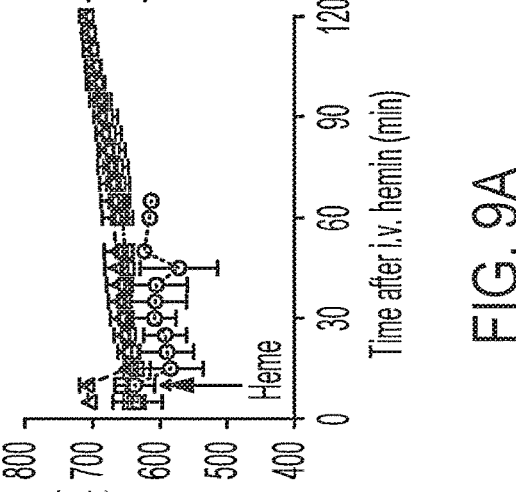
FIG. 9A shows exemplary results of heart rate measurements of transgenic SCD mice infused with purified hemin to induce ACS and treated with 1-261-Fc V3, 1-261-Fc V4 or vehicle control.

Mice treated with 1-261-Fc V3 or 1-261-Fc V4 showed increased heart rate of about 700 bpm, relative to vehicle treated controls that measured 600 bpm (FIG. 9A). Mice treated with 1-261-Fc V3 or 1-261-Fc V4 showed sustained breath rate of about 125 bpm relative to vehicle treated controls (FIG. 9B). Mice treated with 1-261-Fc V4 showed increased and sustained pulse distention of about 600 μm relative to vehicle-treated control mice. Treatment with 1-261-Fc V3 showed sustained pulse distention as compared to vehicle-treated control mice but only at about 300 μm (FIG. 9C).

Mice treated with 1-261-Fc V3 or V4 showed improved survival after hemin challenge relative to a vehicle control. In addition, there was increased blood saturation oxygen and decreased lung wet/dry weight ratio in mice treated with recombinant heme oxygenase. Treatment with V3 or V4 also improved heart rate and breath rate in mice. V4 treatment also improved pulse distention.

Example 6. RHO-1 Enzyme Kinetics

Figure 11:
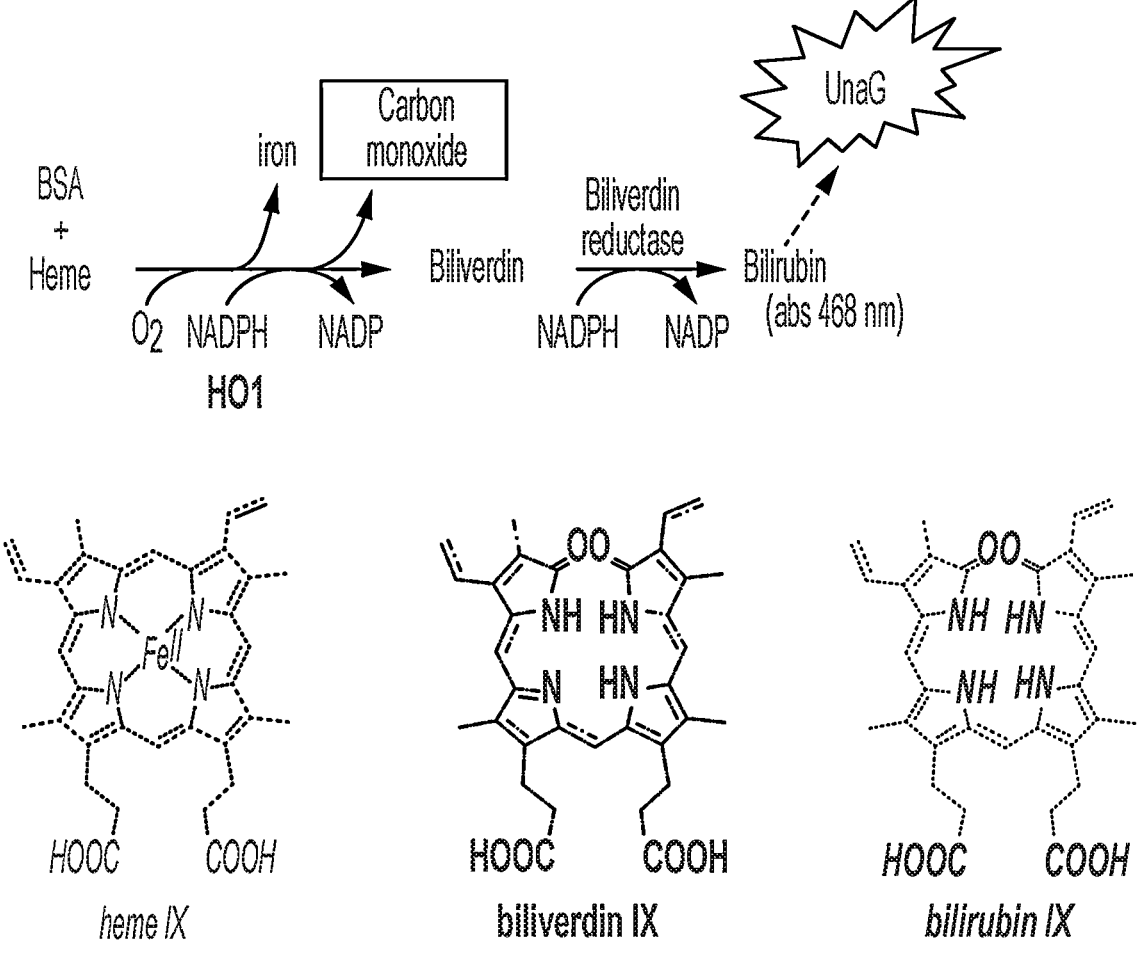
FIG. 11 shows a schematic of the UnaG assay to measure HO-1 enzyme activity with high sensitivity. HO-1 catalyzes the production of biliverdin from heme, which is converted by biliverdin reductase to bilirubin. UnaG is a fluorescent protein that binds bilirubin resulting in a complex that is measured by fluorescence emitted at ~520 nm.

This example illustrates use of a sensitive assay for measuring rHO-1 enzyme kinetics. rHO-1 catalytic activity can be measured in an enzyme linked assay measuring bilirubin absorbance. However, enzyme linked assay measuring bilirubin absorbance assays requires a large amount of product and reagent in microgram amounts. Further, dose-dependent linearity and batch to batch reproducibility remain challenging. A fluorescent assay using UnaG®, which is a 16 kDa fluorescent protein from Japanese eel muscle that binds Bilirubin with 1:1 stoichiometry to create a complex that excites at 480 nm and emits at ~520 nm was used to determine enzyme kinetics of the rHO-1-Fc constructs. This provides a sensitive reporter for detection of product to assess rHO-1 enzyme kinetics (FIG. 11).

Figure 12A:
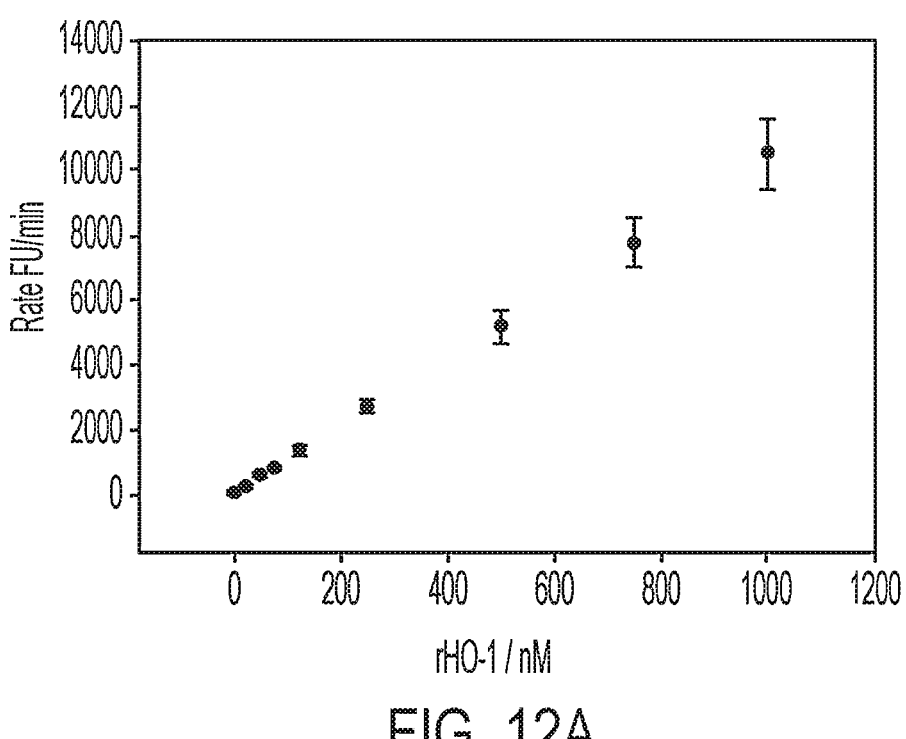
FIG. 12A shows a linear dose-response curve for HO-1 enzyme activity up to about 1000 nM HO-1 amounts as measured by the UnaG assay.
Figure 12B:
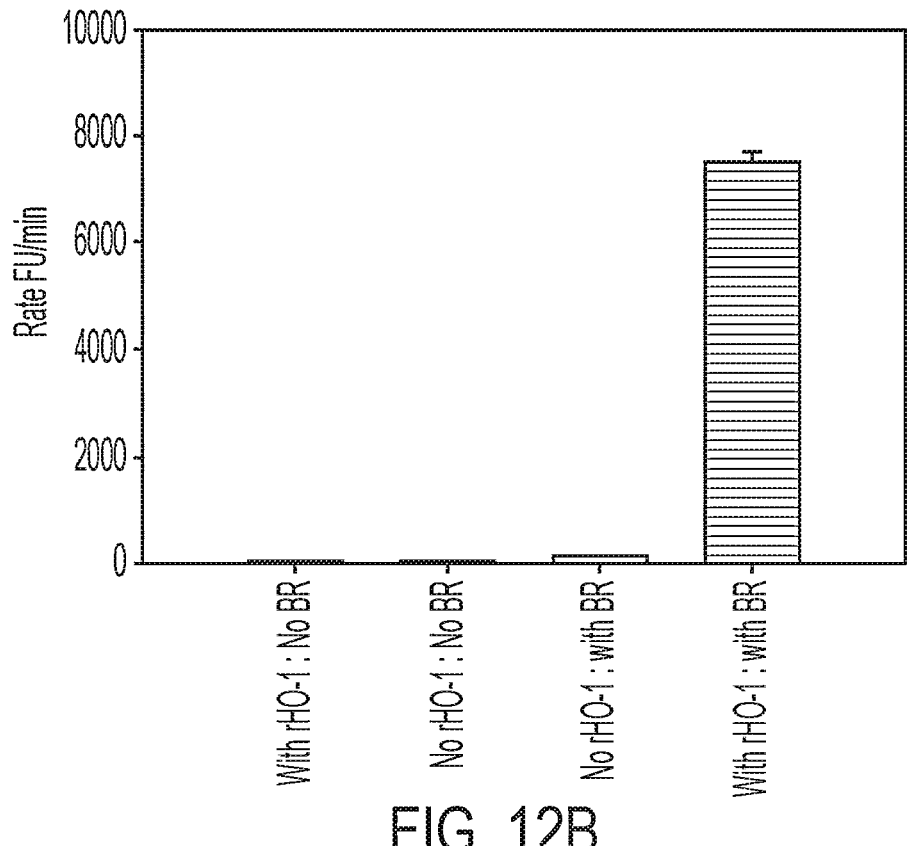
FIG. 12B shows that the UnaG assay is specific as fluorescence is obtained only in the presence of biliverdin reductase and rHO-1 enzyme. The assay is substantially free of background fluorescence. In the absence of rHO-1, there is no fluorescence observed due to lack of biliverdin substrate. In the absence of biliverdin reductase, there is no fluorescence observed as no bilirubin is available to bind UnaG.

His-tagged UnaG® was expressed in *E. coli* from an expression vector and purified by affinity purification using a nickel column and dialysis to about >90% pure. Assay conditions included 100 nmol HO-1-Fc construct, 10 UM Hemin+BSA, 250 μM NADPH, 0.5 μM Biliverdin reductase, 2 μM UnaG in a 10 μL assay volume. The UnaG assay demonstrated dose dependent activity for HO-1 (FIG. 12A) and does not have background fluorescence (FIG. 12B).

Figure 13A:
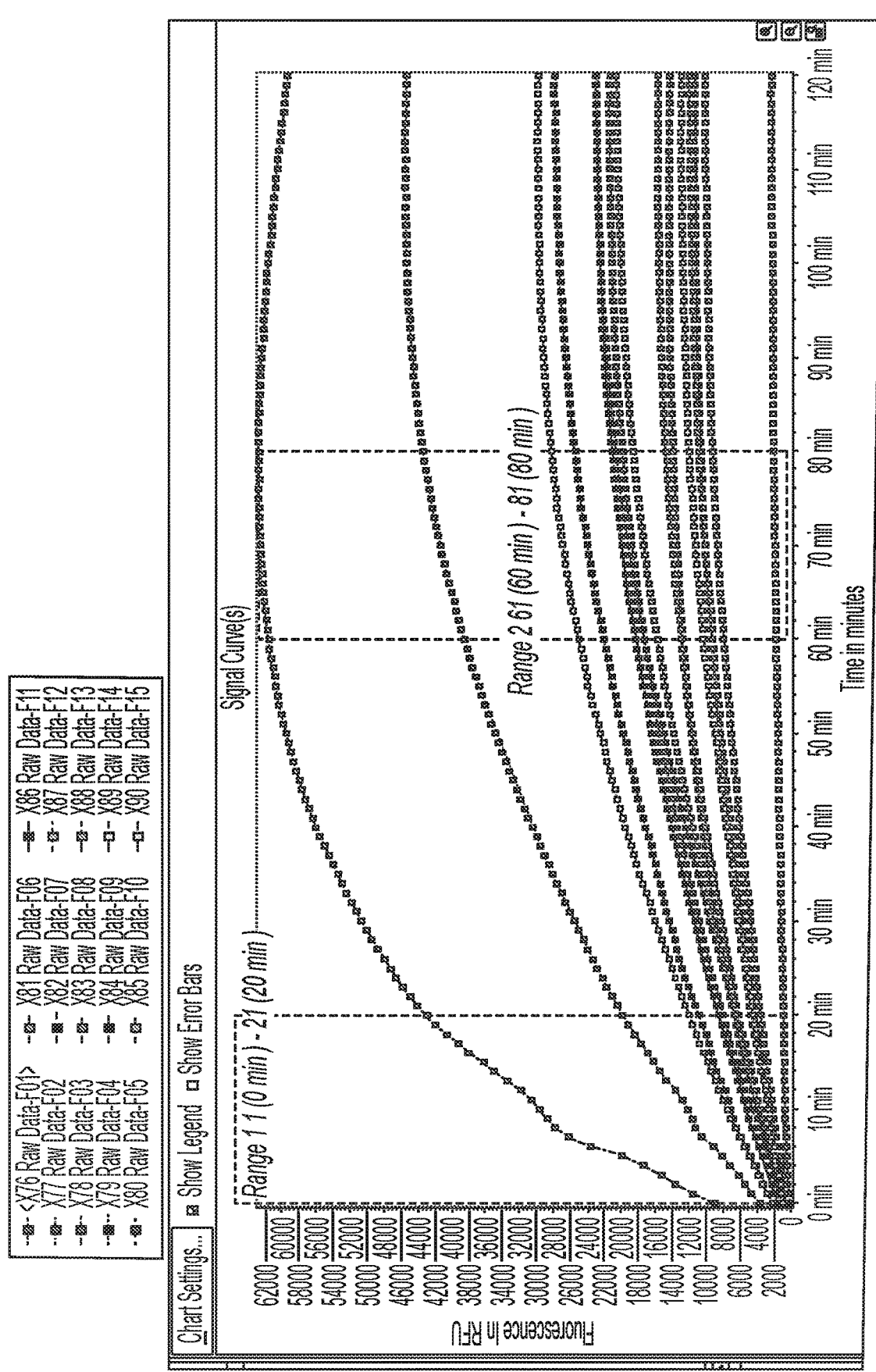
FIG. 13A shows rHO-1 enzyme activity traces with catalase and P450 oxidoreductase (POR).
Figure 13B:
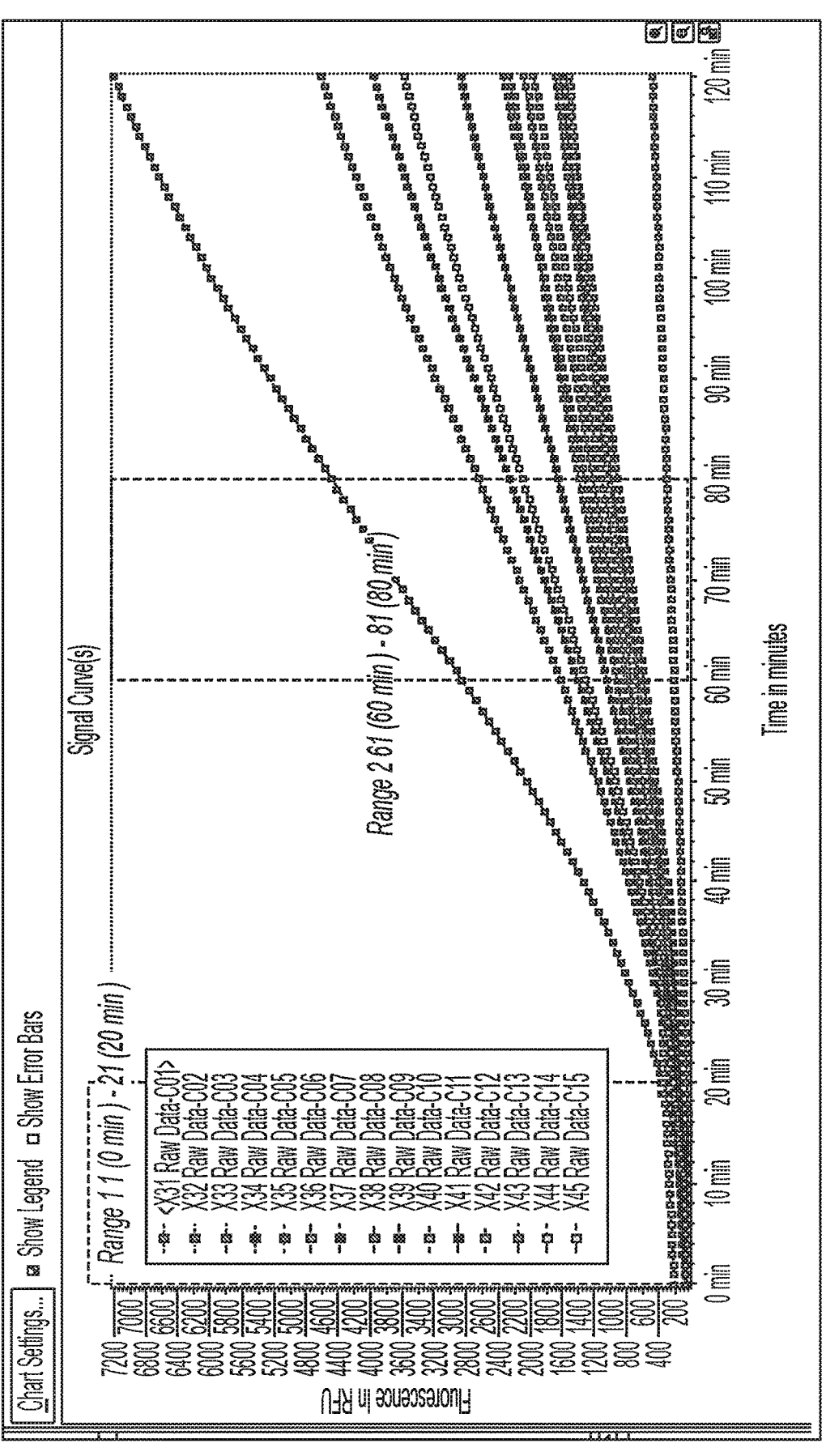
FIG. 13B shows rHO-1 enzyme activity traces without catalase and POR.

Heme oxygenase (HO) degrades heme in concert with NADPH cytochrome P450 reductase (CPR) which donates electrons to the reaction. P450 oxidoreductase (POR) transports electrons from NADPH to cytochrome P450. A molar comparison of rHO-1-Fc constructs with or without P450 cytochrome (POR)/catalase was performed as shown in FIG. 13A (with catalase and POR) and 13B (without catalase and POR).

As shown in Table 5, the average rate of HO-1 enzyme activity measured in Fluorescent Units/minute without catalase and without POR were between 60-80 min. The average rate of Fluorescent Units/minute with catalase and with POR are calculated between 0-20 min. and values shown in Table 5. These results suggest that the assay is highly reproducible, used much less reagent, and can be conducted in a high throughput manner.

TABLE 5

Average rate of HO-1 Enzyme Activity (Fluorescent Units/minute)

| Sample | Without catalase and POR Av Rate FU/min | With catalase and POR Av Rate FU/min | SD |
|---|---|---|---|
| 1-261-His | — | 342.32 | 45.27 |
| V1 | 55.23 | 880.22 | 74.11 |
| V2 | 86.15 | 1815.81 | 232.02 |
| V3 | 44.13 | 477.60 | 45.43 |
| V4 | 22.53 | 382.31 | 21.72 |
| V4 (10 L prep) | 25.96 | 306.14 | 39.11 |
| V5 | 17.90 | 217.80 | 26.23 |
| V6 | 16.12 | 221.54 | 39.68 |

56

TABLE 5-continued

Average rate of HO-1 Enzyme Activity (Fluorescent Units/minute)

| Sample | Without catalase and POR Av Rate FU/min | With catalase and POR Av Rate FU/min | SD |
|---|---|---|---|
| V7 | 19.39 | 241.70 | 51.72 |
| V8 | 4.73 | 35.15 | 5.07 |
| V9 | 28.60 | 386.86 | 63.07 |
| V10 | 22.80 | 283.54 | 24.00 |
| V11 | 17.93 | 150.15 | 2.68 |
| V12 | 40.83 | 469.79 | 40.68 |
| V15 | 14.45 | 180.76 | 5.31 |

Example 7. In Vivo Efficacy of rHO-1 (1-261)-Fc V4 Fusion Heme Oxygenase Truncated Protein This example illustrates in vivo efficacy of different doses of recombinant heme oxygenase Fc fusion proteins in increasing survival in mice that received the treatment.

Figures 10A, 10B:
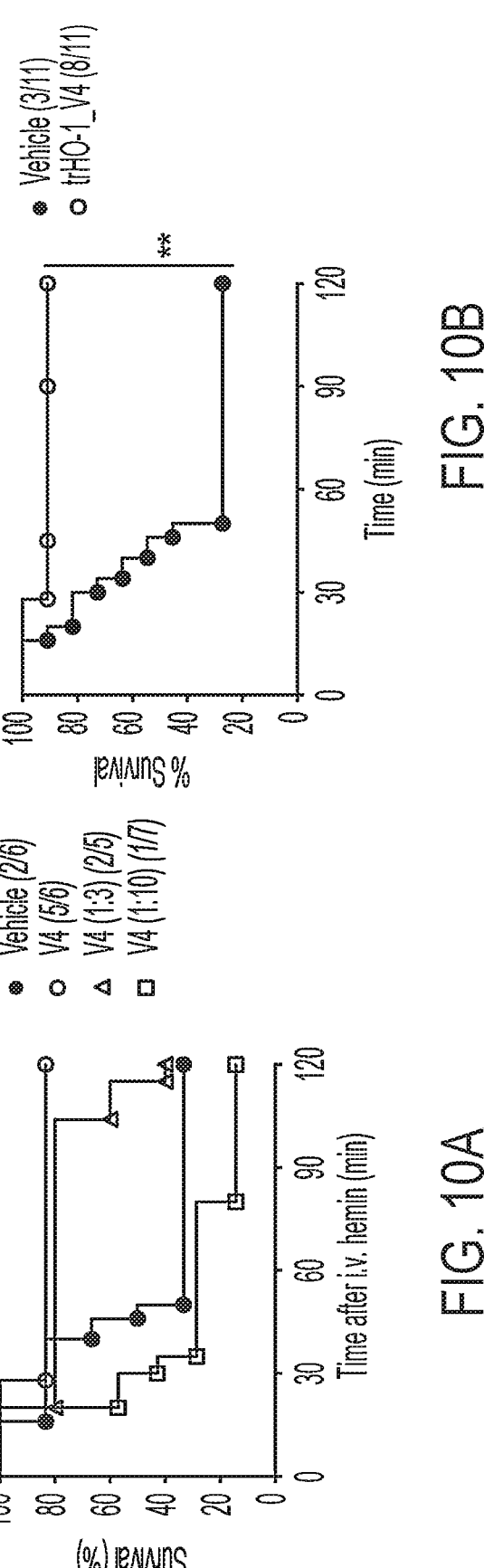
FIG. 10A shows exemplary results of survival of transgenic SCD mice infused with purified hemin to induce ACS and treated with different doses of rHO-1-Fc V4 or vehicle control.
FIG. 10B shows exemplary results of survival of transgenic SCD mice infused with purified hemin to induce ACS and treated with different doses of rHO-1-Fc V4 or vehicle control.

To determine the efficacy of rHO-1-Fc V4, SS mice were administered a single intravenous dose of rHO-1-Fc v4 of either 1.4 mg/kg, 4.7 mg/kg or 13.9 mg/kg (equimolar to ⅒th, ⅓rd, or a total 5 mg/kg dose of rHO-1 [1-261]-His respectively) or carrier vehicle. Survival in mice was measured up to 120 minutes after intravenous hemin challenge to induce ACS. In this study, about 80% of mice that received 13.9 mg/kg (equimolar to 5 mg/kg dose) 1-261-Fc V4 survived and about 40% of mice that received 4.7 mg/kg (⅓rd) survived while only about 30% mice that received vehicle control survived (FIG. 10A).

SS mice were given a single intravenous dose of rHO-1-Fc V4 of 13.9 mg/kg (equimolar to a 5 mg/kg dose of rHO-1 [1-261]-His) or carrier vehicle. Survival in mice was measured up to 120 minutes after intravenous hemin challenge to induce ACS. 90% of mice that received rHO-1-Fc V4 survived (FIG. 10B) while only 25% of mice that received vehicle control survived.

Figure 10D:
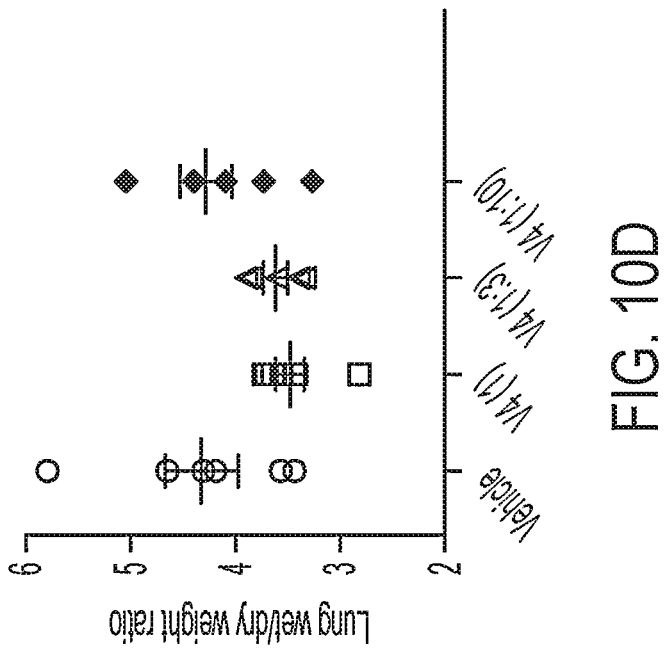
FIG. 10D shows exemplary measurements of wet/dry weight ratios of the lungs of transgenic SCD mice infused with purified hemin to induce ACS and treated with different doses of rHO-1-Fc V4 or vehicle control.
Figure 10C:
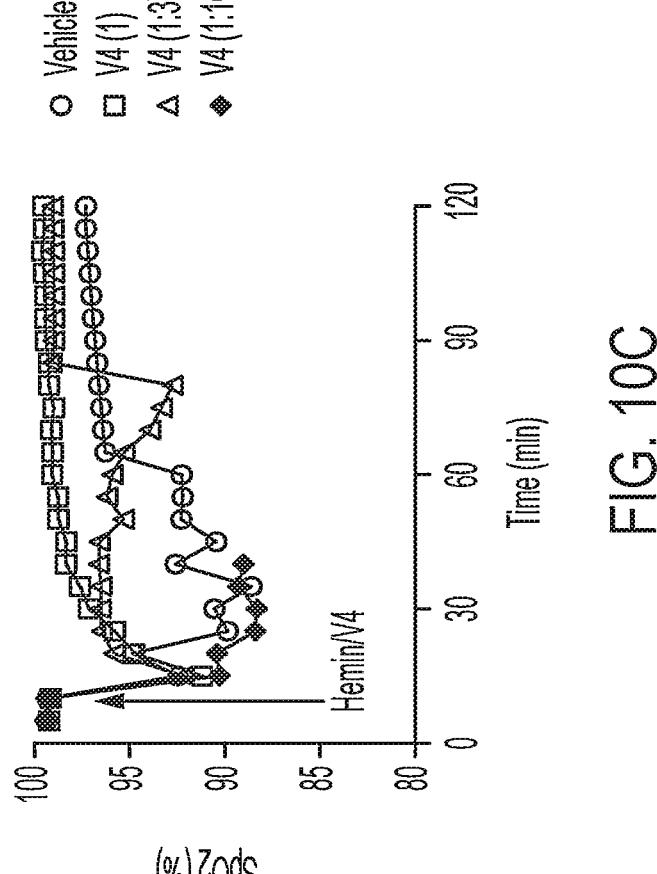
FIG. 10C shows exemplary results of blood oxygen saturation levels (i.e. oxygen carrying hemoglobin) of transgenic SCD mice infused with purified hemin to induce ACS treated with different doses of rHO-1-Fc V4 or vehicle control.

Blood oxygen saturation, lung wet/dry weight ratio, breath rate per minute, heart rate per minute and pulse distention were measured following intravenous challenge with hemin. Peripheral arterial blood oxygen saturation was significantly increased following administration of 1-261-Fc V4 treatment relative to a vehicle control for mice administered with 13.9 mg/kg or 4.7 mg/kg V4 (FIG. 10C). Vehicle data, and data for mice administered 4.7 mg/kg or 1.4 mg/kg V4 were from SS mice that expired within 2h following of hemin infusion. Mice treated with 13.9 mg/kg or 4.7 mg/kg rHO-1-Fc V4 showed reduced lung wet/dry ratio relative to mice treated with a vehicle control (FIG. 10D).

Figure 5C:
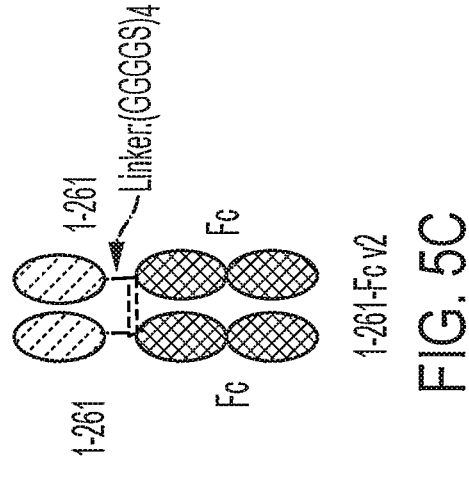
FIG. 5C discloses SEQ ID NO: 21, FIG. 5D discloses SEQ ID NO: 21, FIG. 50 discloses SEQ ID NO: 64, FIG. 5P discloses SEQ ID NO: 63 and FIG. 5Q discloses SEQ ID NO: 64.
Figure 5E:
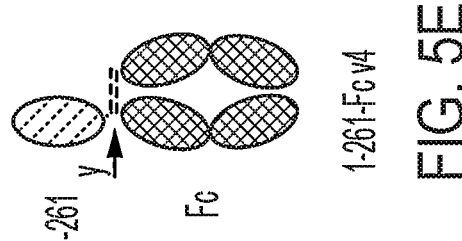
FIG. 5A-5Q show schematics of HO-1 1-261-His and Fc fusion constructs V1-V16 generated for extended half-life and/or reduced aggregation.
Figure 5B:
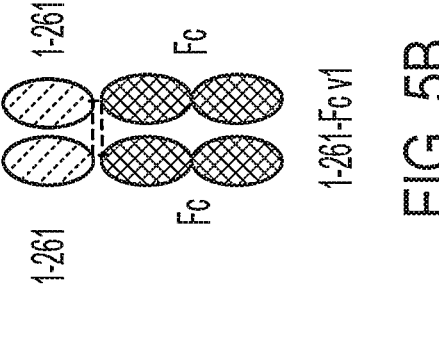
Figure 5D:
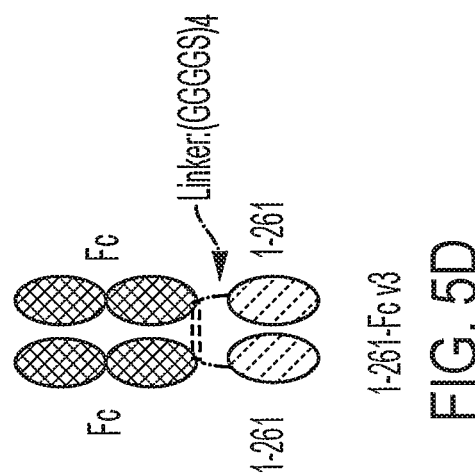
Figure 5A:
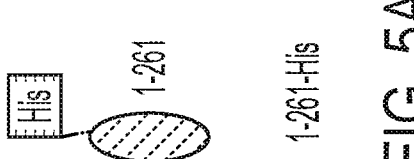
Figure 5I:
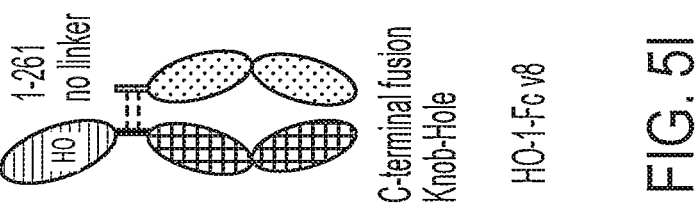
Figure 5H:
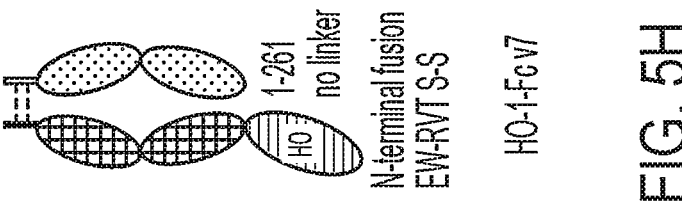
Figure 5G:
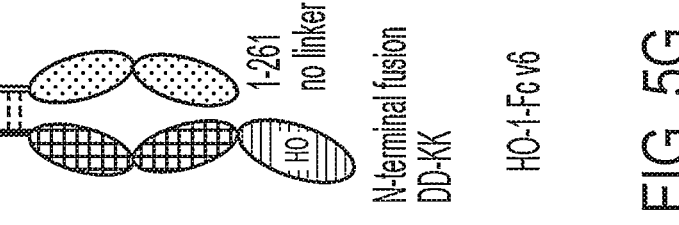
Figure 5F:
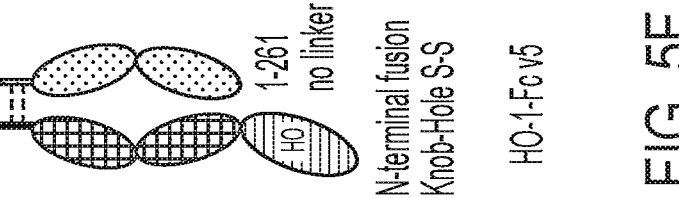
Figures 5J, 5K, 5L, 5M:
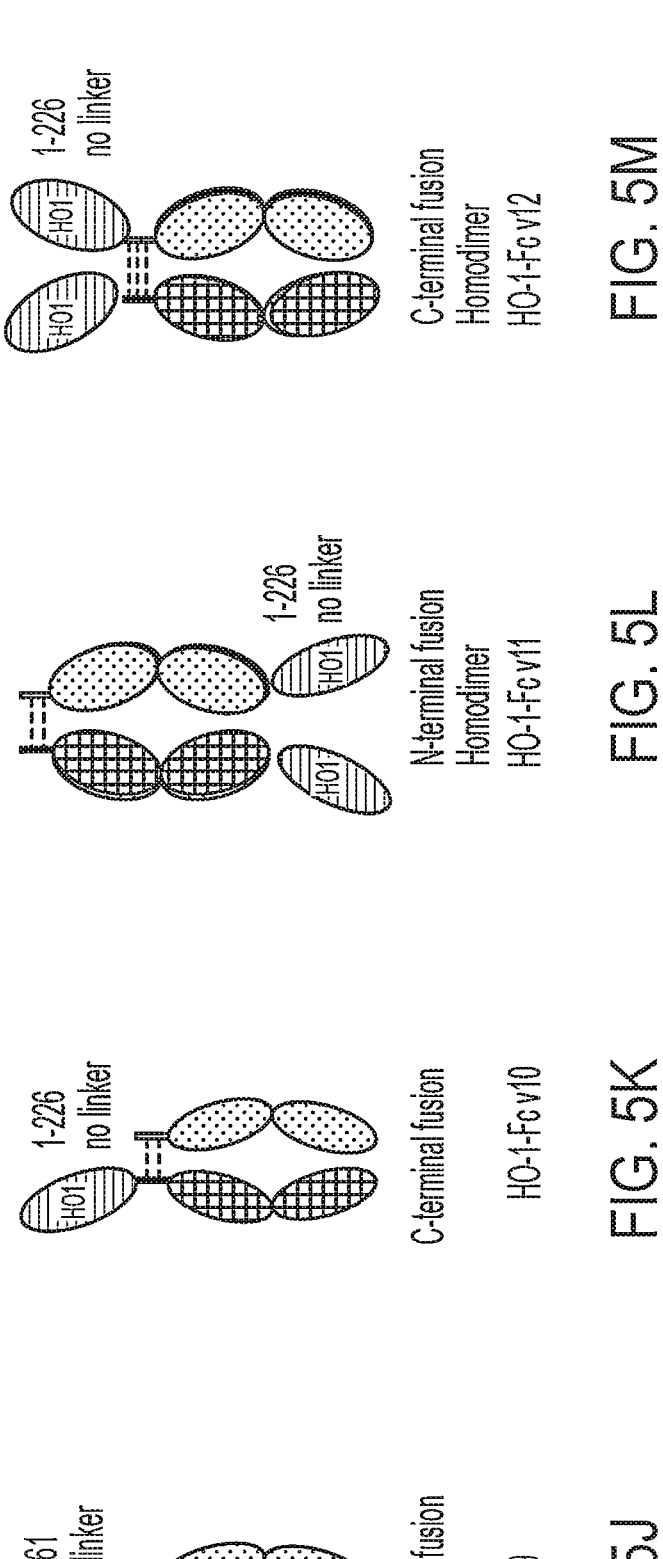
Figure 5Q:
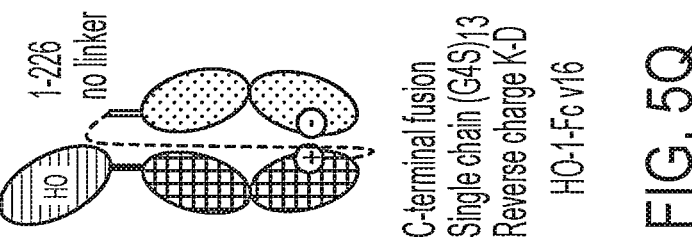
Figure 5P:
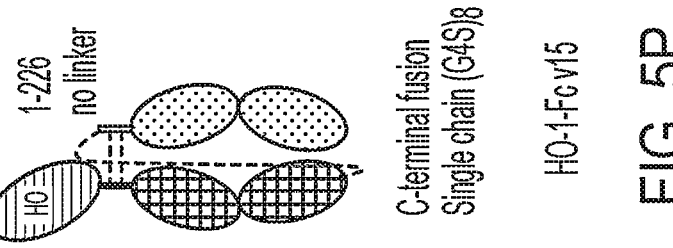
Figure 5O:
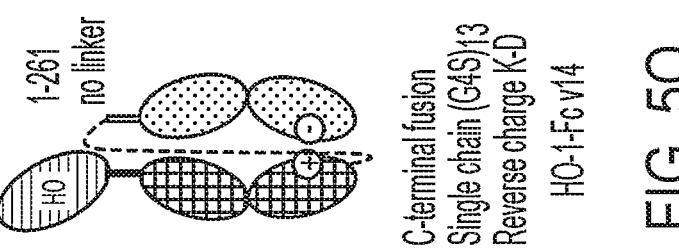
Figure 5N:
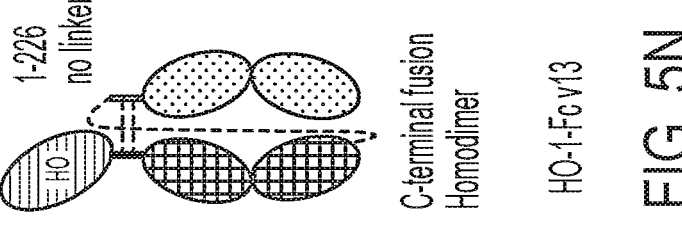

Example 8. RHO-1 (1-261)-Fc Chimeras with Reduced Aggregation rHO (1-261)-Fc chimeric constructs were developed with improved properties compared to recombinant HO-1 alone (FIG. 5A-5Q). Constructs were designed to improve batch to batch reproducibility in CHO cell lines without post-translational modifications. Additionally, the rHO-1 Fc fusion variants demonstrate reduced aggregation of full length (1-261) rHO-1-Fc during affinity purification and SEC in PBS.

Constructs v1-v16 were transiently transfected and expressed in 100 mL EBNA1 cells. In an exemplary expression protocol, 1:1 ratios of each Fc chain, sheared salmon sperm DNA (filler DNA) and XBPIS (co-expressed to improve folding and secretion) were loaded onto a Maxcyte CL1.1 cassette and electroporated. 48 hours post-transfection, 0.125% N,N Dimethylacetamide was added and cell feed with 3% SAFC Advanced Feed 1 was provided daily until day 8. Constructs are purified using a citrate gradient followed by a polishing step on SEC in PBS.

Constructs were screened and selected if >95% purity was achieved after two rounds of purification and were resistant to thermal stress (3×Freeze Thaw analysis). Enzymatic activity of heme breakdown was tested in in vitro assays to identify constructs that achieved similar robustness and activity relative to cell free (cf) HO-1. As shown in Table 6, HO-1 activity of rHO-1-Fc constructs was assessed relative to the V4 construct. V12, V10, and V7 demonstrated robust enzymatic activity and were purified with high yield.

TABLE 6

Enzymatic fold difference of rHO-1 constructs relative to V4.

| rHO-1-Fc Name | Enzymatic Fold diff. to V4 10 L prep, mol equivalent | Enzymatic Fold diff, to V4 10 L prep. HO-1 valency equivalent |
|---|---|---|
| V1 | 0.47 | 0.94 |
| V2 | 0.3 | 0.6 |
| V3 | 0.59 | 1.18 |
| V4 | 1.15 | 1.15 |
| V5 | 1.45 | 1.45 |
| V6 | 1.61 | 1.61 |
| V7 (3) | 1.34 | 1.34 |
| V8 | 5.49 | 5.49 |
| V9 | 0.91 | 0.91 |
| V10 (2) | 1.14 | 1.14 |
| V11 | 1.45 | 2.9 |
| V12 (1) | 0.64 | 1.27 |
| V15 | 1.8 | 1.8 |

Example 9. Pharmacokinetic Profile of rHO-1 V7, V10 and V12 Fusion Proteins

To evaluate the pharmacokinetic profile of the rHO-1-Fc fusion proteins, male C57BL/6 (Jax) mice (4 mice per time points) were administered intravenous injections of 5 mg/kg V7, V10, V12 or V4 (control). Serum rHO-1 was collected at 5m, 6 h, 24 h, 72h, 168h, 240h and 336h. Plasma rHO-1 will be measured by ELISA assay.

Example 10. RHO-1-Fc V4 Fusion Protein In Vivo

This example illustrates administration of rHO-1-Fc V4 fusion protein in an HbSS and an HbAA mouse model. Male and female HbSS and HbAA mice are intravenously injected with rHO-1-Fc V4 fusion protein or PBS as a control weekly. HbSS mice are intravenously administered with a weekly dose of 13.9 mg/kg of HO-1, 5 mL/kg of HO-1 V4. Response following in vivo treatment with rHO-1 V4 are monitored by evaluating real time oxygen saturation, breath rate, heart rate, pulse distention and lung wet/dry ratio as surrogate clinical outcomes, as described in Example 3.

Blood for hematological assessment and organs for histopathology, immunohistochemistry and quantitative plasma assays are collected at 10 weeks, 12 weeks, 16 weeks and 20 weeks as shown in Table 7. Hematology endpoint assessments will measure hemoglobin, red blood cells mean corpuscular volume (MCV), white blood cells and differential, reticulocytes, % sickle erythrocytes, w/microscopic pictures, $spo_2$, heart rate, plasma free heme, plasma free hemoglobin, plasma hemopexin, plasma haptoglobin, and d-dimer quantification. Histopathology studies will assess liver, lung (no lavage), spleen including weight (% body weight), kidney, brain, and heart. Immunohistochemistry analysis will be performed to evaluate H&E, iron, p-selectin, ICAM, V-CAM, lymphocytes, oxidative stress markers and kidney depot C3/C5. Quantitative plasma assays will be used to measure ferritin, iron, transferrin, bilirubin, AST, ALT, LDH, NO, and pro-inflammatory cytokines using multiplex cytokine release. Pharmacokinetic studies of rHO-1 V4 fusion protein administration are performed in HbAA mice from groups 11 and 12.

TABLE 7

Timeline for blood and organ collection

| Group | Genotype | Injection | Time-point for blood and organ collection |
|---|---|---|---|
| 0 | HbSS | PBS | 10 weeks |
| 1 | HbSS | PBS | 12 weeks |
| 2 | HbSS | 13.9 mg/kg HO-1 V4: 5 mL/kg | 12 weeks |
| 3 | HbSS | PBS | 16 weeks |
|  | HbSS | 13.9 mg/kg HO-1 V4: 5 mL/kg | 16 weeks |
| 5 | HbSS | PBS | 20 weeks |
|  | HbSS | 13.9 mg/kg HO-1 V4: 5 mL/kg | 20 weeks |
| 7 | HbAA | PBS | 10 weeks |
| 8 | HbAA | PBS | 12 weeks |
| 9 | HbAA | PBS | 16 weeks |
| 10 | HbAA | PBS | 20 weeks |
| 11 | HbAA | 13.9 mg/kg HO-1 V4: 5 mL/kg | 2 days, week 11, 13, 15, 17, 19 |
| 12 | HbAA | 13.9 mg/kg HO-1 V4: 5 mL/kg | 2 h, 4 days, week 12, 14, 16, 18, 20 |

Toxicity Profile of rHO-1-Fc V4 Fusion Protein

To measure toxicity of rHO-1-Fc V4 fusion protein, 14-16 wk old HbSS and HbAA mice (mature SCD phenotype) are administered a single escalating dose rHO-1-Fc V4 selected from the following doses: 0, 15, 50 or 150 mg/kg. 6 mice per sex will be administered rHO-1 at each dose tested in the study. After 2h intravenous exposure to rHO-1-Fc bilirubin toxicity endpoints are measured followed by serum and tissue iron levels at 7 days post injection.

TABLE 8

Conditions for determining in vivo toxicity profile of rHO-1-Fc V4.

| Group | Genotype | rHO-1-Fc V4 (mg/kg) | Volume (mL/kg) | Concentration (mg/mL) |
|---|---|---|---|---|
| 1 | HbSS | 0 | 5 | 0 |
| 2 | HbSS | 15 | 5 | 3 |
| 3 | HbSS | 50 | 5 | 10 |
| 4 | HbSS | 150 | 5 | 30 |
| 5 | HbAA | 0 | 5 | 0 |
| 6 | HbAA | 150 | 5 | 30 |

Example 11. HO-1 Levels Associate with Risk of ACS in SCD Patients

Previous genetic association studies have linked high heme oxygenase-1 (HO-1) expression with low ACS risk in children. SCD patients were evaluated for HO-1 levels. The present study shows for the first time that the concentration of plasma HO-1 in SCD children 1-9 yrs is 2-fold higher than adults 20 yrs and older (23.6±1.1, n=191 versus mean 10.7±0.6, n=67).

INCORPORATION BY REFERENCE

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

---

The invention claimed is:

1. A method of treating sickle cell disease comprising administering to a subject in need of treatment a truncated recombinant heme oxygenase-1 (rHO-1) protein, comprising an amino acid sequence with at least 85% identity to residues 1-261 of SEQ ID NO: 1, wherein the rHO-1 protein comprises an F33L amino acid substitution in SEQ ID NO: 1.

2. The method of claim 1, wherein the rHO-1 protein comprises an Fc domain fused to the rHO-1 protein domain, wherein the Fc domain is fused to the N-terminus or C-terminus of the rHO-1 protein domain.

3. The method of claim 2, wherein the rHO-1 protein is a multimer comprising at least one monomer comprising an Fc domain fused to an rHO-1 protein domain.

4. The method of claim 1, wherein the rHO-1 protein is truncated at T261.

5. The method of claim 1, wherein the rHO-1 protein comprises an amino acid sequence with 95% identity to residues 1-226 of SEQ ID NO: 1.

* * * * *